(12) United States Patent
Amans et al.

(10) Patent No.: US 8,993,554 B2
(45) Date of Patent: Mar. 31, 2015

(54) TETRAHYDROQUINOLINE DERIVATIVES USEFUL AS BROMODOMAIN INHIBITORS

(75) Inventors: Dominique Amans, Stevenage (GB); Emmanuel Hubert Demont, Stevenage (GB); Darren Jason Mitchell, Stevenage (GB); Jonathan Thomas Seal, Stevenage (GB)

(73) Assignee: GlaxoSmithKline LLC, Wilmington, New Castle, DE (US)

( * ) Notice: Subject to any disclaimer, the term of this patent is extended or adjusted under 35 U.S.C. 154(b) by 0 days.

(21) Appl. No.: 14/111,625

(22) PCT Filed: Apr. 19, 2012

(86) PCT No.: PCT/EP2012/057113
§ 371 (c)(1), (2), (4) Date: Oct. 14, 2013

(87) PCT Pub. No.: WO2012/143415
PCT Pub. Date: Oct. 26, 2012

(65) Prior Publication Data
US 2014/0031336 A1    Jan. 30, 2014

(30) Foreign Application Priority Data

Apr. 21, 2011 (GB) .................................. 1106750.1

(51) Int. Cl.
*C07D 215/42* (2006.01)
*C07D 401/12* (2006.01)
*C07D 401/14* (2006.01)
*C07D 215/44* (2006.01)
*C07D 401/04* (2006.01)

(52) U.S. Cl.
CPC ............ *C07D 215/42* (2013.01); *C07D 215/44* (2013.01); *C07D 401/04* (2013.01); *C07D 401/12* (2013.01); *C07D 401/14* (2013.01)
USPC .............. 514/210.18; 514/235.2; 514/253.06; 514/255.05; 514/275; 514/313; 544/120; 544/128; 544/331; 544/363; 544/405; 546/162

(58) Field of Classification Search
None
See application file for complete search history.

(56) References Cited

FOREIGN PATENT DOCUMENTS

| WO | 2011/054848 A1 | 5/2011 |
| WO | 2011/054851 A1 | 5/2011 |
| WO | 2011/054843 A1 | 10/2013 |

OTHER PUBLICATIONS

Mertz et al., Targeting MYC Dependence in Cancer by Inhibiting BET Bromodomains, 108(40) PNAS 16669-16674 (Oct. 2011).*
Denis, G., Ph. D., Bromodomain Coactivors in Cancer, Obesity, Type 2 Diabetes and Inflammation, 10(55) Discov. Med. 489-499 (Dec. 2010).*

* cited by examiner

*Primary Examiner* — Timothy R Rozof
(74) *Attorney, Agent, or Firm* — Robert H. Brink

(57) ABSTRACT

Tetrahydroquinoline compounds, pharmaceutical compositions containing such compounds and their use in therapy.

16 Claims, No Drawings

TETRAHYDROQUINOLINE DERIVATIVES USEFUL AS BROMODOMAIN INHIBITORS

CROSS-REFERENCE TO RELATED APPLICATIONS

This application is filed pursuant to 35 USC 371 as a United States National Phase Application of International Patent Application Serial No. PCT/EP2012/057113 filed on Apr. 19, 2012, which claims priority from 1106750.1 filed on Apr. 21, 2011 in the United Kingdom.

FIELD OF THE INVENTION

The present invention relates to tetrahydroquinoline derivatives, pharmaceutical compositions containing such compounds and to their use in therapy.

BACKGROUND OF THE INVENTION

The genomes of eukaryotic organisms are highly organised within the nucleus of the cell. The long strands of duplex DNA are wrapped around an octomer of histone proteins (most usually comprising two copies of histones H2A, H2B H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRD-t) which contain tandem bromodomains capable of binding to two acetylated lysine residues in close proximity, increasing the specificity of the interaction. BRD2 and BRD3 are reported to associate with histones along actively transcribed genes and may be involved in facilitating transcriptional elongation (Leroy et al, Mol. Cell. 2008 30(1):51-60), while BRD4 appears to be involved in the recruitment of the pTEF-3 complex to inducible genes, resulting in phosphorylation of RNA polymerase and increased transcriptional output (Hargreaves et al, Cell, 2009 138(1): 129-145). It has also been reported that BRD4 or BRD3 may fuse with NUT (nuclear protein in testis) forming novel fusion oncogenes, BRD4-NUT or BRD3-NUT, in a highly malignant form of epithelial neoplasia (French et al. Cancer Research, 2003, 63, 304-307 and French et al. Journal of Clinical Oncology, 2004, 22 (20), 4135-4139). Data suggests that BRD-NUT fusion proteins contribute to carcinogensesis (Oncogene, 2008, 27, 2237-2242). BRD-t is uniquely expressed in the testes and ovary. All family members have been reported to have some function in controlling or executing aspects of the cell cycle, and have been shown to remain in complex with chromosomes during cell division—suggesting a role in the maintenance of epigenetic memory. In addition some viruses make use of these proteins to tether their genomes to the host cell chromatin, as part of the process of viral replication (You et al Cell, 2004 117(3):349-60).

Japanese patent application JP2008-156311 discloses a benzimidazole derivative which is said to be a BRD2 bromodomain binding agent which has utility with respect to virus infection/proliferation.

Patent application WO2009084693 discloses a series of thienotriazolodiazepiene derivatives that are said to inhibit the binding between an acetylated histone and a bromodomain containing protein which are said to be useful as anti-cancer agents.

PCT patent applications PCT/EP2010/06693 and PCT/EP2010/066701 disclose a series of tetrahydroquinoline derivatives that inhibit the binding of BET family bromodomains with acetylated lysine residues.

A novel class of compounds have been found which inhibit the binding of bromodomains with its cognate acetylated proteins, more particularly a class of compounds that inhibit the binding of BET family bromodomains to acetylated lysine residues. Such compounds will hereafter be referred to as "bromodomain inhibitors".

SUMMARY OF THE INVENTION

In a first aspect of the present invention, there is provided a compound of formula (I) or a salt thereof, more particularly a pharmaceutically acceptable salt thereof

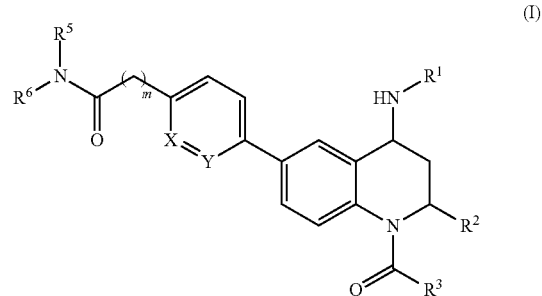

(I)

In a second aspect of the present invention, there is provided a pharmaceutical composition comprising a compound of formula (I) or a pharmaceutically acceptable salt thereof and one or more pharmaceutically acceptable carriers, diluents or excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

DETAILED DESCRIPTION OF THE INVENTION

The present invention relates to a compound of formula (I) or a salt thereof.

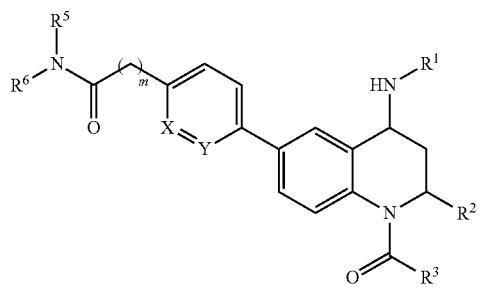

(I)

in which
X and Y are independently CH or N provided that at least one of X and Y must be CH;
$R^1$ is a group $C(O)OR^4$ in which $R^4$ is $C_{1-3}$alkyl or $C_{3-7}$cycloalkyl; or
$R^1$ is a group selected from phenyl, pyridyl, pyrazinyl and pyrimidinyl said groups being optionally substituted by one or two substituents selected from halogen, $C_{1-4}$alkyl and CN;
$R^2$ is $C_{1-4}$alkyl;
$R^3$ is $C_{1-4}$alkyl;
$R^5$ is hydrogen and $R^6$ is $C_{1-4}$alkyl substituted by one or more hydroxy or a —$NR^7R^8$ group in which $R^7$ and $R^8$ are independently hydrogen or a $C_{1-4}$alkyl group; or
$R^5$ and $R^6$ together with the N to which they are attached form a 4, 5 or 6 membered heterocyclyl ring optionally containing a further heteroatom selected from N, O and S, said heterocyclyl ring being optionally substituted by one or more $C_{1-4}$alkyl, hydroxyl or amino groups; and
m is 0, 1 or 2.

In one embodiment the invention provides compounds of formula (I) with cis relative stereochemistry across the tetrahydroquinoline ring in respect of the substituents in the 2 and 4 position on the ring. In one embodiment the compound of formula (I) or a salt thereof is the (2S,4R) enantiomer.

In one embodiment X and Y are both CH. In a further embodiment X is CH and Y is N. In a further embodiment X is N and Y is CH.

In one embodiment $R^1$ is a group $C(O)OR^4$ in which $R^4$ is isopropyl.

In one embodiment $R^1$ is selected from

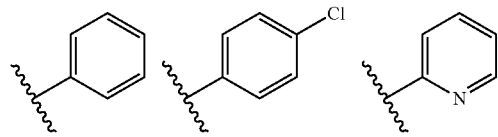

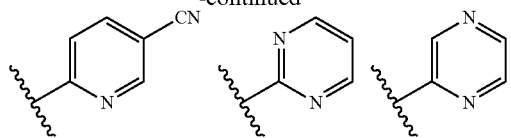

In one embodiment $R^2$ is methyl.
In one embodiment $R^3$ is methyl.
In one embodiment m is 0. In a further embodiment m is 1. In a further embodiment m is 2.
In one embodiment $R^5$ is hydrogen and $R^6$ is selected from

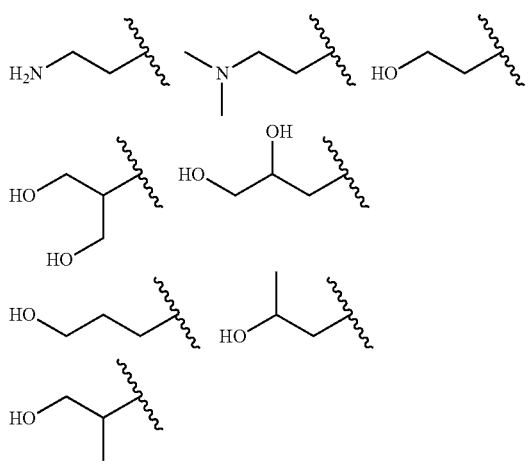

In one embodiment $R^5$ and $R^6$ together with the N to which they are attached form a 4, 5 or 6 membered heterocyclyl ring selected from azetidinyl, pyrrodinyl, piperazinyl, piperidinyl and morpholinyl said heterocyclyl ring being optionally substituted by one or more (e.g two or three) $C_{1-4}$alkyl (such as methyl), hydroxyl, or amino groups.

In a further embodiment $R^5$ and $R^6$ together with the N to which they are attached form a group selected from

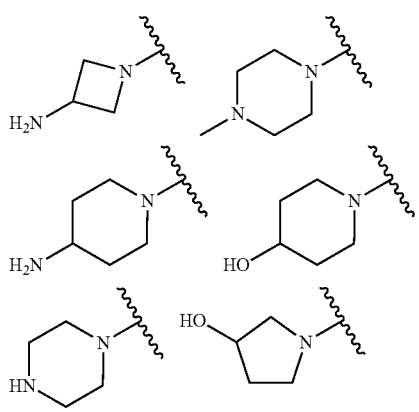

While the embodiments for each variable have generally been listed above separately for each variable, this invention is intended to include all combinations of embodiments described hereinabove including salts thereof.

Compounds according to the invention include Examples 1-68 as described herein. Particular compounds of the invention include:

2-(4-((2S,4R)-1-Acetyl-4-((5-cyanopyridin-2-yl)amino)-2-methyl-1,2,3,4-tetrahydroquinolin-6-yl)phenyl)-N-(2-(dimethylamino)ethyl)acetamide;

6-((2S,4R)-1-acetyl-4-((5-cyanopyridin-2-yl)amino)-2-methyl-1,2,3,4-tetrahydroquinolin-6-yl)-N-(2-(dimethylamino)ethyl)nicotinamide; and 6-((2S,4R)-1-acetyl-4-((5-cyanopyridin-2-yl)amino)-2-methyl-1,2,3,4-tetrahydroquinolin-6-yl)-N-(2-hydroxyethyl)nicotinamide or a salt thereof.

Throughout the present specification, unless otherwise stated:

the term "halogen" is used to describe a group selected from fluorine, chlorine or bromine;

the terms "$C_{1-3}$alkyl", "$C_{1-4}$alkyl" and "$C_{1-6}$alkyl" are used to describe a group or a part of the group comprising a linear or branched alkyl group containing from 1 to 3, 1 to 4 or 1 to 6 carbon atoms respectively. Suitable examples of such groups include methyl, ethyl, propyl, isopropyl, n-butyl, isobutyl, t-butyl, pentyl and hexyl;

the term "$C_{3-7}$cycloalkyl" is used to describe a non-aromatic carbocyclic ring containing at least three and at most seven carbon atoms. Examples of $C_{3-7}$cycloalkyl include cyclopropyl, cyclobutyl, cyclopentyl, cyclohexyl and cycloheptyl.

It will be appreciated that the present invention covers compounds of formula (I) as the free base and as salts thereof, for example as a pharmaceutically acceptable salt thereof.

In one embodiment the invention relates to compounds of formula (I) or a pharmaceutically acceptable salt thereof.

Because of their potential use in medicine, salts of the compounds of formula (I) are desirably pharmaceutically acceptable. Suitable pharmaceutically acceptable salts can include acid or base addition salts. As used herein, the term 'pharmaceutically acceptable salt' means any pharmaceutically acceptable salt or solvate of a compound of the invention, which upon administration to the recipient is capable of providing (directly or indirectly). For a review on suitable salts see Berge et al., J. Pharm. Sci., 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable acid addition salt can be formed by reaction of a compound of formula (I) with a suitable inorganic or organic acid (such as hydrobromic, hydrochloric, sulphuric, nitric, phosphoric, succinc, maleic, acetic, propionic, fumaric, citric, tartaric, lactic, benzoic, salicylic, glutamaic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated for example by crystallisation and filtration. A pharmaceutically acceptable acid addition salt of a compound of formula (I) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

Other non-pharmaceutically acceptable salts, e.g. formates, oxalates or trifluoroacetates, may be used, for example in the isolation of the compounds of formula (I), and are included within the scope of this invention.

The invention includes within its scope all possible stoichiometric and non-stoichiometric forms of the salts of the compounds of formula (I).

It will be appreciated that many organic compounds can form complexes with solvents in which they are reacted or from which they are precipitated or crystallized. These complexes are known as "solvates". For example, a complex with water is known as a "hydrate". Solvents with high boiling points and/or capable of forming hydrogen bonds such as water, xylene, N-methylpyrrolidinone, methanol and ethanol may be used to form solvates. Methods for identification of solvates include, but are not limited to, NMR and microanalysis. Solvates of the compounds of formula (I) are within the scope of the invention.

The invention includes within its scope all possible stoichiometric and non-stoichiometric forms of the solvates of the compounds of formula (I).

The invention encompasses all prodrugs, of the compound of formula (I) or a pharmaceutically acceptable salt thereof, which upon administration to the recipient is capable of providing (directly or indirectly) the compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives.

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

Compounds described herein contain chiral atoms so that optical isomers, e.g. enantiomers or diastereoisomers may be formed. Accordingly, the present invention encompasses all isomers of the compounds of formula (I) whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Separation of isomers may be achieved by conventional techniques known to those skilled in the art, e.g. by fractional crystallisation, chromatography or HPLC.

Certain compounds of formula (I) may exist in one of several tautomeric forms. It will be understood that the present invention encompasses all tautomers of the compounds of formula (I) whether as individual tautomers or as mixtures thereof.

It will be appreciated from the foregoing that included within the scope of the invention are solvates, isomers and polymorphic forms of the compounds of formula (I) and salts thereof.

The compounds of formula (I) and salts thereof may be made by a variety of methods, including standard chemistry. Any previously defined variable will continue to have the previously defined meaning unless otherwise indicated. Illustrative general synthetic methods are set out below and then specific compounds of formula (I) or salts thereof are prepared in the working Examples.

The present invention further provides a process for the preparation of a compound of formula (I) or a salt thereof which comprises reacting a compound of formula (II)

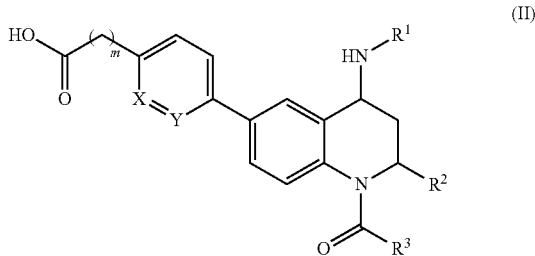

in which $R^1$, $R^2$, $R^3$, X, Y and m are as defined in formula (I) with a compound of formula (III) or a protected derivative thereof.

in which $R^5$ and $R^6$ are as defined in formula (I).

The reaction of the compounds of formula (I) and formula (II) may be carried out in a suitable organic solvent (e.g. DMF or acetonitrile) with an amine (e.g. DIPEA or triethylamine) in the presence of a suitable activating agent (e.g. HATU or TBTU).

Compounds of formula (II) can be prepared by methods described herein or by analogous methods. Compounds of formula (III) are either commercially available or can be prepared by methods described herein or by analogous procedures thereto.

It will be appreciated by those skilled in the art that it may be advantageous to protect one or more functional groups of the compounds described. Examples of protecting groups and the means for their removal can be found in T. W. Greene 'Protective Groups in Organic Synthesis' (4th edition, J. Wiley and Sons, 2006). Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—$COCF_3$) which may be removed by base catalysed hydrolysis.

It will be appreciated that in any of the routes described herein, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain intermediate compounds of formula (II) are believed to be novel and therefore form yet a further aspect of the invention.

The compounds of formula (I) and salts thereof are bromodomain inhibitors, and thus are believed to have potential utility in the treatment of diseases or conditions for which a bromodomain inhibitor is indicated.

The present invention thus provides a compound of formula (I) or a pharmaceutically acceptable salt thereof for use in therapy. The compound of formula (I) or pharmaceutically salt thereof can be used in the treatment of diseases or conditions for which a bromodomain inhibitor is indicated.

The present invention thus provides a compound of formula (I) or a pharmaceutically acceptable salt thereof for use in the treatment of any diseases or conditions for which a bromodomain inhibitor is indicated.

Also provided is the use of a compound of formula (I) or a pharmaceutically acceptable salt thereof in the manufacture of a medicament for the treatment of diseases or conditions for which a bromodomain inhibitor is indicated.

Also provided is a method of treating diseases or conditions for which a bromodomain inhibitor is indicated in a subject in need thereof which comprises administering a therapeutically effective amount of compound of formula (I) or a pharmaceutically acceptable salt thereof.

Suitably the subject in need thereof is a mammal, particularly a human.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of chronic autoimmune and/or inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, atherosclerosis, Alzheimer's disease, depression, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (kerartoconjunctivitis Sicca), vernal keratoconjunctivitis, atopic keratoconjunctivitis, anterior uveitis, pan uveitis, posterior uveits, uveitis-associated macula edema. scleritis, diabetic retinopathy, diabetic macula edema, age-related macula dystrophy, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors may be useful in the treatment of a wide variety of acute inflammatory conditions such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, asculitis with organ involvement and acute rejection of transplanted organs.

Bromodomain inhibitors may be useful in the prevention or treatment of diseases or conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus.

Bromodomain inhibitors may be useful in the prevention or treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of disorders of lipid metabolism via the regulation of APO-A1 such as hypercholesterolemia, atherosclerosis and Alzheimer's disease.

Bromodomain inhibitors may be useful in the treatment of fibrotic conditions such as idiopathic pulmonary fibrosis, renal fibrosis, post-operative stricture, keloid formation, scleroderma (including morphea) and cardiac fibrosis.

Bromodomain inhibitors may be useful in the prevention and treatment of viral infections such as herpes virus, human papilloma virus, adenovirus and poxvirus and other DNA viruses.

Bromodomain inhibitors may be useful in the treatment of cancer, including hematological (such as leukaemia, lymphoma and multiple myeloma), epithelial (including lung, breast and colon carcinomas), midline carcinomas, mesenchymal, hepatic, renal and neurological tumours.

Bromodomain inhibitors may be useful in the treatment of dermal pathology such as non-malignant melanoma (actinic keratosis and basal cell), in-situ melanoma, squamous cell carcinoma and cutaneous T-cell lymphoma.

In one embodiment the disease or condition for which a bromodomain inhibitor is indicated is selected from diseases associated with systemic inflammatory response syndrome, such as sepsis, burns, pancreatitis, major trauma, haemorrhage and ischaemia. In this embodiment the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac and gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock or endotoxaemia. In another embodiment, the bromodomain inhibitor is indicated for the treatment of acute or chronic pancreatitis. In another embodiment the bromodomain is indicated for the treatment of burns.

In one embodiment the disease or condition for which a bromodomain inhibitor is indicated is selected from herpes simplex infections and reactivations, cold sores, herpes zoster infections and reactivations, chickenpox, shingles, human papilloma virus, human immunodeficiency virus (HIV), cervical neoplasia, adenovirus infections, including acute respiratory disease, poxvirus infections such as cowpox and smallpox and African swine fever virus. In one particular embodiment a bromodomain inhibitor is indicated for the treatment of Human papilloma virus infections of skin or cervical epithelia.

The term "diseases or conditions for which a bromodomain inhibitor is indicated", is intended to include any of or all of the above disease states.

In one embodiment, there is provided a method for inhibiting a bromodomain which comprises contacting the bromodomain with a compound of formula (I) or a pharmaceutically acceptable salt thereof.

While it is possible that for use in therapy, a compound of formula (I) as well as pharmaceutically acceptable salts thereof may be administered as the raw chemical, it is common to present the active ingredient as a pharmaceutical composition.

The present invention therefore provides in a further aspect a pharmaceutical composition comprising a compound of formula (I) or a pharmaceutically acceptable salt and one or more pharmaceutically acceptable carriers, diluents or excipients. The compounds of the formula (I) and pharmaceutically acceptable salts, are as described above. The carrier(s), diluent(s) or excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of formula (I), or a pharmaceutically acceptable salt thereof, with one or more pharmaceutically acceptable carriers, diluents or excipients. The pharmaceutical composition can be for use in the treatment of any of the conditions described herein.

Since the compounds of formula (I) and pharmaceutically acceptable salts thereof are intended for use in pharmaceutical compositions it will be readily understood that they are each preferably provided in substantially pure form, for example, at least 60% pure, more suitably at least 75% pure and preferably at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral or sub-Tenon), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment the pharmaceutical composition is adapted for parenteral administration, particularly intravenous administration.

In one embodiment the pharmaceutical composition is adapted for oral administration.

In one embodiment the pharmaceutical composition is adapted for topical administration.

A preferred dosage form that results in occlusion and modification of skin permeation either to increase or decrease the systemic exposure of bromodomain compounds, including but not limited to the pharmaceutically acceptable forms of carboxymethylcellulose, an aliginate, gelatin, or polyvinyl pyrrolidone.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release as for example by coating or embedding particulate material in polymers, wax or the like.

The compounds of formula (I) and pharmaceutically acceptable salts thereof can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, emulsions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers. In one embodiment there is provided a pharmaceutical composition adapted for topical administration which comprises between 0.01-10%, or between 0.01-1% of the compound of formula (I), or a pharmaceutically acceptable salt thereof, by weight of the composition.

For treatments of the eye or other external tissues, for example mouth and skin, the compositions are preferably applied as a topical solution, suspension, emulsion, ointment, cream, gel spray or foam. When formulated in an ointment, the active ingredient may be employed with either a paraffinic or a water-miscible ointment base. Alternatively, the active ingredient may be formulated in a cream with an oil-in-water cream base or a water-in-oil. When formulated in a foam, the active agent may be formulated with propellants, surfactants, solvents, co-solvents and viscosity modifying agents.

Pharmaceutical compositions adapted for topical administrations to the eye include eye drops wherein the active ingredient is dissolved or suspended in a suitable carrier, especially an aqueous solvent. Compositions to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

An ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) Adv. Drug Deliv. Rev. 3; 57:1595-639, herein incorporated by reference for purposes of its teachings of examples of polymers for use in ocular drug delivery.

Dosage forms for nasal or inhaled administration may conveniently be formulated as aerosols, solutions, suspensions, gels or dry powders.

For compositions suitable and/or adapted for inhaled administration, it is preferred that the compound of formula (I) and pharmaceutically acceptable salts thereof are in a particle-size-reduced form e.g. obtained by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metals salts of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354.

A therapeutically effective amount of a compound of formula (I) or a pharmaceutically acceptable salt thereof will depend upon a number of factors including, for example, the age and weight of the animal, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 to 3000 mg, more preferably 0.5 to 1000 mg, of a compound of the invention calculated as the free base. Each dosage unit for nasal or inhaled administration preferably contains from 0.001 to 50 mg, more preferably 0.01 to 5 mg, of a compound of the formula (I) or a pharmaceutically acceptable salt thereof, calculated as the free base.

The pharmaceutically acceptable compounds of formula (I) or a pharmaceutically acceptable salt thereof can be administered in a daily dose (for an adult patient) of, for example, an oral or parenteral dose of 0.01 mg to 3000 mg per day or 0.5 to 1000 mg per day, or a nasal or inhaled dose of 0.001 to 50 mg per day or 0.01 to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of formula (I) and pharmaceutically acceptable salts thereof may be employed alone or in combination with other therapeutic agents. Combination therapies according to the present invention thus comprise the administration of at least one compound of formula (I) or a pharmaceutically acceptable salt thereof, and the use of at least one other pharmaceutically active agent. Preferably, combination therapies according to the present invention comprise the administration of at least one compound of formula (I) or a pharmaceutically acceptable salt thereof, and at least one other pharmaceutically active agent. The compound(s) of formula (I) and pharmaceutically acceptable salts thereof and the other pharmaceutically active agent(s) may be administered together in a single pharmaceutical composition or separately and, when administered separately this may occur simultaneously or sequentially in any order. The amounts of the compound(s) of formula (I) and pharmaceutically acceptable salts thereof and the other pharmaceutically active agent(s) and the relative timings of administration will be selected in order to achieve the desired combined therapeutic effect. Thus in a further aspect, there is provided a combination pharmaceutical product comprising a compound of formula (I) or a pharmaceutically acceptable salt thereof and at least one other pharmaceutically active agent.

Thus in one aspect, the compound of formula (I) or a pharmaceutically acceptable salt thereof and pharmaceutical compositions comprising a compound of formula (I) or a pharmaceutically acceptable salt thereof may be used in combination with or include one or more other therapeutic agents, for example selected from antibiotics, anti-virals, glucocorticosteroids, muscarinic antagonists, beta-2 agonists and vitamin D3 analogues. In a further aspect a compound of formula (I) or a pharmaceutically acceptable salt thereof, according to the invention may be used in combination with a further therapeutic agent which is suitable for the treatment of cancer.

It will be appreciated that when the compound of formula (I) or a pharmaceutically acceptable salt thereof is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The compounds of formula (I) and pharmaceutically acceptable salts thereof may be prepared by the methods described below or by similar methods. Thus the following Intermediates and Examples serve to illustrate the preparation of the compounds of formula (I) and pharmaceutically acceptable salts thereof, and are not to be considered as limiting the scope of the invention in any way.

GENERAL EXPERIMENTAL DETAILS

All temperatures referred to are in ° C.

The names of the following compounds have been obtained using the compound naming programme "ACD Name Pro 6.02" or Chem Draw Ultra 12.0.

Abbreviations

AcOH refers to acetic acid
BINAP refers to 2,2'-bis(diphenylphosphino)-1,1'-binaphthyl
BOC refers to tert-butoxycarbonyl
CV refers to column volumes
DCM refers to dichloromethane
1,2-DCE refers to 1,2-dichloroethane
DIPEA refers to diisopropylethylamine
DMSO refers to dimethylsulfoxide.
DMF refers to N,N-dimethylformamide
Ether refers to diethyl ether
$Et_2O$ refers to diethyl ether
EtOAc refers to ethyl acetate
FMOC refers to 9-fluorenylmethoxycarbonyl
HATU refers to O-(7-azabenzotriazol-1-yl)-N,N,N',N'-tetramethyluronium hexafluorophosphate
HPLC refers to high performance liquid chromatography
IPA refers to propan-2-ol
i-$Pr_2O$ refers to di-isopropyl ether
$LiAlH_4$ refers to lithium aluminium hydride
MDAP refers to Mass directed autoprep refers preparative mass directed HPLC
MeCN refers to acetonitrile
MeOH refers to methanol
$MgSO_4$ refers to magnesium sulfate
Mp refers to melting point
r.t. refers to room temperature
Rt refers to retention time
$Na_2SO_4$ refers to sodium sulphate
TBTU refers to O-(Benzotriazol-1-yl)-N,N,N',N'-tetramethyluronium tetrafluoroborate
TMEDA refers to tetramethylethylenediamine
TFA refers to trifluoroacetic acid
THF refers to tetrahydrofuran
TLC refers to thin layer chromatography
LCMS Methodology
Method Formate (Formic Acid Modifier)
LC Conditions The UPLC analysis was conducted on an Acquity UPLC BEH C18 column (50 mm×2.1 mm, i.d. 1.7 μm packing diameter) at 40° C.

The solvents employed were:
A=0.1% v/v solution of formic acid in water
B=0.1% v/v solution of formic acid in acetonitrile
The gradient employed was:

| Time (min) | Flow rate (ml/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 0 | 100 |

The UV detection was a summed signal from wavelength of 210 nm to 350 nm.
MS Conditions
  MS: Waters ZQ
  Ionisation mode: Alternate-scan positive and negative electrospray
  Scan range: 100 to 1000 AMU
  Scan time: 0.27 sec
  Inter scan delay: 0.10 sec
Method HpH (Ammonium Bicarbonate Modifier)
LC Conditions
  The UPLC analysis was conducted on an Acquity UPLC BEH C18 column (50 mm×2.1 mm, i.d. 1.7 μm packing diameter) at 40° C.
  The solvents employed were:
  A=10 mM ammonium hydrogen carbonate in water adjusted to pH10 with ammonia solution
  B=acetonitrile
  The gradient employed was:

| Time (min) | Flow rate (ml/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 0 | 100 |

The UV detection was a summed signal from wavelength of 210 nm to 350 nm.
MS Conditions
  MS: Waters ZQ
  Ionisation mode: Alternate-scan positive and negative electrospray
  Scan range: 100 to 1000 AMU
  Scan time: 0.27 sec
  Inter scan delay: 0.10 sec
MDAP Methodology
Method Formate (Formic Acid Modifier)
LC Conditions
  The HPLC analysis was conducted on either a Sunfire C18 column (100 mm×19 mm, i.d 5 μm packing diameter) or a Sunfire C18 column (150 mm×30 mm, i.d. 5 μm packing diameter) at ambient temperature.
  The solvents employed were:
  A=0.1% v/v solution of formic acid in water
  B=0.1% v/v solution of formic acid in acetonitrile
  Run as a gradient over either 15 or 25 min (extended run) with a flow rate of 20 ml/min (100 mm×19 mm, i.d 5 μm packing diameter) or 40 ml/min (150 mm×30 mm, i.d. 5 μm packing diameter).
  The UV detection was a summed signal from wavelength of 210 nm to 350 nm.
MS Conditions
  MS: Waters ZQ
  Ionisation mode: Alternate-scan positive and negative electrospray
  Scan range: 100 to 1000 AMU
  Scan time: 0.50 sec
  Inter scan delay: 0.20 sec
Method HpH (Ammonium Bicarbonate Modifier)
LC Conditions
  The HPLC analysis was conducted on either an Xbridge C18 column (100 mm×19 mm, i.d 5 μm packing diameter) or a Xbridge C18 column (100 mm×30 mm, i.d. 5 μm packing diameter) at ambient temperature.
  The solvents employed were:
  A=10 mM ammonium bicarbonate in water, adjusted to pH10 with ammonia solution
  B=acetonitrile
  Run as a gradient over either 15 or 25 min (extended run) with a flow rate of 20 ml/min (100 mm×19 mm, i.d 5 μm packing diameter) or 40 ml/min (100 mm×30 mm, i.d 5 μm packing diameter).
  The UV detection was a summed signal from wavelength of 210 nm to 350 nm.
MS Conditions
  MS: Waters ZQ
  Ionisation mode: Alternate-scan positive and negative electrospray
  Scan range: 100 to 1000 AMU
  Scan time: 0.50 sec
  Inter scan delay: 0.20 sec Intermediate 1

1-((2S,4R)-4-Amino-6-bromo-2-methyl-3,4-dihydroquinolin-1(2H)-yl)ethanone

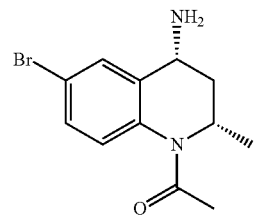 [SMILES: CC(=O)N1c2ccc(Br)cc2[C@H](N)C[C@@H]1C]

A suspension of aluminium chloride (41.2 g, 309 mmol) in DCM (480 mL) at 0° C. under nitrogen was treated with a solution of isopropyl ((2S,4R)-1-acetyl-6-bromo-2-methyl-1,2,3,4-tetrahydroquinolin-4-yl)carbamate (30 g, 81 mmol) in DCM (80 ml) via cannula and the resulting mixture was stirred at this temperature for 30 min. The reaction mixture was then slowly treated with a mixture of triethylamine (136 mL, 975 mmol) and MeOH (48 mL) via cannula. The resulting cake formed was stirred in EtOAc (800 mL), isolated by filtration and subsequently partitioned between DCM (800 mL) and saturated aqueous NaHCO$_3$ solution (800 mL). Sodium potassium tartrate (300 g) was added and the resulting mixture was stirred vigorously for 2 h. The layers were separated and the DCM layer was filtered through a sinter funnel. The filtrate was dried (MgSO$_4$) and concentrated in vacuo to give a first crop of 1-((2S,4R)-4-amino-6-bromo-2-methyl-3,4-dihydroquinolin-1(2H)-yl)ethanone (19.6 g, 69.2 mmol, 85% yield) as a yellow foam. The aqueous phase was treated further with DCM (800 mL) and the biphasic mixture stirred overnight. The layers were then separated and the organic layer was dried over (MgSO$_4$) and concentrated in vacuo to give a second crop of 1-((2S,4R)-4-amino-6-bromo- 2-methyl-3,4-dihydroquinolin-1(2H)-yl)ethanone (3.4 g, 12.01 mmol, 14.78% yield). LCMS (HpH, 2 min), Rt=0.77 min, MH+=283 (1 Br).

Intermediate 2

6-(((2S,4R)-1-Acetyl-6-bromo-2-methyl-1,2,3,4-tetrahydroquinolin-4-yl)amino)nicotinonitrile

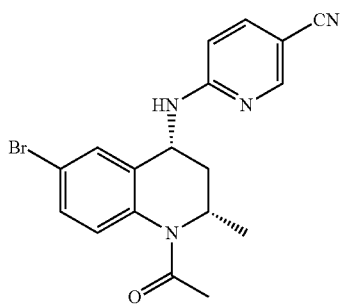 [SMILES: CC(=O)N1c2ccc(Br)cc2[C@H](Nc2ccc(C#N)cn2)C[C@@H]1C]

To a mixture of 1-((2S,4R)-4-amino-6-bromo-2-methyl-3,4-dihydroquinolin-1(2H)-yl)ethanone (for a preparation see Intermediate 1)(2.28 g, 8.05 mmol) and 6-chloronicotinonitrile (2.231 g, 16.10 mmol) was added NMP (20 mL) and the mixture treated with DIPEA (4.22 mL, 24.16 mmol). The mixture was split between 2 flasks and each flask was flushed with nitrogen, sealed and stirred under microwave irradiation at 200° C. for 2 h. The reaction mixtures were combined and partitioned between water and EtOAc. The aqueous layer was extracted with EtOAc (×4) and the combined organic layers were washed with water (×3), then brine and were dried (MgSO₄) filtered and concentrated in vacuo. The brown solid residue was purified by chromatography (EtOAc in Hexanes gradient) to give 6-(((2S,4R)-1-acetyl-6-bromo-2-methyl-1,2,3,4-tetrahydroquinolin-4-yl)amino)nicotinonitrile (1.940 g, 5.04 mmol, 62.5% yield) as a pale yellow foam. LCMS (HpH, 2 min), Rt=1.02 min, MH+=386 (1 Br).

Intermediate 3

Methyl 4-((2S,4R)-1-acetyl-4-((5-cyanopyridin-2-yl)amino)-2-methyl-1,2,3,4-tetrahydroquinolin-6-yl)benzoate

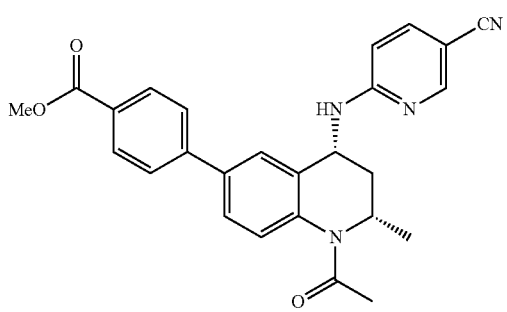 [SMILES: COC(=O)c1ccc(-c2ccc3c(c2)[C@H](Nc2ccc(C#N)cn2)C[C@H](C)N3C(C)=O)cc1]

To a flask charged with 6-(((2S,4R)-1-acetyl-6-bromo-2-methyl-1,2,3,4-tetrahydroquinolin-4-yl)amino)nicotinonitrile (for a preparation see Intermediate 2)(1000 mg, 2.60 mmol), (4-(methoxycarbonyl)phenyl)boronic acid (561 mg, 3.11 mmol), tetrakis(triphenylphosphine)palladium(0) (300 mg, 0.260 mmol) and potassium carbonate (1076 mg, 7.79 mmol) was added DME (20 mL) and water (4.0 mL). The resulting mixture was stirred at 100° C. under nitrogen for 1 h, then cooled to room temperature and concentrated in vacuo. The residue was partitioned between EtOAc and water and the layers were separated. The organic phase was dried (MgSO₄), concentrated in vacuo and the residue was purified by chromatography (10 g column, MeOH/DCM gradient) to give methyl 4-((2S,4R)-1-acetyl-4-((5-cyanopyridin-2-yl)amino)-2-methyl-1,2,3,4-tetrahydroquinolin-6-yl)benzoate (1002 mg, 2.275 mmol, 88% yield) as an orange foam. LCMS (HpH, 2 min), Rt=1.09 min, MH+=441.

Intermediate 4

4-((2S,4R)-1-Acetyl-4-((5-cyanopyridin-2-yl)amino)-2-methyl-1,2,3,4-tetrahydroquinolin-6-yl)benzoic acid

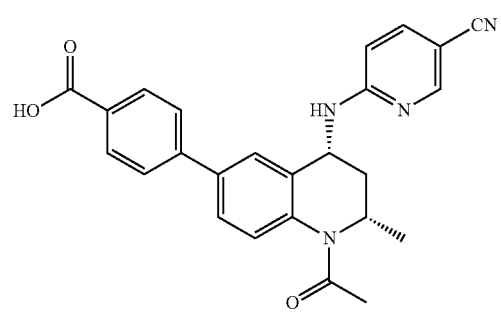

A solution of methyl 4-((2S,4R)-1-acetyl-4-((5-cyanopyridin-2-yl)amino)-2-methyl-1,2,3,4-tetrahydroquinolin-6-yl)benzoate (for a preparation see Intermediate 3) (1.0 g, 2.270 mmol) in MeOH (15 mL) at room temperature was treated with aqueous sodium hydroxide solution (2N, 2.27 mL, 4.54 mmol) and the resulting mixture was stirred at this temperature for 24 h. The bulk of MeOH was evaporated in vacuo and the aqueous residue was treated with acetic acid (0.39 mL, 6.81 mmol) giving precipitate which was isolated by filtration and dried under vacuum at 40° C. to afford 4-((2S,4R)-1-acetyl-4-((5-cyanopyridin-2-yl)amino)-2-methyl-1,2,3,4-tetrahydroquinolin-6-yl)benzoic acid (820 mg, 1.923 mmol, 85% yield) as a yellow solid. LCMS (HpH, 2 min), Rt=0.64 min, MH+=427.

Intermediate 5

6-(((2S,4R)-1-Acetyl-2-methyl-6-(4,4,5,5-tetramethyl-1,3,2-dioxaborolan-2-yl)-1,2,3,4-tetrahydroquinolin-4-yl)amino)nicotinonitrile

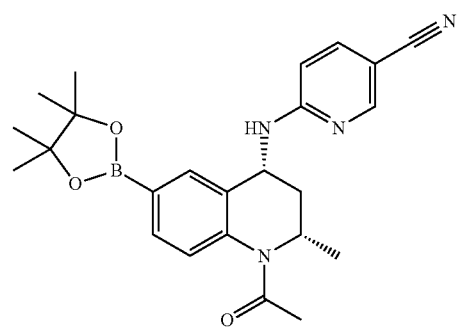 [SMILES: CC(=O)N1c2ccc(B3OC(C)(C)C(C)(C)O3)cc2[C@H](Nc2ccc(C#N)cn2)C[C@@H]1C]

To a flask charged with 6-(((2S,4R)-1-acetyl-6-bromo-2-methyl-1,2,3,4-tetrahydroquinolin-4-yl)amino)nicotinonitrile (for a preparation see Intermediate 2) (847 mg, 2.199 mmol), bis(pinacolato)diboron (1228 mg, 4.84 mmol), PdCl$_2$(dppf) (161 mg, 0.220 mmol) and potassium acetate (324 mg, 3.30 mmol) was added DMSO (7 mL), the mixture degassed under nitrogen and stirred under nitrogen for 1 h at 80° C. Further portions of bis(pinacolato)diboron (1 g), PdCl$_2$(dppf) (100 mg) and potassium acetate (150 mg) were added and the mixture was stirred for 45 min. Further portions of bis(pinacolato)diboron (1 g), PdCl$_2$(dppf) (100 mg) and potassium acetate (150 mg) was added and the mixture was stirred for 45 min. The reaction mixture was cooled to room temperature and treated with EtOAc and water. The biphasic mixture was filtered through a pad of Celite™ (10 g) and the layers were separated. The aqueous layer was extracted with EtOAc (×2) and the combined organic layers were washed with water (×4), then brine, dried (MgSO$_4$) and concentrated in vacuo. Purification of the residue by chromatography [50 g column, EtOAc/Hexanes gradient] afforded 6-(((2S,4R)-1-acetyl-2-methyl-6-(4,4,5,5-tetramethyl-1,3,2-dioxaborolan-2-yl)-1,2,3,4-tetrahydroquinolin-4-yl)amino)nicotinonitrile (800 mg, 1.850 mmol, 84% yield) as a red gum. LCMS (Formate, 2 min), Rt=1.08 min, MH+=433.

Intermediate 6

Methyl 6-((2S,4R)-1-acetyl-4-((5-cyanopyridin-2-yl)amino)-2-methyl-1,2,3,4-tetrahydroquinolin-6-yl)nicotinate

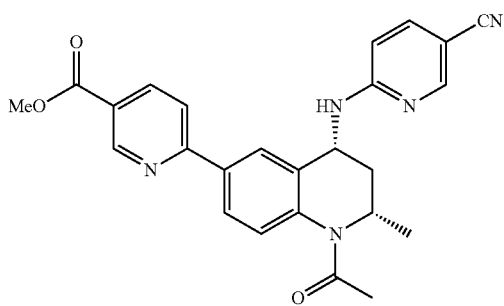 [SMILES: COC(=O)c1ccc(-c2ccc3c(c2)[C@H](Nc2ccc(C#N)cn2)C[C@H](C)N3C(C)=O)nc1]

To a flask charged with 6-(((2S,4R)-1-acetyl-2-methyl-6-(4,4,5,5-tetramethyl-1,3,2-dioxaborolan-2-yl)-1,2,3,4-tetrahydroquinolin-4-yl)amino)nicotinonitrile (for a preparation see Intermediate 5) (800 mg, 1.850 mmol), methyl 6-bromonicotinate (440 mg, 2.036 mmol), potassium carbonate (767 mg, 5.55 mmol) and tetrakis(triphenylphosphine)palladium(0) (214 mg, 0.185 mmol) were added toluene (8 mL) and ethanol (8 mL). The resulting mixture was stirred at 90° C. under nitrogen for 3 h at which point portions of potassium carbonate (384 mg) tetrakis(triphenylphosphine)palladium(0) (107 mg) and methyl 6-bromonicotinate (220 mg) were added and the reaction mixture stirring continued for 5 h. The mixture was then cooled to room temperature and concentrated in vacuo. The residue was partitioned between EtOAc and water. The phases were separated and the aqueous layer was extracted with EtOAc. The combined organic layers were washed with brine, dried (MgSO$_4$) and concentrated in vacuo. The residue was purified by chromatography [25 g column, EtOAc/Hexanes gradient] to give ethyl 6-((2S,4R)-1-acetyl-4-((5-cyanopyridin-2-yl)amino)-2-methyl-1,2,3,4-tetrahydroquinolin-6-yl)nicotinate (600 mg, 1.317 mmol, 71.2% yield) as a white foam. LCMS (HpH, 2 min), Rt=1.07 min, MH+=456.

Intermediate 7

6-((2S,4R)-1-Acetyl-4-((5-cyanopyridin-2-yl)amino)-2-methyl-1,2,3,4-tetrahydroquinolin-6-yl)nicotinic acid

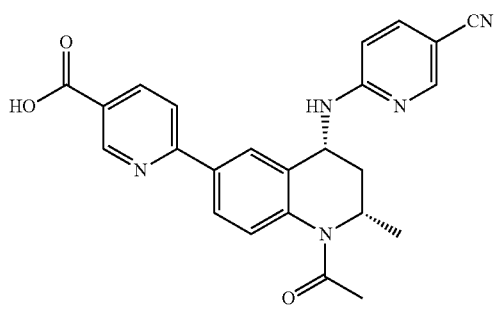 [SMILES: CC(=O)N1c2ccc(-c3ccc(C(=O)O)cn3)cc2[C@H](Nc2ccc(C#N)cn2)C[C@@H]1C]

A solution of methyl 6-((2S,4R)-1-acetyl-4-((5-cyanopyridin-2-yl)amino)-2-methyl-1,2,3,4-tetrahydroquinolin-6-yl)nicotinate (for a preparation see Intermediate 6) (580 mg, 1.273 mmol) in ethanol (10 mL) was treated with a aqueous lithium hydroxide solution (1N, 2.55 mL, 2.55 mmol) and the resulting mixture was stirred for 2 h. The bulk of ethanol was evaporated in vacuo and the residue was diluted with water (ca. 5 mL). The cloudy mixture was treated with acetic acid (0.146 mL, 2.55 mmol) and the precipitate formed was isolated by filtration, washed with Et$_2$O and dried at 60° C. for 16 h to give 6-((2S,4R)-1-acetyl-4-((5-cyanopyridin-2-yl)amino)-2-methyl-1,2,3,4-tetrahydroquinolin-6-yl)nicotinic acid (410 mg, 0.959 mmol, 75% yield) as a pale yellow solid which was used in the next step without further purification. LCMS (HpH, 2 min), Rt=0.63 min, MH+=428.

Intermediate 8

Ethyl 2-(4-((2S,4R)-1-acetyl-4-((5-cyanopyridin-2-yl)amino)-2-methyl-1,2,3,4-tetrahydroquinolin-6-yl)phenyl)acetate

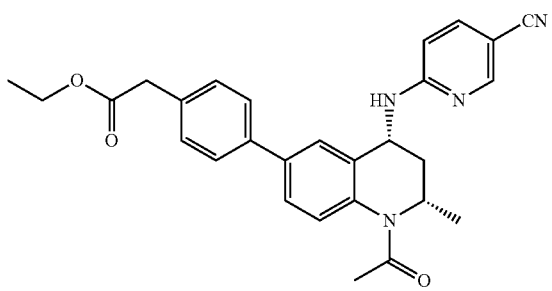 [SMILES: CCOC(=O)Cc1ccc(-c2ccc3c(c2)[C@H](Nc2ccc(C#N)cn2)C[C@H](C)N3C(C)=O)cc1]

To a solution of 6-(((2S,4R)-1-acetyl-2-methyl-6-(4,4,5,5-tetramethyl-1,3,2-dioxaborolan-2-yl)-1,2,3,4-tetrahydroquinolin-4-yl)amino)nicotinonitrile (for a preparation see Intermediate 5) (1.67 g, 3.86 mmol), ethyl 2-(4-bromophenyl)acetate (1.127 g, 4.64 mmol) and potassium carbonate (1.602 g, 11.59 mmol) in toluene (10 mL) and ethanol (10.0 mL) was added tetrakis(triphenylphosphine)palladium(0) (0.446 g, 0.386 mmol) under nitrogen. The reaction mixture heated at 100° C. for 1 h, then partitioned between EtOAc and water. The layers were separated and the aqueous phase was extracted with EtOAc (×3). The combined organic layers were washed with brine, dried (MgSO4), filtered and concentrated in vacuo. The residue was purified by flash chromatography on silica gel (25 g), eluting with an EtOAc/cyclohexane gradient (10 to 80%). The appropriate fractions were combined and concentrated in vacuo to give ethyl 2-(4-((2S,4R)-1-acetyl-4-((5-cyanopyridin-2-yl)amino)-2-methyl-1,2,3,4-tetrahydroquinolin-6-yl)phenyl)acetate (752 mg, 42%) as a viscous colourless oil. LCMS (Formate, 2 min), Rt=1.10 min, MH+=469.

Intermediate 9

2-(4-((2S,4R)-1-Acetyl-4-((5-cyanopyridin-2-yl) amino)-2-methyl-1,2,3,4-tetrahydroquinolin-6-yl) phenyl)acetic acid, lithium salt

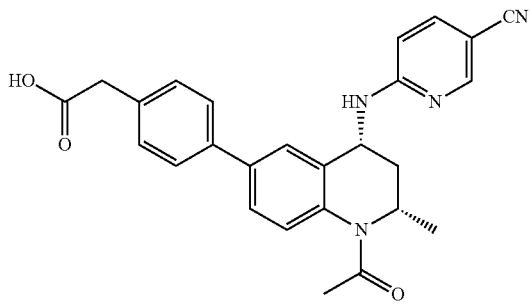 [SMILES: CC(=O)N1c2ccc(-c3ccc(CC(=O)O)cc3)cc2[C@H](Nc2ccc(C#N)cn2)C[C@@H]1C]

To a solution of ethyl 2-(4-((2S,4R)-1-acetyl-4-((5-cyanopyridin-2-yl)amino)-2-methyl-1,2,3,4-tetrahydroquinolin-6-yl)phenyl)acetate (for a preparation see Intermediate 8) (300 mg, 0.640 mmol) in MeOH (5 mL) was added lithium hydroxide solution (0.768 mL, 0.768 mmol). The resulting mixture was stirred at 40° C. for 2 h, whereupon it was concentrated under vacuum to give the crude lithium carboxylate of 2-(4-((2S,4R)-1-acetyl-4-((5-cyanopyridin-2-yl) amino)-2-methyl-1,2,3,4-tetrahydroquinolin-6-yl)phenyl) acetic acid (286 mg, 100%) as a white solid which was used in the next step without further purification. LCMS (Formate, 2 min), Rt=1.10 min, MH+=433.

Intermediate 10

3-(4-((2S,4R)-1-Acetyl-4-((5-cyanopyridin-2-yl) amino)-2-methyl-1,2,3,4-tetrahydroquinolin-6-yl) phenyl)propanoic acid

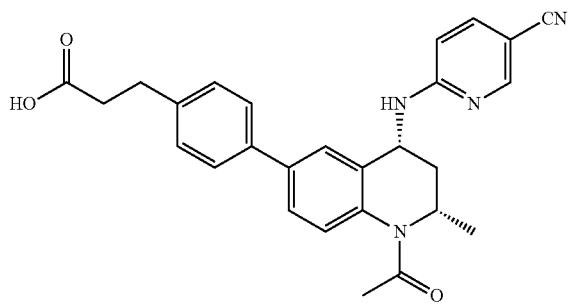 [SMILES: CC(=O)N1c2ccc(-c3ccc(CCC(=O)O)cc3)cc2[C@H](Nc2ccc(C#N)cn2)C[C@@H]1C]

To a solution of 6-(((2S,4R)-1-acetyl-2-methyl-6-(4,4,5,5-tetramethyl-1,3,2-dioxaborolan-2-yl)-1,2,3,4-tetrahydroquinolin-4-yl)amino)nicotinonitrile (for a preparation see Intermediate 5) (382 mg, 0.884 mmol) and 3-(4-bromophenyl)propanoic acid (243 mg, 1.060 mmol) in toluene (6 mL) and ethanol (6 mL) were successively added tetrakis(triphenylphosphine)palladium(0) (102 mg, 0.088 mmol) and potassium carbonate (366 mg, 2.65 mmol). The resulting mixture was stirred at 80° C. for 2 h, then partitioned between water and EtOAc. The layers were separated and the aqueous phase was extracted with EtOAc (×3). The combined organic layers were washed with brine, dried (MgSO4), filtered and concentrated in vacuo. The crude residue was purified by flash chromatography on silica gel (25 g), eluting with EtOAc in cyclohexane (10-70%). The appropriate fractions were combined and concentrated under reduced pressure to give 3-(4-((2S,4R)-1-acetyl-4-((5-cyanopyridin-2-yl)amino)-2-methyl-1,2,3,4-tetrahydroquinolin-6-yl)phenyl)propanoic acid (209 mg, 52%) as a white solid. LCMS (Formate, 2 min), Rt=0.91 min, MH+=455.

Intermediate 11

1-Methylethyl (2E)-2-butenoylcarbamate

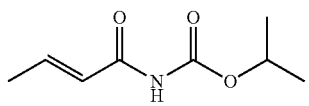

Isopropyl carbamate (30 g, 291 mmol, available from TCI) was charged to a 3 L Lara vessel and dry tetrahydrofuran (THF) (150 ml) added. (2E)-2-Butenoyl chloride (31.2 ml, 326 mmol, available from Aldrich) was added under nitrogen and the jacket cooled to −30° C. When the solution temperature reached −17° C. Lithium tert-butoxide (1M, 655 mL, 655 mmol) was added by peristaltic pump over 2 h, keeping the reaction temperature between −10° C. and −18° C. Once the addition was complete the mixture was stirred for 30 min and brought to 0° C. Diethyl ether (450 ml) and hydrochloric acid (1M, 375 mL) were added and the mixture brought to 20° C. with vigourous stirring. The stirring was stopped, the layers allowed to separate and the aqueous layer run off. Brine (375 mL) was added and the mixture stirred vigorously. The stirring was stopped, the layers allowed to separate and the aqueous layer run off. The organic layer was dried (MgSO4), filtered and evaporated to a brown oil (60 g). The was applied to a silica column (40+M Biotage) and eluted with DCM/EtOAc (1:1 to 0:1, 10CV). The product containing fractions were evaporated to dryness and loaded on to a Redisep Isco silica column (1500 g) and eluted with a EtOAc in cyclohexane gradient (0-40%). The clean, product containing fractions were evaporated to an off-white solid (15.41 g). LCMS (Method C): Rt=0.68, MH+=172

Intermediate 12

1-Methylethyl {(3S)-3-[(4-bromophenyl)amino] butanoyl}carbamate

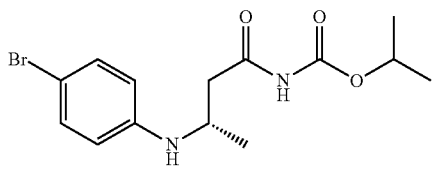 [SMILES: CC(C)OC(=O)NC(=O)C[C@H](C)Nc1ccc(Br)cc1]

1-Methylethyl (2E)-2-butenoylcarbamate (for a preparation see Intermediate 11)(9.38 g, 54.8 mmol) was stirred in toluene (281 mL) under nitrogen and (R-BINAP)ditriflatebis(acetonitrile)palladium(II) (for a preparation see Intermediate 36)(3.35 g, 3.01 mmol) added. The catalyst formed a gummy ball, the solution turned to an opaque yellow mixture and was stirred for 20 min. 4-Bromoaniline (14.14 g, 82 mmol) was added, the solution turned to a clear light brown and the gummy catalyst dissolved further. The mixture was stirred for 16 h. Similarly a second batch of 1-methylethyl (2E)-2-butenoylcarbamate (Intermediate 11, 8.51 g, 49.7 mmol) was stirred in toluene (255 mL) under nitrogen and (R-BINAP)ditriflatebis(acetonitrile)palladium(II) (3.04 g, 2.73 mmol) added. The catalyst formed a gummy ball, the solution turned to an opaque yellow mixture and was stirred for 20 min. 4-Bromoaniline (12.83 g, 74.6 mmol) was added, the solution turned to a clear light brown and the gummy catalyst dissolved further. The mixture was stirred for 16 h.

The two reaction mixtures were combined and loaded on to a 1.5 kg Isco silica Redisep column. The column was eluted with DCM/MeOH (0%→0.5%, 19 CV). The clean, product containing fractions were evaporated to a pale brown oil. The mixture was dried in a vacuum oven overnight at 40° C. to give 1-methylethyl {(3S)-3-[(4-bromophenyl)amino]butanoyl}carbamate as a white solid (24.2 g, 67% overall).

LCMS (Method C): Rt=0.91, MH+=343. ee=92%.

Intermediate 13

1-Methylethyl [(2S,4R)-6-bromo-2-methyl-1,2,3,4-tetrahydro-4-quinolinyl]carbamate

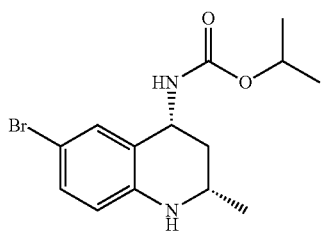 [SMILES: CC(C)OC(=O)N[C@@H]1C[C@H](C)Nc2ccc(Br)cc21]

1-Methylethyl {(3S)-3-[(4-bromophenyl)amino]butanoyl}carbamate (for a preparation see Intermediate 12) (17.9 g, 52.2 mmol) was taken up in ethanol (150 mL) and cooled to below −10° C. (internal temperature) in a CO₂/acetone bath. NaBH₄ (1.381 g, 36.5 mmol) was added followed by magnesium chloride hexahydrate (11.35 g, 55.8 mmol) in water (25 mL) keeping the temperature below −5° C. The mixture was allowed to stir at <0° C. for 1 h then warmed to room temperature and stirred for 1 h. The resulting thick suspension was poured into a mixture of citric acid (25.05 g, 130 mmol), HCl (1M in water, 205 mL, 205 mmol) and DCM (205 mL). The biphasic mixture was stirred at room temperature for 1 h. The layers were separated and the organic layer dried with Na₂SO₄, filtered and concentrated to yield the product as a light brown solid (14.1 g). LCMS (Method B): Rt=1.13, MH+=327

Intermediate 14

1-Methylethyl [(2S,4R)-1-acetyl-6-bromo-2-methyl-1,2,3,4-tetrahydro-4-quinolinyl]carbamate

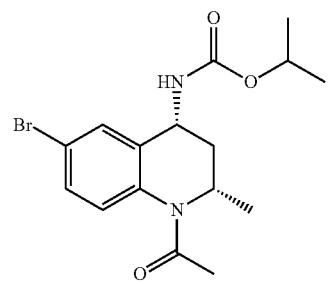 [SMILES: CC(=O)N1c2ccc(Br)cc2[C@H](NC(=O)OC(C)C)C[C@@H]1C]

1-Methylethyl [(2S,4R)-6-bromo-2-methyl-1,2,3,4-tetrahydro-4-quinolinyl]carbamate (for a preparation see Intermediate 13) (14.1 g, 43.1 mmol) was taken up in DCM (400 mL) under nitrogen at room temperature. Pyridine (10.46 mL, 129 mmol), then acetyl chloride (4.60 mL, 64.6 mmol), were added and the reaction stirred at room temperature for 16 h, then partitioned between EtOAc (2000 mL) and a saturated NaHCO₃ aqueous solution (800 mL). The layers were separated and the organic phase was washed with water then brine (1500 mL each) and then dried with Na₂SO₄ and concentrated in vacuo to yield a purple solid. The crude product was taken up in the minimum of DCM and applied to a 330 g Companion XL column and eluted with a gradient of 12-63% Ethyl Acetate in cyclohexane to give the product as an off-white solid (12.37 g).

LCMS (Method B): Rt=1.03, MH+=369

[alpha]D=+281.1025° (T=20.7° C., 10 mm cell, c=0.508 g/100 ml, ethanol).

Intermediate 15

Ethyl 4-[(2S,4R)-1-acetyl-2-methyl-4-({[(1-methylethyl)oxy]carbonyl}amino)-1,2,3,4-tetrahydro-6-quinolinyl]benzoate

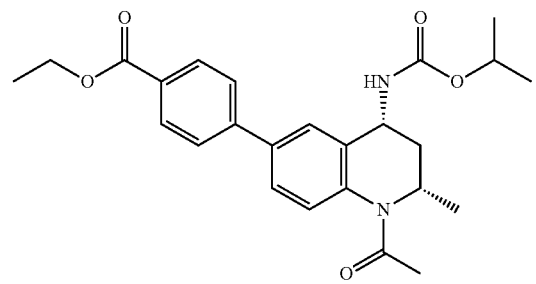 [SMILES: CCOC(=O)c1ccc(-c2ccc3c(c2)[C@H](NC(=O)OC(C)C)C[C@H](C)N3C(C)=O)cc1]

1-Methylethyl [(2S,4R)-1-acetyl-6-bromo-2-methyl-1,2,3,4-tetrahydro-4-quinolinyl]carbamate (for a preparation see Intermediate 14), (39.0 g, 106 mmol), {4-[(ethyloxy)carbonyl]phenyl}boronic acid (22.5 g, 116 mmol) and tetrakis(triphenylphosphine)palladium(0) (1.83 g, 1.58 mmol) were mixed in DME (430 mL) and the resulting mixture was treated with aqueous Na₂CO₃ (2N, 210 mL, 420 mmol). The mixture was degassed under house vacuum with several quenches with nitrogen and then stirred at 105° C. under nitrogen for approximately 6 h before being allowed to cool to room temperature. The mixture was partitioned between EtOAc and water and the layers were separated. The aqueous phase was extracted with EtOAc and the combined organic phases were washed with brine. The organic phase was then filtered through a 70 g silica cartridge, washing the cartridge with EtOAc. The combined filtrate and washings were concentrated in vacuo. The residue was triturated with Et₂O then filtered off. The solid obtained was air-dried to give ethyl 4-[(2S,4R)-1-acetyl-2-methyl-4-({[(1-methylethyl)oxy]carbonyl}amino)-1,2,3,4-tetrahydro-6-quinolinyl]benzoate (for a preparation see Intermediate 15) (35.2 g, 80.2 mmol, 76%) as a grey solid. The filtrate was concentrated in vacuo and the residue obtained triturated with Et₂O (approximately 30 mL). The solid formed was isolated by filtration and air-dried, to give ethyl 4-[(2S,4R)-1-acetyl-2-methyl-4-({[(1-methylethyl)oxy]carbonyl}amino)-1,2,3,4-tetrahydro-6-quinolinyl]benzoate as a grey solid (5.96 g, 13.5 mmol, 13%). LCMS (formate, 2 min), Retention time 1.16 min, MH+=439

Intermediate 16

Ethyl 4-[(2S,4R)-1-acetyl-4-amino-2-methyl-1,2,3,4-tetrahydro-6-quinolinyl]benzoate

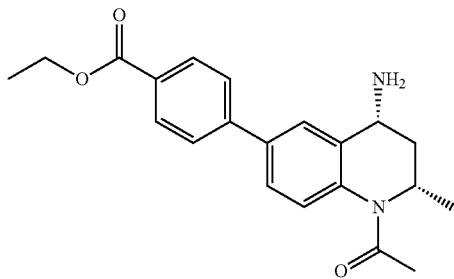 [SMILES: CCOC(=O)c1ccc(-c2ccc3c(c2)[C@H](N)C[C@H](C)N3C(C)=O)cc1]

Ethyl 4-[(2S,4R)-1-acetyl-2-methyl-4-({[(1-methylethyl)oxy]carbonyl}amino)-1,2,3,4-tetrahydro-6-quinolinyl]benzoate (for a preparation see intermediate 15) (8.90 g, 20.30 mmol) was added to a suspension of aluminium chloride (10.3 g, 77 mmol) in DCM (160 mL) cooled with an ice/water bath. The temperature rose from 0° C. to approximately 6° C. after the addition. The resulting mixture was stirred at approximately 0° C. for 20 min, and then treated with a solution of MeOH (18 mL) and triethylamine (34 mL, 245 mmol) over ~30 sec. The resulting mixture was stirred at 0° C. for ~30 min, and then partitioned between EtOAc and a saturated NaHCO₃ aqueous solution.

The same reaction was done in parallel, using of ethyl 4-[(2S,4R)-1-acetyl-2-methyl-4-({[(1-methylethyl)oxy]carbonyl}amino)-1,2,3,4-tetrahydro-6-quinolinyl]benzoate (for a preparation see Intermediate 15) (0.89 g 2.030 mmol), aluminium chloride (1.03 g, 7.72 mmol), triethylamine (3.4 mL, 24.53 mmol), DCM (16 mL) and MeOH (1.3 mL). The products of both reactions were combined at this stage and the resulting mixture was stirred at room temperature for approximately 10 min (total volume: approximately 1 L). The mixture was filtered through Celite™, the insoluble residue was washed with EtOAc and a saturated NaHCO₃ aqueous solution and the layers were separated. The aqueous phase was extracted with EtOAc and the combined organic phases were washed with brine, dried (hydrophobic frit) and concentrated in vacuo to give ethyl 4-[(2S,4R)-1-acetyl-4-amino-2-methyl-1,2,3,4-tetrahydro-6-quinolinyl]benzoate (6.6 g, 84%—allowing for the addition of the parallel experiment) as a cream solid. LCMS (formate, 2 min), Retention time 0.73 min, [M-NH₂]+=336

Intermediate 17

Ethyl 4-{(2S,4R)-1-acetyl-4-[(4-chlorophenyl)amino]-2-methyl-1,2,3,4-tetrahydro-6-quinolinyl}benzoate

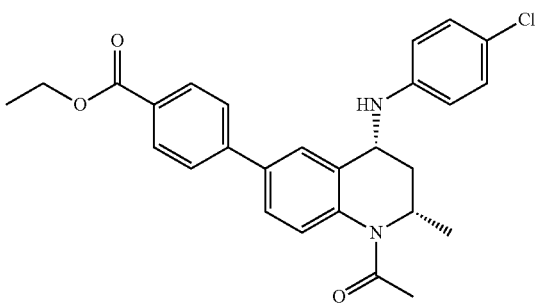 [SMILES: CCOC(=O)c1ccc(-c2ccc3c(c2)[C@H](Nc2ccc(Cl)cc2)C[C@H](C)N3C(C)=O)cc1]

Ethyl 4-[(2S,4R)-1-acetyl-4-amino-2-methyl-1,2,3,4-tetrahydro-6-quinolinyl]benzoate (for a preparation see Intermediate 16) (6.6 g, 18.73 mmol), 1-bromo-4-chlorobenzene (3.94 g, 20.60 mmol), bis(dibenzylideneacetone)palladium (0) (690 mg, 1.2 mmol) and [2'-(dicyclohexylphosphanyl)-2-biphenylyl]dimethylamine (Dave-phos) (590 mg, 1.499 mmol)) were mixed in toluene (120 mL) and the resulting mixture was treated with sodium t-butoxide (2.52 g, 26.2 mmol). The reaction was degassed under house vacuum with several quenches with nitrogen, heated at 70° C. under nitrogen for 16 h, then was allowed to cool to room temperature and filtered. The insoluble residue was washed with toluene and then Et₂O. The combined filtrate and washings were washed with water (×2) then extracted with hydrochloric acid (2N, ×20, resulting in the precipitation of an orange oil which was collected with the aqueous acidic phases. The acidic extracts were washed with Et₂O and the combined organic phases were washed with brine, dried (hydrophobic frit) and concentrated in vacuo. The residue was purified by chromatography on a silica cartridge (330 g), eluting with an EtOAc/cyclohexane gradient (5-45%). The appropriate fractions were combined and reduced to dryness in vacuo to give a pale yellow foam. This foam was dissolved in EtOAc (50 mL) and treated with functional thiourea silica (0.56 g, palladium scavenger). The mixture was stirred at room temperature (air atmosphere) for ~20 min and then left at room temperature for 16 h. The mixture was filtered and the insoluble residues washed with EtOAc. The combined filtrate and washings were concentrated in vacuo to give ethyl 4-{(2S,4R)-1- acetyl-4-[(4-chlorophenyl)amino]-2-methyl-1,2,3,4-tetrahydro-6-quinolinyl}benzoate (3.7 g, 8.0 mmol, 32%) as a yellow oil.

Intermediate 18

4-{(2S,4R)-1-Acetyl-4-[(4-chlorophenyl)amino]-2-methyl-1,2,3,4-tetrahydro-6-quinolinyl}benzoic acid

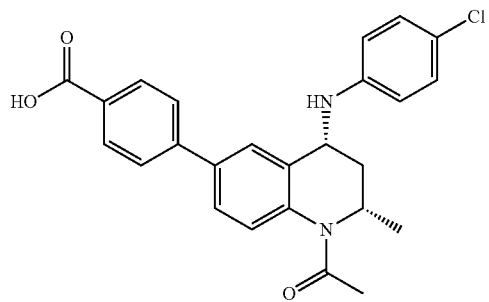 [SMILES: CC(=O)N1c2ccc(-c3ccc(C(=O)O)cc3)cc2[C@H](Nc2ccc(Cl)cc2)C[C@@H]1C]

Ethyl 4-{(2S,4R)-1-acetyl-4-[(4-chlorophenyl)amino]-2-methyl-1,2,3,4-tetrahydro-6-quinolinyl}benzoate (for a preparation see Intermediate 17) (5.41 g, 11.69 mmol) was dissolved in ethanol (100 mL) and the solution was treated with aqueous NaOH solution (2M, 50 mL, 100 mmol). The resulting mixture was stirred at room temperature (air atmosphere) for approximately 2 h then most of the ethanol was removed in vacuo. The resulting yellow solution was diluted with water (resulting in the formation of an oily yellow precipitate). The aqueous phase was washed twice with DCM (which didn't dissolve the precipitate previously formed) then was acidified with hydrochloric acid (2N) to pH 1 and extracted with EtOAc (×2). The combined EtOAc phases were washed with brine, dried (hydrophobic frit) and concentrated in vacuo. The residual yellow foam was triturated with Et$_2$O over approximately 1 h. The resulting solid was isolated by filtration, washed with Et$_2$O and air-dried to give 4-{(2S,4R)-1-acetyl-4-[(4-chlorophenyl)amino]-2-methyl-1,2,3,4-tetrahydro-6-quinolinyl}benzoic acid (4.41 g, 10.1 mmol, 87%) as a cream solid. LCMS (HpH), Retention time 1.08 min, [M−H]−=433

Intermediate 19

1-((2S,4R)-6-bromo-2-methyl-4-((5-nitropyridin-2-yl)amino)-3,4-dihydroquinolin-1(2H)-yl)ethanone

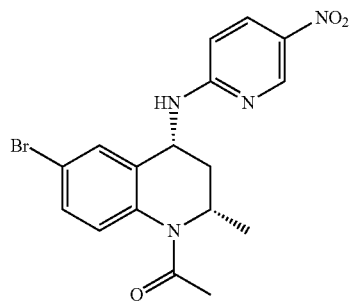 [SMILES: CC(=O)N1c2ccc(Br)cc2[C@H](Nc2ccc([N+](=O)[O-])cn2)C[C@@H]1C]

To a flask charged with 1-((2S,4R)-4-amino-6-bromo-2-methyl-3,4-dihydroquinolin-1(2H)-yl)ethanone (for a preparation see Intermediate 1)(2 g, 7.06 mmol) and 2-chloro-5-nitropyridine (2.240 g, 14.13 mmol) was added NMP (10 mL) and the resulting mixture treated with DIPEA (3.70 mL, 21.19 mmol). The mixture was divided between 2 flasks, each flask flushed with nitrogen, sealed and the mixture stirred under microwave irradiation at 200° C. for 2 h. The 2 reaction mixtures were combined, diluted with water and extracted with EtOAc (×4). Combined EtOAc layers were washed with water (×3) then brine, dried over MgSO$_4$ and concentrated in vacuo. The residual brown solid was purified by chromatography eluting with an EtOAc/hexanes gradient, which gave 1-((2S,4R)-6-bromo-2-methyl-4-((5-nitropyridin-2-yl)amino)-3,4-dihydroquinolin-1(2H)-yl)ethanone (4.6 g, 11.35 mmol, 161% yield) as a pale brown foam. LCMS (HpH, 2 min), Rt=1.08 min, MH+=405/407 (doublet).

Intermediate 20

Methyl 4-((2S,4R)-1-acetyl-2-methyl-4-((5-nitropyridin-2-yl)amino)-1,2,3,4-tetrahydroquinolin-6-yl)benzoate

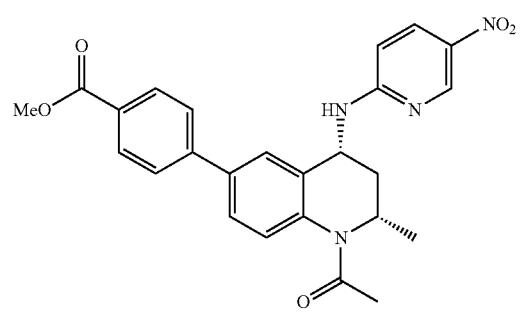

To a flask charged with (2S,4R)-1-acetyl-6-bromo-2-methyl-N-(5-nitro-2-pyridinyl)-1,2,3,4-tetrahydro-4-quinolinamine (for a preparation see Intermediate 19) (4.1 g, 10.12 mmol), {4-[(methyloxy)carbonyl]phenyl}boronic acid (2.185 g, 12.14 mmol), tetrakis(triphenylphosphine)palladium(0) (1.169 g, 1.012 mmol) and potassium carbonate (4.19 g, 30.4 mmol) was added DME (50 mL) and water (10.0 mL) and the resulting mixture was stirred at 100° C. under nitrogen for 1 h then cooled to room temperature and concentrated in vacuo. The residue was partitioned between EtOAc and water and the layers were separated. The organic phase was dried over MgSO4 and concentrated in vacuo. The residue was purified by chromatography eluting with an EtOAc/hexanes gradient, which gave methyl 4-((2S,4R)-1-acetyl-2-methyl-4-((5-nitropyridin-2-yl)amino)-1,2,3,4- tetrahydroquinolin-6-yl)benzoate (4.3 g, 9.34 mmol, 92% yield) as an orange foam, LCMS (HpH, 2 min), Rt=1.13 min, MH+=461.

Intermediate 21

Methyl 4-((2S,4R)-1-acetyl-4-((5-aminopyridin-2-yl)amino)-2-methyl-1,2,3,4-tetrahydroquinolin-6-yl)benzoate

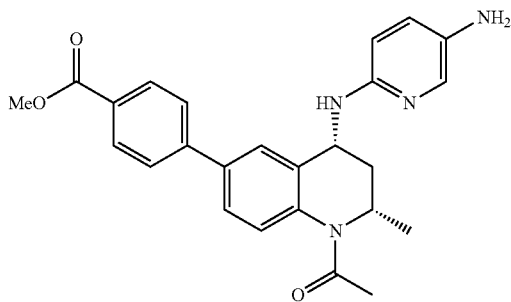 [SMILES: COC(=O)c1ccc(-c2ccc3c(c2)[C@H](Nc2ccc([N+](=O)[O-])cn2)C[C@H](C)N3C(C)=O)cc1]

To a flask charged with methyl 4-((2S,4R)-1-acetyl-2-methyl-4-((5-nitropyridin-2-yl)amino)-1,2,3,4-tetrahydroquinolin-6-yl)benzoate (for a preparation see Intermediate 20)(2.43 g, 5.28 mmol), ammonium formate (3.33 g, 52.8 mmol) and palladium on carbon (0.562 g, 5.28 mmol) was added MeOH (50 mL) and the resulting mixture was refluxed for 30 min. The reaction was cooled to room temperature, filtered through Celite™ and the residue washed with MeOH then DMF. The methanolic filtrate and washings were combined and concentrated in vacuo. The residue was dissolved in EtOAc, washed with brine, dried over MgSO4 and concentrated in vacuo. The residue was purified by chromatography eluting with a MeOH/DCM gradient to give methyl 4-((2S,4R)-1-acetyl-4-((5-aminopyridin-2-yl)amino)-2-methyl-1,2,3,4-tetrahydroquinolin-6-yl)benzoate (2.0 g, 4.65 mmol, 88% yield) as a dark pink foam. LCMS (HpH, 2 min), Rt=0.94 min, MH+=431.

Intermediate 22

Methyl 4-((2S,4R)-1-acetyl-2-methyl-4-(pyridin-2-ylamino)-1,2,3,4-tetrahydroquinolin-6-yl)benzoate

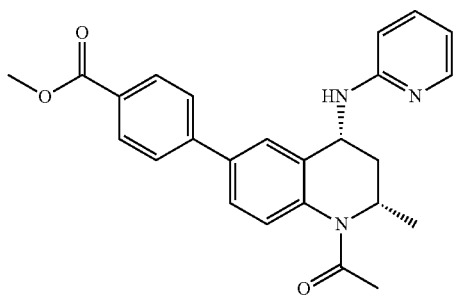 [SMILES: COC(=O)c1ccc(-c2ccc3c(c2)[C@H](Nc2ccccn2)C[C@H](C)N3C(C)=O)cc1]

A solution of methyl 4-((2S,4R)-1-acetyl-4-((5-aminopyridin-2-yl)amino)-2-methyl-1,2,3,4-tetrahydroquinolin-6-yl)benzoate (for a preparation see Intermediate 21) (1.04 g, 2.416 mmol) in ethanol (20 mL) at room temperature was treated with isoamyl nitrite (0.813 mL, 6.04 mmol) and the resulting mixture was stirred for 2 h at reflux then cooled to room temperature. Most of the solvent was removed in vacuo. The residue was treated with EtOAc and brine and both layers were passed through 10G of Celite™ then separated. The organic layer was dried over MgSO4 and concentrated in vacuo.

The residue was purified by chromatography, eluting with a MeOH/DCM gradient, which gave methyl 4-((2S,4R)-1-acetyl-2-methyl-4-(pyridin-2-ylamino)-1,2,3,4-tetrahydroquinolin-6-yl)benzoate (720 mg, 1.733 mmol, 71.7% yield) as a light pink foam. LCMS (HpH, 2 min), Rt=1.10 min, MH+=416.

Intermediate 23

4-((2S,4R)-1-acetyl-2-methyl-4-(pyridin-2-ylamino)-1,2,3,4-tetrahydroquinolin-6-yl)benzoic acid

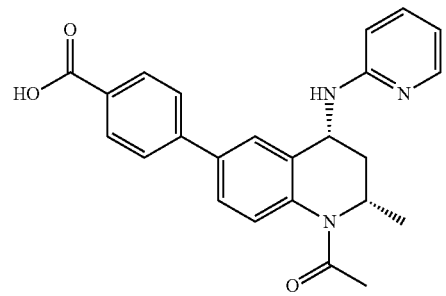

Methyl 4-((2S,4R)-1-acetyl-2-methyl-4-(pyridin-2-ylamino)-1,2,3,4-tetrahydroquinolin-6-yl)benzoate (for a preparation see Intermediate 22)(700 mg, 1.685 mmol) was dissolved in MeOH (10 ml) and sodium hydroxide solution (2M, 1.68 ml, 3.37 mmol) was added. After 6.5 h a further 2 equivalents of sodium hydroxide (2M, 1.685 ml) was added and reaction mixture stirred overnight. The was concentrated and the residue was diluted with water. Hydrochloric acid (2N, 1 ml) was added forming a precipitate which was isolated by filtration and dried to give 4-((2S,4R)-1-acetyl-2-methyl-4-(pyridin-2-ylamino)-1,2,3,4-tetrahydroquinolin-6-yl)benzoic acid (500 mg, 1.245 mmol, 73.9% yield) as a pinky solid. The aqueous phase was extracted EtOAc (×3) and the combined organic phases were dried over MgSO4 then concentrated in vacuo to give a further batch of 4-((2S,4R)-1-acetyl-2-methyl-4-(pyridin-2-ylamino)-1,2,3,4-tetrahydroquinolin-6-yl)benzoic acid (140 mg, 0.349 mmol, 20.70% yield) as a yellow foam. LCMS (HpH, 2 min), Rt=0.62 min, MH+=402.

Intermediate 24

1-((2S,4R)-2-methyl-4-((5-nitropyridin-2-yl)amino)-6-(4,4,5,5-tetramethyl-1,3,2-dioxaborolan-2-yl)-3,4-dihydroquinolin-1(2H)-yl)ethanone

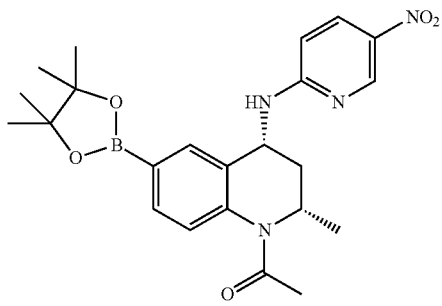 [SMILES: CC(=O)N1c2ccc(B3OC(C)(C)C(C)(C)O3)cc2[C@H](Nc2ccc([N+](=O)[O-])cn2)C[C@@H]1C]

To a flask charged with 1-((2S,4R)-6-bromo-2-methyl-4-((5-nitropyridin-2-yl)amino)-3,4-dihydroquinolin-1(2H)-yl)ethanone (for a preparation see Intermediate 19)(1.17 g, 2.89 mmol), bis(pinacolato)diboron (1.613 g, 6.35 mmol), PdCl$_2$(dppf) (0.211 g, 0.289 mmol) and potassium acetate (0.425 g, 4.33 mmol) was added DMSO (10 mL). The reaction mixture was degassed (under house vacuum over 10 min with several quenches with nitrogen) and stirred under nitrogen for 1.5 h at 80° C. The reaction was cooled to room temperature over 2 h, and diluted with EtOAc and water. The biphasic mixture was filtered through a pad of Celite™ (10 g) and the layers were separated. The aqueous layer was extracted with EtOAc (×2) and the combined organic phases were washed with water (×4) then brine, dried over MgSO$_4$ and concentrated in vacuo. The residue was purified by chromatography eluting with an EtOAc/Hexanes gradient; which gave 1-((2S,4R)-2-methyl-4-((5-nitropyridin-2-yl)amino)-6-(4,4,5,5-tetramethyl-1,3,2-dioxaborolan-2-yl)-3,4-dihydroquinolin-1(2H)-yl)ethanone (1.03 g, 2.277 mmol, 79% yield) as a light brown foam. LCMS (HpH, 2 min), Rt=1.15 min, MH+=453.

Intermediate 25 ethyl 6-((2S,4R)-1-acetyl-2-methyl-4-((5-nitropyridin-2-yl)amino)-1,2,3,4-tetrahydroquinolin-6-yl)nicotinate

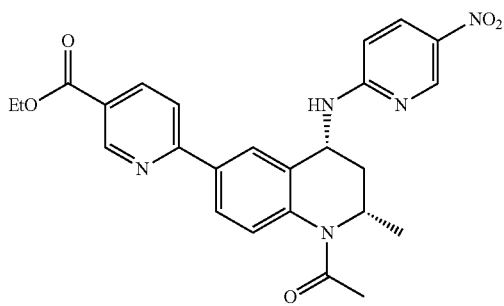

to a flask charged with 1-((2S,4R)-2-methyl-4-((5-nitropyridin-2-yl)amino)-6-(4,4,5,5-tetramethyl-1,3,2-dioxaborolan-2-yl)-3,4-dihydroquinolin-1(2H)-yl)ethanone (for a preparation see Intermediate 24)(1.03 g, 2.277 mmol), methyl 6-bromonicotinate (0.541 g, 2.505 mmol), potassium carbonate (0.944 g, 6.83 mmol) and tetrakis(triphenylphosphine) palladium (0) (0.263 g, 0.228 mmol) was added a previously degassed mixture of toluene (10 mL) and ethanol (10 mL). The resulting mixture was stirred at 90° C. under nitrogen. After 3 h, further portions of methyl 6-bromonicotinate (0.271 g, 1.252 mmol), potassium carbonate (0.472 g, 3.42 mmol) and tetrakis(triphenylphosphine)palladium (0) (0.132 g, 0.114 mmol) were added and reaction mixture heated for a further 4 h. The reaction was cooled to room temperature and concentrated in vacuo. The crude residue was partitioned between EtOAc and water, the phases separated and aqueous phase extracted with EtOAc. The combined organic phases were washed with brine, dried over MgSO$_4$ and concentrated in vacuo. Purification of the residue by chromatography, eluting with an EtOAc/hexanes gradient gave ethyl 6-((2S,4R)-1-acetyl-2-methyl-4-((5-nitropyridin-2-yl)amino)-1,2,3,4-tetrahydroquinolin-6-yl)nicotinate (740 mg, 1.556 mmol, 68.3% yield) as a yellow foam.

LCMS (HpH, 2 min), Rt=1.15 min, MH+=476.

Intermediate 26 ethyl 6-((2S,4R)-1-acetyl-4-((5-aminopyridin-2-yl)amino)-2-methyl-1,2,3,4-tetrahydroquinolin-6-yl)nicotinate

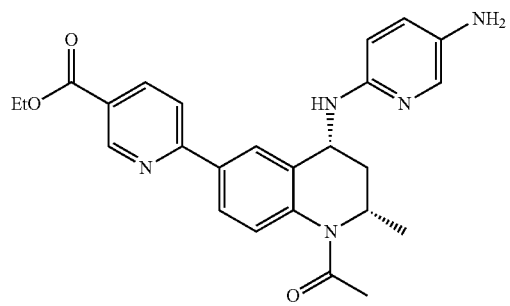 [SMILES: CCOC(=O)c1ccc(-c2ccc3c(c2)[C@H](Nc2ccc([N+](=O)[O-])cn2)C[C@H](C)N3C(C)=O)nc1]

To a flask charged with ethyl 6-((2S,4R)-1-acetyl-2-methyl-4-((5-nitropyridin-2-yl)amino)-1,2,3,4-tetrahydroquinolin-6-yl)nicotinate (for a preparation see Intermediate 25)(780 mg, 1.640 mmol), ammonium formate (1034 mg, 16.40 mmol) and palladium on carbon (10% Pd/C) (160 mg, 1.503 mmol) was added ethanol (15 ml) and the resulting mixture was refluxed for 45 min. The reaction was cooled to room temperature, filtered through Celite™, the residue washed with EtOH and the combined filtrate and washings concentrated in vacuo. The residue was dissolved in EtOAc, washed with brine, dried over MgSO$_4$ and concentrated in vacuo. The residue was purified by chromatography eluting with a MeOH/DCM gradient; which gave ethyl 6-((2S,4R)-1-acetyl-4-((5-aminopyridin-2-yl)amino)-2-methyl-1,2,3,4- tetrahydroquinolin-6-yl)nicotinate (450 mg, 1.010 mmol, 61.6% yield) as a pink foam. LCMS (HpH, 2 min), Rt=0.93 min, MH+=446.

Intermediate 27 ethyl 6-((2S,4R)-1-acetyl-2-methyl-4-(pyridin-2-ylamino)-1,2,3,4-tetrahydroquinolin-6-yl)nicotinate

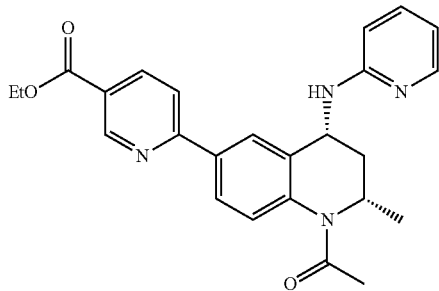 [SMILES: CC(=O)N1c2ccc(-c3ccc(C(=O)O)cn3)cc2[C@H](Nc2ccccn2)C[C@@H]1C]

A solution of ethyl 6-((2S,4R)-1-acetyl-4-((5-aminopyridin-2-yl)amino)-2-methyl-1,2,3,4-tetrahydroquinolin-6-yl)nicotinate (for a preparation see Intermediate 26)(450 mg, 1.010 mmol) in ethanol (10 mL) at room temperature was treated with isoamyl nitrite (0.34 mL, 2.53 mmol) and the resulting mixture was stirred 1 h at reflux then cooled to room temperature. Most of the solvent was evaporated in vacuo. The residue was treated with EtOAc and brine and both layers were filtered through Celite™ (10 g) then separated. The organic layer was dried over MgSO$_4$ and concentrated in vacuo.

The residue was purified by chromatography, eluting with a MeOH/DCM gradient; which gave ethyl 6-((2S,4R)-1-acetyl-2-methyl-4-(pyridin-2-ylamino)-1,2,3,4-tetrahydroquinolin-6-yl)nicotinate (240 mg, 0.557 mmol, 55.2% yield) as a light pink foam. LCMS (HpH, 2 min), Rt=1.09 min, MH+=431.

Intermediate 28

6-((2S,4R)-1-acetyl-2-methyl-4-(pyridin-2-ylamino)-1,2,3,4-tetrahydroquinolin-6-yl)nicotinic acid

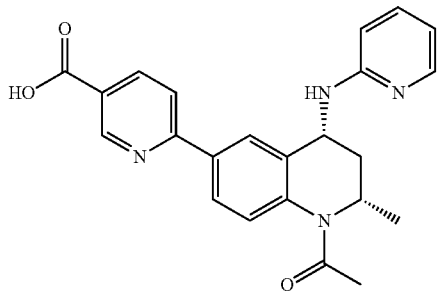

A solution of ethyl 6-((2S,4R)-1-acetyl-2-methyl-4-(pyridin-2-ylamino)-1,2,3,4-tetrahydroquinolin-6-yl)nicotinate (for a preparation see Intermediate 27)(240 mg, 0.557 mmol) in ethanol (5 mL) was treated with aqueous lithium hydroxide (1N, 1.115 mL, 1.115 mmol) and the resulting mixture was stirred at room temperature. After 1 h most of the ethanol was removed in vacuo, the residue was diluted with water (ca 2 mL) and the "cloudy" mixture was treated with acetic acid (0.064 mL, 1.115 mmol). The precipitate formed was isolated by filtration, washed with Et$_2$O and dried at 60° C. for 16 h to give 6-((2S,4R)-1-acetyl-2-methyl-4-(pyridin-2-ylamino)-1,2,3,4-tetrahydroquinolin-6-yl)nicotinic acid (150 mg, 0.373 mmol, 66.9% yield) as a pale yellow solid which was used in the next step without further purification. LCMS (HpH, 2 min), Rt=0.61 min, MH+=403.

Intermediate 29 tert-butyl ((2S,4R)-1-acetyl-6-bromo-2-methyl-1,2,3,4-tetrahydroquinolin-4-yl)carbamate

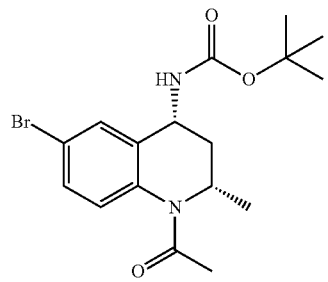 [SMILES: CC(=O)N1c2ccc(Br)cc2[C@H](NC(=O)OC(C)(C)C)C[C@@H]1C]

A solution of (2S,4R)-1-acetyl-6-bromo-2-methyl-1,2,3,4-tetrahydro-4-quinolinamine (11.3 g, 39.9 mmol) in DCM (120 mL) at room temperature was treated with triethylamine (16.69 mL, 120 mmol) then Boc$_2$O (12.97 mL, 55.9 mmol) and the resulting mixture was stirred at this temperature for 1 h. Further portions of base and anhydride (20%) were added further and after 30 min, the mixture was washed with saturated aqueous NaHCO$_3$ solution, dried (hydrophobic frit) and concentrated in vacuo. The residue was purified by chromatography, eluting with an EtOAc/hexane gradient; which gave tert-butyl ((2S,4R)-1-acetyl-6-bromo-2-methyl-1,2,3,4-tetrahydroquinolin-4-yl)carbamate (9.2 g, 24.00 mmol, 60.1% yield) as a white foam. LCMS (HpH, 2 min), Rt=1.14 min, MH+=383/385.

Intermediate 30 methyl 4-((2S,4R)-1-acetyl-4-((tert-butoxycarbonyl)amino)-2-methyl-1,2,3,4-tetrahydroquinolin-6-yl)benzoate

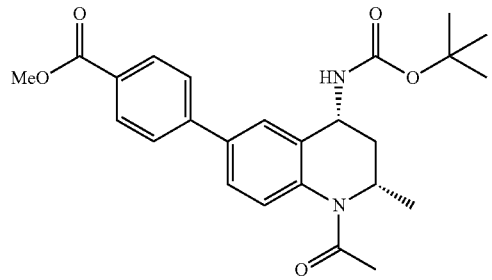 [SMILES: COC(=O)c1ccc(-c2ccc3c(c2)[C@H](NC(=O)OC(C)(C)C)C[C@H](C)N3C(C)=O)cc1]

To a flask charged with tert-butyl ((2S,4R)-1-acetyl-6-bromo-2-methyl-1,2,3,4-tetrahydroquinolin-4-yl)carbamate (for a preparation see Intermediate 29)(5 g, 13.05 mmol), (4-(methoxycarbonyl)phenyl)boronic acid (2.58 g, 14.35 mmol), tetrakis(triphenylphosphine)palladium (0) (1.507 g, 1.305 mmol) and potassium carbonate (5.41 g, 39.1 mmol) was added DME (50 mL) and water (10.0 mL) and the resulting mixture was stirred at 100° C. under nitrogen for 1 h. The reaction was cooled to room temperature and most of the DME was evaporated in vacuo. The residue was partitioned between EtOAc and water and the layers were separated. The aqueous phase was extracted with EtOAc and the combined organic phases were washed with brine, dried over MgSO₄ and concentrated in vacuo. the residue was purified by chromatography, eluting with an EtOAc/hexanes gradient; which gave methyl 4-((2S,4R)-1-acetyl-4-((tert-butoxycarbonyl)amino)-2-methyl-1,2,3,4-tetrahydroquinolin-6-yl)benzoate (5.35 g, 12.20 mmol, 94% yield) as a white foam. LCMS (HpH, 2 min), Rt=1.18 min, MH+=439.

Intermediate 31

4-((2S,4R)-1-acetyl-4-((tert-butoxycarbonyl)amino)-2-methyl-1,2,3,4-tetrahydroquinolin-6-yl)benzoic acid

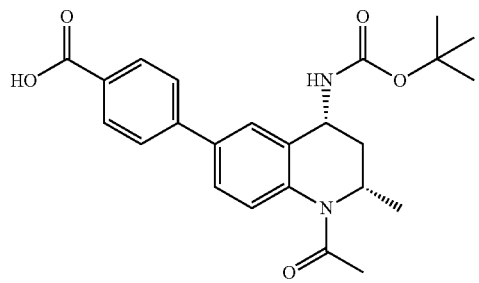

A solution of methyl 4-((2S,4R)-1-acetyl-4-((tert-butoxycarbonyl)amino)-2-methyl-1,2,3,4-tetrahydroquinolin-6-yl)benzoate (for a preparation see Intermediate 30)(5.23 g, 11.93 mmol) in MeOH (80 mL) was treated with aqueous lithium hydroxide (1M, 17.89 mL, 17.89 mmol) and the resulting mixture, which became a suspension after 5 min was stirred. After 24 h, lithium hydroxide (17.89 mL, 17.89 mmol) was added and the mixture (which by then was a solution) was stirred at 50° C. for 3 h. The mixture was cooled to room temperature, most of the MeOH was evaporated in vacuo and the residue treated with acetic acid (2.73 mL, 47.7 mmol). After 5 min, a precipitate formed, was isolated by filtration, washed with water and dried at 45° C. under vacuum for 16 h to give 4-((2S,4R)-1-acetyl-4-((tert-butoxycarbonyl)amino)-2-methyl-1,2,3,4-tetrahydroquinolin-6-yl)benzoic acid (4.88 g, 11.50 mmol, 96% yield) as a white solid. LCMS (HpH, 2 min), Rt=0.70 min, MH+=425.

Intermediate 32

4-((2S,4R)-1-acetyl-4-amino-2-methyl-1,2,3,4-tetrahydroquinolin-6-yl)-N-(2-(dimethylamino)ethyl)benzamide

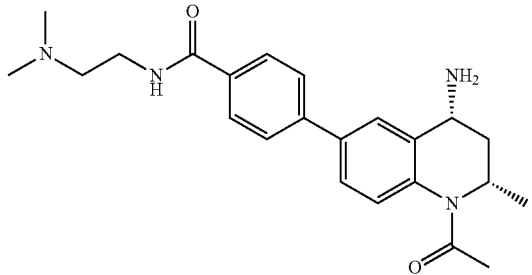

A suspension of crushed tert-butyl ((2S,4R)-1-acetyl-6-(4-((2-(dimethylamino)ethyl)carbamoyl)phenyl)-2-methyl-1,2,3,4-tetrahydroquinolin-4-yl)carbamate (for a preparation see Intermediate 41) (8 g, possibly as the PF6 salt) was treated with 1,4-dioxane (30 mL) followed by hydrogen chloride in 1,4-dioxane (4N, 40 mL, 160 mmol). After ~30 min most of the dioxane was removed and the residue dissolved in warm MeOH (100 mL) at 70° C. for 1.5 h. The residual insoluble material which was filtered off and discarded. The filtrate was concentrated in vacuo and purified using a SCX column (70 G, pre-conditioned with MeOH.) The cartridge was washed with MeOH (200 ml) and eluted with ammonia in MeOH (2M, 200 ml). The methanolic ammonia fractions were combined and concentrated in vacuo to give 4-((2S,4R)-1-acetyl-4-amino-2-methyl-1,2,3,4-tetrahydroquinolin-6-yl)-N-(2-(dimethylamino)ethyl)benzamide (3.65 g, 9.25 mmol, 84% yield) as a yellow foam. LCMS (HpH, 2 min), Rt=0.71 min, MH+=395.

Intermediate 33 methyl 5-((2S,4R)-1-acetyl-4-((5-cyanopyridin-2-yl)amino)-2-methyl-1,2,3,4-tetrahydroquinolin-6-yl)picolinate

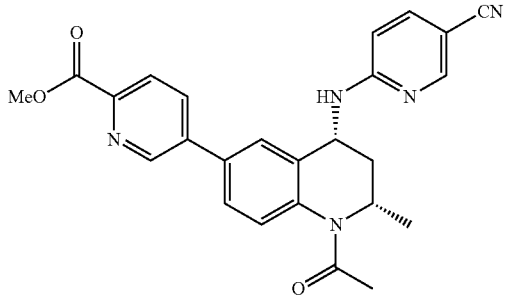

6-(((2S,4R)-1-Acetyl-6-bromo-2-methyl-1,2,3,4-tetrahydroquinolin-4-yl)amino)nicotinonitrile (for a preparation see Intermediate 2)(3.25 g, 8.44 mmol), {6-[(methyloxy)carbonyl]-3-pyridinyl}boronic acid (1.832 g, 10.12 mmol), {6-[(methyloxy)carbonyl]-3-pyridinyl}boronic acid (1.832 g, 10.12 mmol) and triethylamine (2.352 ml, 16.87 mmol) were combined in MeOH (30 ml) and DME (5 ml). The reaction mixture was divided between 2 vials and each heated at 120° C. for 45 min. The crude reaction mixtures were combined and concentrated in vacuo to give 4.4 g of crude brown solid. This was purified by chromatography on silica (100 g), eluting with over 1500 ml of EtOAc (compound leached off slowly) to give methyl 5-((2S,4R)-1-acetyl-4-((5-cyanopyridin-2-yl)amino)-2-methyl-1,2,3,4-tetrahydroquinolin-6-yl)picolinate (2.94 g, 6.66 mmol, 79% yield) as a brown foamy solid. LCMS (Formate, 2 min), Rt=0.81 min, MH+=442.

Intermediate 34

5-((2S,4R)-1-acetyl-4-((5-cyanopyridin-2-yl)amino)-2-methyl-1,2,3,4-tetrahydroquinolin-6-yl)picolinic acid

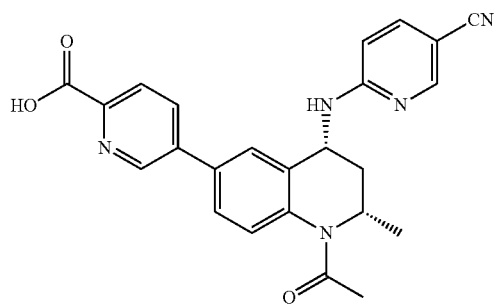 [SMILES: CC(=O)N1c2ccc(-c3ccc(C(=O)O)nc3)cc2[C@H](Nc2ccc(C#N)cn2)C[C@@H]1C]

Methyl 5-((2S,4R)-1-acetyl-4-((5-cyanopyridin-2-yl)amino)-2-methyl-1,2,3,4-tetrahydroquinolin-6-yl)picolinate (for a preparation see Intermediate 33)(2.94 g, 6.66 mmol) was dissolved in anhydrous 1,4-dioxane (20 ml). Water (20.0 ml) was added followed by lithium hydroxide (0.319 g, 13.32 mmol) and reaction mixture stirred at r.t. After 1 h, the 1,4-dioxane was removed in vacuo and aqueous residue was treated with acetic acid (1.144 ml, 19.98 mmol). The resulting orange precipitate was stirred for 20 min, isolated by filtration, washed with water and dried under vacuum overnight to give 5-((2S,4R)-1-acetyl-4-((5-cyanopyridin-2-yl)amino)-2-methyl-1,2,3,4-tetrahydroquinolin-6-yl)picolinic acid (2.16 g, 4.55 mmol, 68.3% yield) as a brown solid. LCMS (Formate, 2 min), Rt=0.68 min, MH+=428.

Intermediate 35

4-((2S,4R)-1-acetyl-2-methyl-4-(phenylamino)-1,2,3,4-tetrahydroquinolin-6-yl)benzoic acid

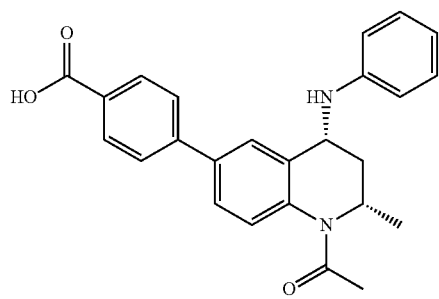 [SMILES: CC(=O)N1c2ccc(-c3ccc(C(=O)O)cc3)cc2[C@H](Nc2ccccc2)C[C@@H]1C]

Pd/C (22.1 mg, 10%, 0.208 mmol, containing ~50% water) was added to a solution of 4-((2S,4R)-1-acetyl-4-((4-chlorophenyl)amino)-2-methyl-1,2,3,4-tetrahydroquinolin-6-yl)benzoic acid (for a preparation see Intermediate 18)(369 mg, 0.848 mmol) and ammonium formate (134 mg, 2.121 mmol) in ethanol (5 ml) and DMF (1 ml) and reaction mixture heated at reflux. After 1.5 h the reaction mixture was cooled to r.t. The reaction mixture was filtered through Celite™ and filter cake washed with EtOH. The filtrate was concentrated to give a light brown oil (251 mg). The filter cake was washed with a further portion of 1:1 EtOH:DMF (50 ml) and combined with the previous material and concentrated to give 4-((2S,4R)-1-acetyl-2-methyl-4-(phenylamino)-1,2,3,4-tetrahydroquinolin-6-yl)benzoic acid (306 mg, 0.764 mmol, 90% yield) as a yellow solid. LCMS (Formate, 2 min), Rt=1.01 min, MH+=401.

Intermediate 36

R-BINAP)ditriflatebis(acetonitrile)palladium(II

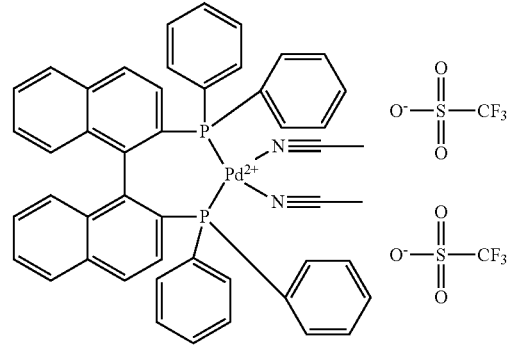

R-(+)-BINAP (6.08 g, 9.76 mmol, available from Avocado) was stirred in DCM (626 ml) and dichlorobis(acetonitrile)palladium (II) (2.5 g, 9.64 mmol, available from Aldrich) added. The mixture was stirred under nitrogen for 30 min, the suspension had not become a solution and more DCM (100 ml) was added. The mixture was stirred for a further 30 min and silver triflate (5.00 g, 19.47 mmol, available from Aldrich) dissolved in acetonitrile (250 ml) was added. The mixture changed from an orange cloudy suspension to a yellow suspension. The mixture was stirred for 1 h, filtered through Celite™ and evaporated to an orange solid. The residue was dried under vacuum (at approximately 14 mbar) at room temperature over the weekend to give the desired product (10.69 g).

1H NMR (400 MHz, MeCN-d3) δ ppm 2.0 (s, 6H), 6.7 (d, 2H), 6.9 (br m, 4H), 7.1 (br t, 2H), 7.2 (t, 2H), 7.5-7.9 (m, 22H)

Intermediate 37

1-Methylethyl {(2S,4R)-1-acetyl-6-[4-({[2-({[(1,1-dimethylethyl)oxy]carbonyl}amino)ethyl]amino}carbonyl)phenyl]-2-methyl-1,2,3,4-tetrahydro-4-quinolinyl}carbamate

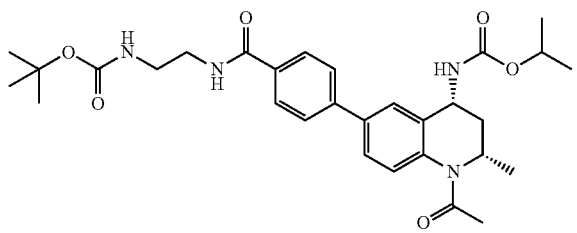 [SMILES: CC(=O)N1c2ccc(-c3ccc(C(=O)NCCNC(=O)OC(C)(C)C)cc3)cc2[C@H](NC(=O)OC(C)C)C[C@@H]1C]

To a flask charged with 4-((2S,4R)-1-acetyl-4-((isopropoxycarbonyl)amino)-2-methyl-1,2,3,4-tetrahydroquinolin-6-yl)benzoic acid (for a preparation see Intermediate 48) (82 mg, 0.2 mmol) and HATU (0.091 g, 0.240 mmol) was added DMF (2 mL) and the mixture treated with DIPEA (0.105 mL, 0.600 mmol) at room temperature. After 5 min, 1,1-dimethylethyl (2-aminoethyl)carbamate (0.047 mL, 0.300 mmol) was added and the mixture stirred at room temperature for 1 h. The reaction mixture was partitioned between EtOAc and water. The phases were separated and the aqueous phase was extracted with EtOAc. The combined organic layers were washed with brine, dried over MgSO₄, filtered and concentrated in vacuo. The residue was purified by chromatography eluting with a MeOH/DCM gradient to give 1-methylethyl {(2S,4R)-1-acetyl-6-[4-({[2-({[(1,1-dimethylethyl)oxy]carbonyl}amino)ethyl]amino}carbonyl)phenyl]-2-methyl-1,2,3,4-tetrahydro-4-quinolinyl}carbamate (95 mg, 0.172 mmol, 86% yield) as a pale brown foam. LCMS (HpH, 2 min), Rt=1.02 min, MH+=553.

Intermediate 38

1-Methylethyl {(2S,4R)-1-acetyl-6-[4-(2-{[2-({[(1,1-dimethylethyl)oxy]carbonyl}amino)ethyl]amino}-2-oxoethyl)phenyl]-2-methyl-1,2,3,4-tetrahydro-4-quinolinyl}carbamate

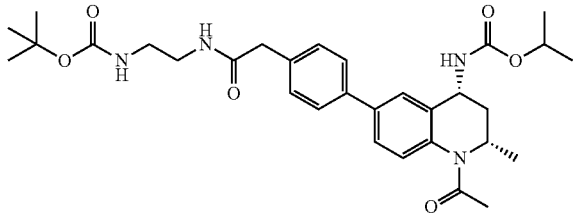 [SMILES: CC(=O)N1c2ccc(-c3ccc(CC(=O)NCCNC(=O)OC(C)(C)C)cc3)cc2[C@H](NC(=O)OC(C)C)C[C@@H]1C]

To a flask charged with 2-(4-((2S,4R)-1-acetyl-4-((isopropoxycarbonyl)amino)-2-methyl-1,2,3,4-tetrahydroquinolin-6-yl)phenyl)acetic acid (for a preparation see Intermediate 50) (85 mg, 0.2 mmol) and HATU (91 mg, 0.240 mmol) was added DMF (2 mL) and the mixture treated with DIPEA (0.105 mL, 0.600 mmol) at room temperature. After 5 min, 1,1-dimethylethyl (2-aminoethyl)carbamate (0.047 mL, 0.300 mmol) was added, the mixture was stirred at room temperature for 3 h and then partitioned between EtOAc and water. The phases were separated and the aqueous phase was extracted with EtOAc. The combined organic phases were washed with brine, dried over MgSO₄, filtered and concentrated in vacuo. the residue was purified by chromatography, eluting with a MeOH/DCM gradient, to give 1-methylethyl {(2S,4R)-1-acetyl-6-[4-(2-{[2-({[(1,1-dimethylethyl)oxy]carbonyl}amino)ethyl]amino}-2-oxoethyl)phenyl]-2-methyl-1,2,3,4-tetrahydro-4-quinolinyl}carbamate (56 mg, 0.099 mmol, 49.4% yield) as a pale yellow foam. LCMS (Formate, 2 min), Rt=0.91 min, MH+=455.

Intermediate 39 tert-Butyl (2-(4-((2S,4R)-1-acetyl-4-((5-cyanopyridin-2-yl)amino)-2-methyl-1,2,3,4-tetrahydroquinolin-6-yl)benzamido)ethyl)carbamate

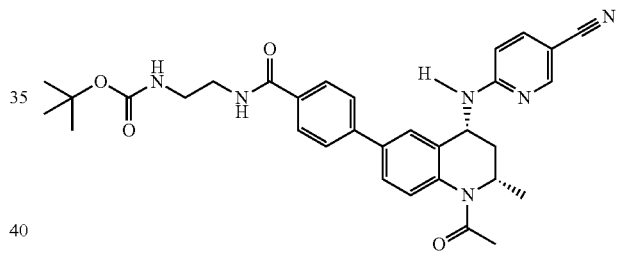

To a flask charged with 4-((2S,4R)-1-acetyl-4-((5-cyanopyridin-2-yl)amino)-2-methyl-1,2,3,4-tetrahydroquinolin-6-yl)benzoic acid (for a preparation see Intermediate 4)((70 mg, 0.164 mmol) and HATU (74.9 mg, 0.197 mmol) was added DMF (3 mL) and the resulting mixture was treated with DIPEA (0.086 mL, 0.492 mmol). After 5 min, tert-butyl (2-aminoethyl)carbamate (52.6 mg, 0.328 mmol) was added and the mixture was stirred at room temperature for 1 h and then concentrated in vacuo. The residue was partitioned between EtOAc and water and the layers were separated. The aqueous phase was extracted with EtOAc (×2) and the combined organic layers were washed with saturated aqueous NaHCO₃ (×3), then brine, dried over MgSO₄ and concentrated in vacuo to give tert-butyl (2-(4-((2S,4R)-1-acetyl-4-((5-cyanopyridin-2-yl)amino)-2-methyl-1,2,3,4-tetrahydroquinolin-6-yl)benzamido)ethyl)carbamate as a brown foam which was further purified by MDAP (HpH). to give tert-butyl (2-(4-((2S,4R)-1-acetyl-4-((5-cyanopyridin-2-yl)amino)-2-methyl-1,2,3,4-tetrahydroquinolin-6-yl)benzamido)ethyl)carbamate (65 mg, 0.114 mmol, 69.6% yield) as a white solid. LCMS (HpH, 2 min), Rt=1.00 min, MH+=569.

Intermediate 40 tert-butyl (2-(4-((2S,4R)-1-acetyl-2-methyl-4-(pyridin-2-ylamino)-1,2,3,4-tetrahydroquinolin-6-yl)benzamido)ethyl)carbamate

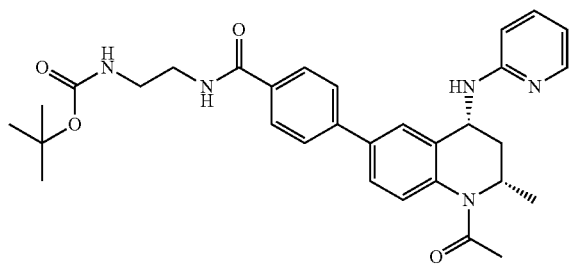 [SMILES: CC(=O)N1c2ccc(-c3ccc(C(=O)NCCNC(=O)OC(C)(C)C)cc3)cc2[C@H](Nc2ccccn2)C[C@@H]1C]

LCMS (High pH, 2 min), Rt=1.01 min, MH+=544

Intermediate 41 tert-butyl ((2S,4R)-1-acetyl-6-(4-((2-(dimethylamino)ethyl)carbamoyl)phenyl)-2-methyl-1,2,3,4-tetrahydroquinolin-4-yl)carbamate

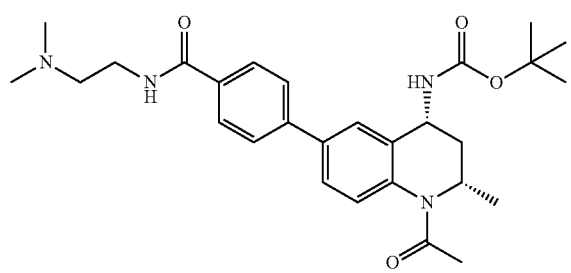 [SMILES: CC(=O)N1c2ccc(-c3ccc(C(=O)NCCN(C)C)cc3)cc2[C@H](NC(=O)OC(C)(C)C)C[C@@H]1C]

To a flask charged with 4-((2S,4R)-1-acetyl-4-((tert-butoxycarbonyl)amino)-2-methyl-1,2,3,4-tetrahydroquinolin-6-yl)benzoic acid (for a preparation see Intermediate 31) (4.88 g, 11.50 mmol) and HATU (5.25 g, 13.80 mmol) was added DMF (2 mL). The resulting mixture was treated with DIPEA (6.02 mL, 34.5 mmol) then after 5 min with N1,N1-dimethylethane-1,2-diamine (1.317 g, 14.95 mmol). After 0.5 h most of the DMF was removed in vacuo. The residue was treated with EtOAc and saturated NaHCO$_3$. Insoluble solid appeared which was isolated by filtration and dried under vacuum at 60° C. for 3 h to give tert-butyl ((2S,4R)-1-acetyl-6-(4-((2-(dimethylamino)ethyl)carbamoyl)phenyl)-2-methyl-1,2,3,4-tetrahydroquinolin-4-yl)carbamate as white solid (8.5 g), which was used without further purification in the subsequent reaction. The phases of the filtrate were separated, and the aqueous extracted with EtOAc (×2). The combined organic phases were washed with saturated NaHCO$_3$ (×3), dried over MgSO$_4$ and concentrated in vacuo to give a liquid (2.1 g). This liquid was loaded onto a SCX cartridge (50 g, pre-conditioned with MeOH) the cartridge washed with MeOH (200 ml) and eluted with ammonia in MeOH (2M, 200 ml). The methanolic ammonia fractions were combined and concentrated in vacuo to give a further portion of tert-butyl ((2S,4R)-1-acetyl-6-(4-((2-(dimethylamino)ethyl)carbamoyl)phenyl)-2-methyl-1,2,3,4-tetrahydroquinolin-4-yl)carbamate (0.3 g, 0.6 mmol, 5% yield) as an orange solid. LCMS (Formate, 2 min), Rt=0.94 min, MH+=495.

Intermediate 42 tert-butyl (1-(5-((2S,4R)-1-acetyl-4-((5-cyanopyridin-2-yl)amino)-2-methyl-1,2,3,4-tetrahydroquinolin-6-yl)picolinoyl)azetidin-3-yl)carbamate

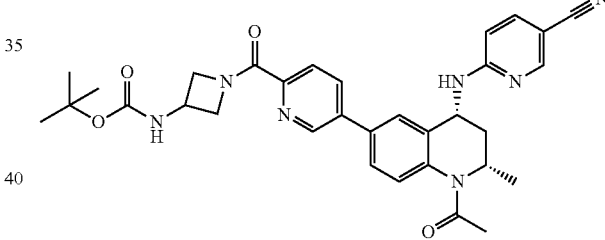

LCMS (Formate, 2 min), Rt=0.97 min, MH+=582

Intermediate 43 tert-butyl (1-(5-((2S,4R)-1-acetyl-4-((5-cyanopyridin-2-yl)amino)-2-methyl-1,2,3,4-tetrahydroquinolin-6-yl)picolinoyl)piperidin-4-yl)carbamate

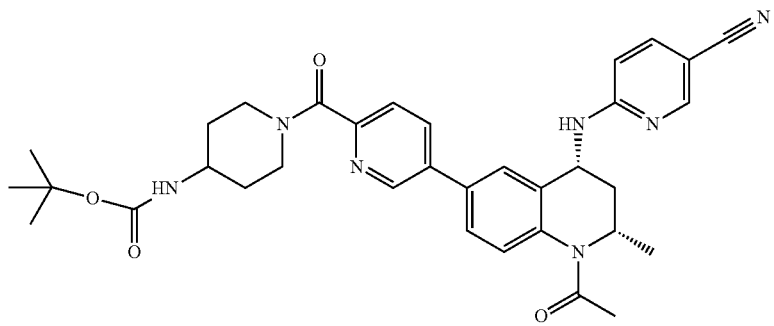 [SMILES: CC(=O)N1c2ccc(-c3ccc(C(=O)N4CCC(NC(=O)OC(C)(C)C)CC4)nc3)cc2[C@H](Nc2ccc(C#N)cn2)C[C@@H]1C]

LCMS (Formic, 2 min), Rt=0.97 min, MH+=610

Intermediate 44 tert-butyl 4-(5-((2S,4R)-1-acetyl-4-((5-cyanopyridin-2-yl)amino)-2-methyl-1,2,3,4-tetrahydroquinolin-6-yl)picolinoyl)piperazine-1-carboxylate

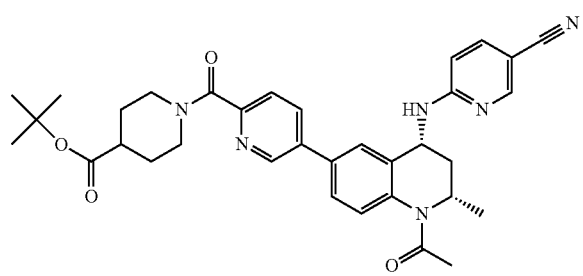 [SMILES: CC(=O)N1c2ccc(-c3ccc(C(=O)N4CCC(C(=O)OC(C)(C)C)CC4)nc3)cc2[C@H](Nc2ccc(C#N)cn2)C[C@@H]1C]

LCMS (Formate, 2 min), Rt=1.00 min, MH+=596

Intermediate 45 tert-butyl (2-(4-((2S,4R)-1-acetyl-4-((4-chlorophenyl)amino)-2-methyl-1,2,3,4-tetrahydroquinolin-6-yl)benzamido)ethyl)carbamate

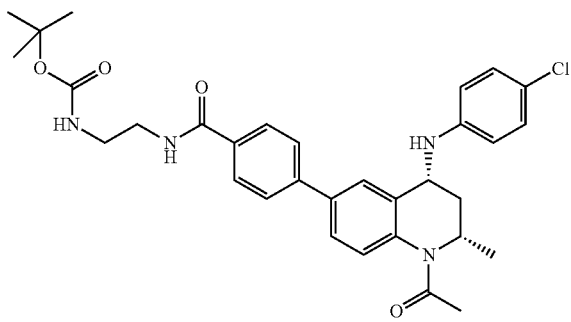 [SMILES: CC(=O)N1c2ccc(-c3ccc(C(=O)NCCNC(=O)OC(C)(C)C)cc3)cc2[C@H](Nc2ccc(Cl)cc2)C[C@@H]1C]

LCMS (High pH, 2 min), Rt=1.20 min, MH−=576

Intermediate 46

Methyl 4-((2S,4R)-1-acetyl-4-((isopropoxycarbonyl)amino)-2-methyl-1,2,3,4-tetrahydroquinolin-6-yl)benzoate

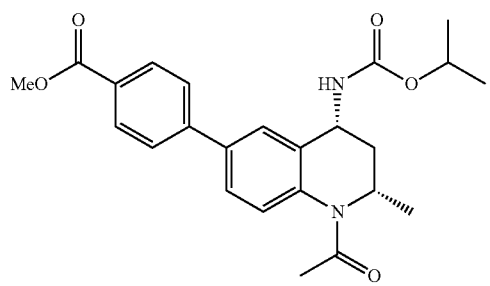 [SMILES: COC(=O)c1ccc(-c2ccc3c(c2)[C@H](NC(=O)OC(C)C)C[C@H](C)N3C(C)=O)cc1]

To a solution of isopropyl ((2S,4R)-1-acetyl-6-bromo-2-methyl-1,2,3,4-tetrahydroquinolin-4-yl)carbamate (5 g, 13.54 mmol) and methyl 4-(4,4,5,5-tetramethyl-1,3,2-dioxaborolan-2-yl)benzoate (3.90 g, 14.89 mmol) in DME (50 mL) and water (10.0 mL) were successively added palladium tetrakis(triphenylphosphine) (1.565 g, 1.354 mmol) and potassium carbonate (5.61 g, 40.6 mmol). The resulting mixture was stirred at 100° C. for 1 h, whereupon it was allowed to cool down to room temperature and was filtered through Celite™. The filtrated was concentrated in vacuo and the residue was partitioned between EtOAc and water. The aqueous phase was extracted with EtOAc (×3) and the combined organic layers were washed with brine, dried over MgSO₄, filtered and concentrated in vacuo. The crude compound was purified by flash chromatography on a silica gel cartridge (50 g) eluting with EtOAc in cyclohexane (5-60%). The appropriate fractions were combined and concentrated under reduced pressure to give methyl 4-((2S,4R)-1-acetyl-4-((isopropoxycarbonyl)amino)-2-methyl-1,2,3,4-tetrahydroquinolin-6-yl)benzoate (4.64 g, 81%) as a white gum. LCMS (Formate, 2 min), Rt=1.09 min, MH+=425.

Intermediate 47

Lithium 4-((2S,4R)-1-acetyl-4-((isopropoxycarbonyl)amino)-2-methyl-1,2,3,4-tetrahydroquinolin-6-yl)benzoate

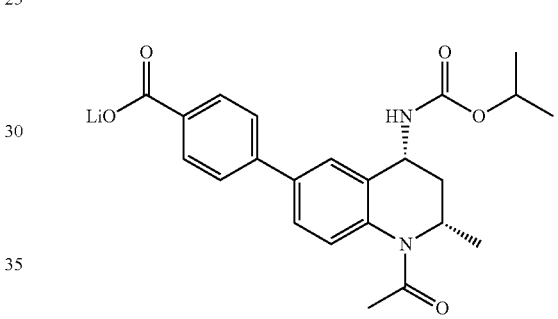

To a solution of methyl 4-((2S,4R)-1-acetyl-4-((isopropoxycarbonyl)amino)-2-methyl-1,2,3,4-tetrahydroquinolin-6-yl)benzoate (for a preparation see Intermediate 46)(1.63 g, 3.84 mmol) in MeOH (20 mL) was added lithium hydroxide (4.61 mL, 4.61 mmol). The resulting mixture was stirred at 40° C. for 6 h, whereupon it was concentrated under reduced pressure to give lithium 4-((2S,4R)-1-acetyl-4-((isopropoxycarbonyl)amino)-2-methyl-1,2,3,4-tetrahydroquinolin-6-yl)benzoate (1.65 g, 100%) which was not purified but directly used in the subsequent step. LCMS (Formate, 2 min), Rt=0.87 min, MH+=411.

Intermediate 48

4-((2S,4R)-1-Acetyl-4-((isopropoxycarbonyl)amino)-2-methyl-1,2,3,4-tetrahydroquinolin-6-yl)benzoic acid

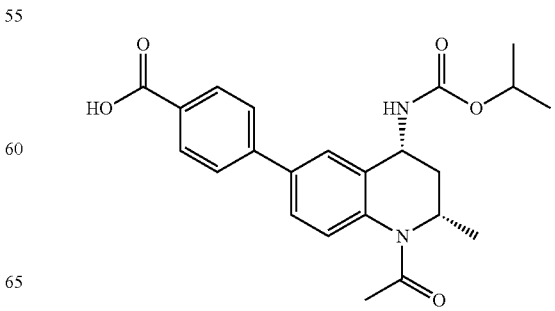

Lithium 4-((2S,4R)-1-acetyl-4-((isopropoxycarbonyl)amino)-2-methyl-1,2,3,4-tetrahydroquinolin-6-yl)benzoate (1.05 g, 2.52 mmol) (for a preparation see Intermediate 47) was partitioned between EtOAc and hydrochloric acid (2M). The phases were separated and the aqueous phase was extracted with EtOAc (×3). The combined organic layers were washed with brine, dried over MgSO₄, filtered and concentrated in vacuo to give 4-((2S,4R)-1-acetyl-4-((isopropoxycarbonyl)amino)-2-methyl-1,2,3,4-tetrahydroquinolin-6-yl)benzoic acid (898 mg, 87%) as a white solid. LCMS (Formate, 2 min), Rt=0.87 min, MH+=411.

Intermediate 49

Ethyl 2-(4-((2S,4R)-1-acetyl-4-((isopropoxycarbonyl)amino)-2-methyl-1,2,3,4-tetrahydroquinolin-6-yl)phenyl)acetate

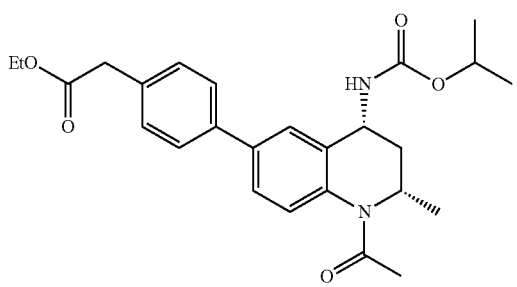 [SMILES: CCOC(=O)Cc1ccc(-c2ccc3c(c2)[C@H](NC(=O)OC(C)C)C[C@H](C)N3C(C)=O)cc1]

To a flask was charged with ethyl (4-bromophenyl)acetate (0.174 mL, 1.000 mmol), 1-methylethyl [(2S,4R)-1-acetyl-2-methyl-6-(4,4,5,5-tetramethyl-1,3,2-dioxaborolan-2-yl)-1,2,3,4-tetrahydro-4-quinolinyl]carbamate (416 mg, 1 mmol), potassium carbonate (415 mg, 3.00 mmol) and PdCl₂ (dppf) (73.2 mg, 0.100 mmol) was added 1,4-dioxane (6 mL) and water (2.0 mL) and the flask flushed with nitrogen. The resulting mixture was stirred under microwave irradiation at 120° C. for 30 min then cooled to room temperature. The bulk of dioxane was removed in vacuo and the residue partitioned between EtOAc and water. The layers were separated and the aqueous phase was extracted with EtOAc. The combined organic layers were washed with brine, dried over MgSO₄ and concentrated in vacuo. The residue was purified by chromatography [(25 g column, MeOH/DCM)] to give ethyl 2-(4-((2S,4R)-1-acetyl-4-((isopropoxycarbonyl)amino)-2-methyl-1,2,3,4-tetrahydroquinolin-6-yl)phenyl)acetate (270 mg, 59.7% yield). This compound was used in the next step without further purification. LCMS (HpH, 2 min), Rt=1.16, MH+=453.

Intermediate 50

2-(4-((2S,4R)-1-Acetyl-4-((isopropoxycarbonyl)amino)-2-methyl-1,2,3,4-tetrahydroquinolin-6-yl)phenyl)acetic acid

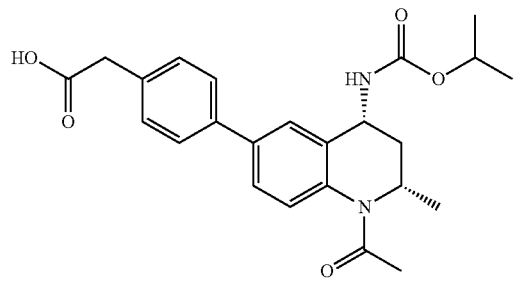 [SMILES: CC(=O)N1c2ccc(-c3ccc(CC(=O)O)cc3)cc2[C@H](NC(=O)OC(C)C)C[C@@H]1C]

To a solution of ethyl {4-[(2S,4R)-1-acetyl-2-methyl-4-({[(1-methylethyl)oxy]carbonyl}amino)-1,2,3,4-tetrahydro-6-quinolinyl]phenyl}acetate (for a preparation see Intermediate 49)(270 mg, 0.597 mmol) in MeOH (6 mL) and water (2.0 mL) was added aqueous sodium hydroxide (2N, 0.597 mL, 1.193 mmol) at room temperature and the resulting mixture was stirred for 6 h. Aqueous sodium hydroxide (2N, 0.5 mL) was added and the mixture was left standing overnight. The bulk of MeOH was removed in vacuo and the resulting residue was partitioned between water and Et₂O and the layers were separated. The aqueous layer was acidified with hydrochloric acid (2N, 2 mL) and extracted twice with EtOAc. The combined organic phases were dried over MgSO₄ and concentrated in vacuo to give {4-[(2S,4R)-1-acetyl-2-methyl-4-({[(1-methylethyl)oxy]carbonyl}amino)-1,2,3,4-tetrahydro-6-quinolinyl]phenyl}acetic acid (200 mg, 0.471 mmol, 79% yield) as a brown foam. This compound was used in the next step without further purification. LCMS (HpH, 2 min), Rt=0.65, MH+=425.

Intermediate 51

5-(((2S,4R)-1-acetyl-6-bromo-2-methyl-1,2,3,4-tetrahydroquinolin-4-yl)amino)pyrazine-2-carbonitrile

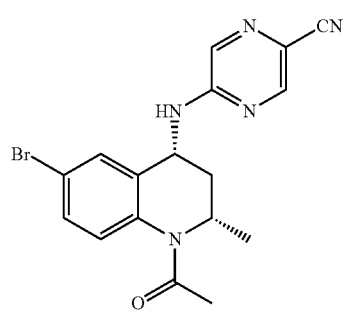 [SMILES: CC(=O)N1c2ccc(Br)cc2[C@H](Nc2cnc(C#N)cn2)C[C@@H]1C]

1-((2S,4R)-4-amino-6-bromo-2-methyl-3,4-dihydroquinolin-1(2H)-yl)ethanone (for a preparation, see Intermediate 1) (50 mg, 0.177 mmol), 5-chloropyrazine-2-carbonitrile (37.0 mg, 0.265 mmol) and DIPEA (0.123 mL, 0.706 mmol) were combined in NMP (1.5 mL) and heated in a sealed flask under microwave irradiation to 200° C. for 1 h. The mixture was partitioned between water (150 mL) and EtOAc (4×100 mL). The organic layers were combined, washed with brine (2×100 mL), dried by passing through a hydrophobic frit, and concentrated in vacuo. The resulting residue was purified by chromatography (25 g column, EtOAc/cyclohexane gradient) to give 5-(((2S,4R)-1-acetyl-6-bromo-2-methyl-1,2,3,4-tetrahydroquinolin-4-yl)amino)pyrazine-2-carbonitrile (61 mg, 0.158 mmol, 89% yield) as a brown gum.

LCMS (Formate, 2 min), Rt=0.94 mins, MH+=386/388.

Intermediate 52

Methyl 5-((2S,4R)-1-acetyl-4-((5-cyanopyrazin-2-yl)amino)-2-methyl-1,2,3,4-tetrahydroquinolin-6-yl)picolinate

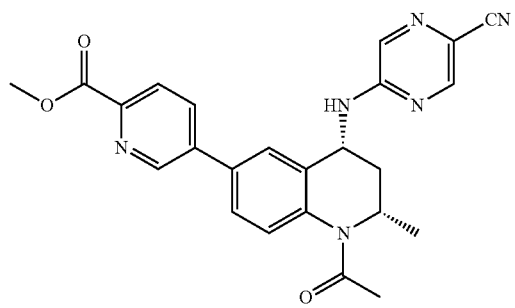 [SMILES: COC(=O)c1ccc(-c2ccc3c(c2)[C@H](Nc2cnc(C#N)cn2)C[C@H](C)N3C(C)=O)cn1]

5-(((2S,4R)-1-acetyl-6-bromo-2-methyl-1,2,3,4-tetrahydroquinolin-4-yl)amino)pyrazine-2-carbonitrile (for a preparation, see Intermediate 51) (390 mg, 1.010 mmol), (6-(methoxycarbonyl)pyridin-3-yl)boronic acid (219 mg, 1.21 mmol), PdCl$_2$(dppf) (111 mg, 0.151 mmol) and triethylamine (0.281 ml, 2.02 mmol) were combined in a mixture of dry MeOH (6 mL) and DME (1 mL). The mixture was heated under microwave irradiation to 120° C. for 45 mins. The mixture was then concentrated in vacuo and the residue purified by chromatography (100 g column, EtOAc/cyclohexane gradient) to give methyl 5-((2S,4R)-1-acetyl-4-((5-cyanopyrazin-2-yl)amino)-2-methyl-1,2,3,4-tetrahydroquinolin-6-yl)picolinate (389 mg, 0.879 mmol, 87% yield) as a pink solid.

LCMS: (Formate, 2 min), Rt=0.84 mins, MH+=443.

Intermediate 53

5-((2S,4R)-1-acetyl-4-((5-cyanopyrazin-2-yl)amino)-2-methyl-1,2,3,4-tetrahydroquinolin-6-yl)picolinic acid

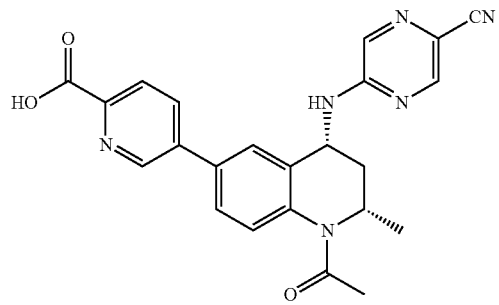

Lithium hydroxide monohydrate (83 mg, 1.97 mmol) in water (5 mL) was added to methyl 5-((2S,4R)-1-acetyl-4-((5-cyanopyrazin-2-yl)amino)-2-methyl-1,2,3,4-tetrahydroquinolin-6-yl)picolinate (for a preparation, see Intermediate 52) (435 mg, 0.983 mmol) in 1,4-dioxane (5 mL) and the reaction mixture stirred at room temperature for 70 mins. Acetic acid (0.169 mL, 2.95 mmol) was added and the resulting mixture stirred for 10 mins. The mixture was filtered, the solid collected was washed with water, then dried in a vacuum oven to give 5-((2S,4R)-1-acetyl-4-((5-cyanopyrazin-2-yl)amino)-2-methyl-1,2,3,4-tetrahydroquinolin-6-yl)picolinic acid (181 mg, 0.422 mmol, 43% yield) as a brown solid.

LCMS: (Formate, 2 min) Rt=0.66 mins, MH+=429.

Intermediate 54

Methyl 5-((2S,4R)-1-acetyl-4-amino-2-methyl-1,2,3,4-tetrahydroquinolin-6-yl)picolinate

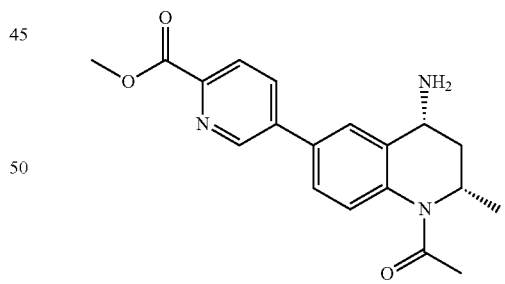

(2S,4R)-1-acetyl-6-bromo-2-methyl-1,2,3,4-tetrahydro-4-quinolinamine (for a preparation, see Intermediate 1) (600 mg, 1.88 mmol), methyl 5-(4,4,5,5-tetramethyl-1,3,2-dioxaborolan-2-yl)picolinate (593 mg, 2.25 mmol), PdCl$_2$(dppf) (206 mg, 0.282 mmol) and triethylamine (0.785 mL, 5.63 mmol) were combined in DME (3 mL) and MeOH (12 mL) and the mixture heated under microwave irradiation to 110° C. for 45 mins.

In a separate vial, (2S,4R)-1-acetyl-6-bromo-2-methyl-1,2,3,4-tetrahydro-4-quinolinamine (for a preparation, see Intermediate 1) (50 mg, 0.156 mmol), methyl 5-(4,4,5,5- tetramethyl-1,3,2-dioxaborolan-2-yl)picolinate (49.4 mg, 0.188 mmol), PdCl₂(dppf) (17.17 mg, 0.023 mmol) and triethylamine (0.065 mL, 0.469 mmol) were combined in DME (0.5 mL) and MeOH (1 mL) and the mixture heated under microwave irradiation to 110° C. for 45 mins. The two crude reaction mixtures were combined and concentrated in vacuo. The residue was purified by chromatography (100 g column, EtOAc/cyclohexane followed by 2M methanolic ammonia/DCM gradient). The appropriate fractions were combined, concentrated in vacuo and dried in a vacuum oven to give a residue. This residue was partitioned between sat. aq. sodium bicarbonate (100 mL) and DCM (3×100 mL). The organic layers were combined, dried by passing through a hydrophobic frit and concentrated in vacuo to give methyl 5-((2S,4R)-1-acetyl-4-amino-2-methyl-1,2,3,4-tetrahydroquinolin-6-yl)picolinate (555 mg, 1.64 mmol, 87% yield).

LCMS: (Formate, 2 min), Rt=0.53 mins, MH+=340.

Intermediate 55

5-((2S,4R)-1-acetyl-4-amino-2-methyl-1,2,3,4-tetrahydroquinolin-6-yl)picolinic acid

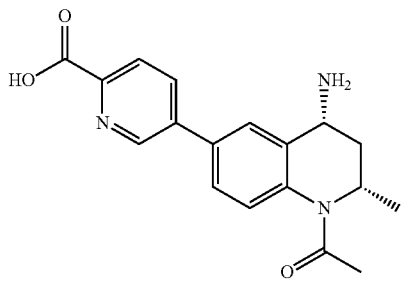 [SMILES: CC(=O)N1c2ccc(-c3ccc(C(=O)O)nc3)cc2[C@H](N)C[C@@H]1C]

To methyl 5-((2S,4R)-1-acetyl-4-amino-2-methyl-1,2,3,4-tetrahydroquinolin-6-yl)picolinate (for a preparation, see Intermediate 54) (550 mg, 1.62 mmol) in MeOH (5 mL) was added lithium hydroxide monohydrate (78 mg, 3.24 mmol) in water (5 mL) and the mixture stirred at room temperature for 90 mins. The mixture was concentrated in vacuo before DCM was added. The mixture was filtered, dried by passing through a hydrophobic frit, and concentrated in vacuo to give 5-((2S,4R)-1-acetyl-4-amino-2-methyl-1,2,3,4-tetrahydroquinolin-6-yl)picolinic acid (517 mg, 1.59 mmol, 98% yield).

LCMS: (Formate, 2 min), Rt=0.38 mins, MH+=326.

Intermediate 56

1-((2S,4R)-4-amino-2-methyl-6-(6-(morpholine-4-carbonyl)pyridin-3-yl)-3,4-dihydroquinolin-1(2H)-yl)ethanone

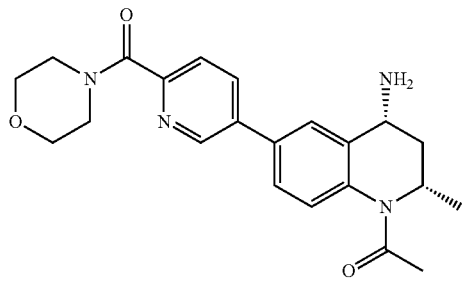 [SMILES: CC(=O)N1c2ccc(-c3ccc(C(=O)N4CCOCC4)nc3)cc2[C@H](N)C[C@@H]1C]

5-((2S,4R)-1-acetyl-4-amino-2-methyl-1,2,3,4-tetrahydroquinolin-6-yl)picolinic acid (for a preparation, see Intermediate 55) (510 mg, 1.567 mmol), morpholine (0.149 mL, 1.72 mmol), HATU (656 mg, 1.724 mmol) and DIPEA (0.821 mL, 4.70 mmol) were combined in DMF (5 mL) and the mixture stirred at room temperature overnight. Morpholine (0.149 mL, 1.72 mmol) was added and the reaction stirred at room temperature for a further 3 h. The mixture was concentrated in vacuo before being dissolved in DCM and loaded onto an aminopropyl SPE column (50 g). The column was eluted with 10% MeOH in DCM and the appropriate fractions were combined and concentrated in vacuo to give a residue. This residue was purified by chromatography (50 g column, 2M methanolic ammonia/DCM gradient) to give 1-((2S,4R)-4-amino-2-methyl-6-(6-(morpholine-4-carbonyl)pyridin-3-yl)-3,4-dihydroquinolin-1(2H)-yl)ethanone (470 mg, 1.19 mmol, 76% yield) as a beige solid. LCMS: (Formate, 2 min), Rt=0.48 mins, MH+=395.

Intermediate 57

Ethyl 4-((2S,4R)-1-acetyl-2-methyl-4-(pyridin-2-ylamino)-1,2,3,4-tetrahydroquinolin-6-yl)benzoate

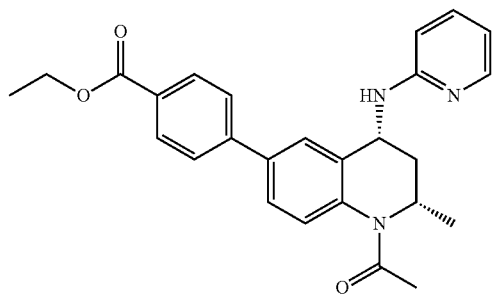 [SMILES: CCOC(=O)c1ccc(-c2ccc3c(c2)[C@H](Nc2ccccn2)C[C@H](C)N3C(C)=O)cc1]

Sodium tert-butoxide (135 mg, 1.41 mmol)) was added to a suspension of ethyl 4-((2S,4R)-1-acetyl-4-amino-2-methyl-1,2,3,4-tetrahydroquinolin-6-yl)benzoate (for a preparation see Intermediate 16) (450 mg, 1.28 mmol), 2-bromopyridine (403 mg, 2.55 mmol), 2'-(dicyclohexylphosphino)-N,N-dimethyl-[1,1'-biphenyl]-2-amine (40 mg, 0.102 mmol) and tris(dibenzyldieneacetone)dipalladium(0) (47 mg, 0.051 mmol) in anhydrous toluene (4.5 mL). The mixture was heated under microwave irradiation to 120° C. for 1 h in a sealed vial. The mixture was partitioned between EtOAc and water, the aqueous layer was extracted twice with EtOAc, the combined organic phases were dried by passing through a hydrophobic frit and concentrated in vacuo to give a residue. The residue was purified by chromatography (10 g column, EtOAc/cyclohexane gradient followed by MeOH/EtOAc gradient) to give ethyl 4-((2S,4R)-1-acetyl-2-methyl-4-(pyridin-2-ylamino)-1,2,3,4-tetrahydroquinolin-6-yl)benzoate (216 mg, 0.503 mmol, 39% yield) as a brown gum. LCMS: (Formate, 2 min), Rt=0.84 min, MH+430.

Intermediate 58

Lithium 4-((2S,4R)-1-acetyl-2-methyl-4-(pyridin-2-ylamino)-1,2,3,4-tetrahydroquinolin-6-yl)benzoate

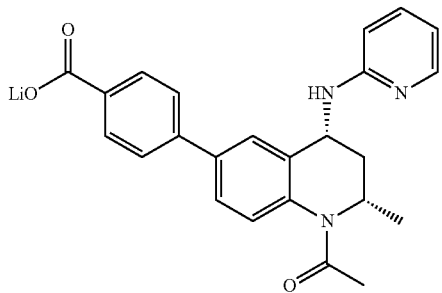

Ethyl 4-((2S,4R)-1-acetyl-2-methyl-4-(pyridin-2-ylamino)-1,2,3,4-tetrahydroquinolin-6-yl)benzoate (for a preparation see Intermediate 57) (216 mg, 0.503 mmol) in EtOH (1 mL) and water (0.5 mL) was treated with lithium hydroxide monohydrate (22 mg, 0.524 mmol) and the mixture stirred at r.t. over the weekend. A further portion of lithium hydroxide monohydrate (4 mg, 0.095 mmol) was added to the reaction and the mixture stirred for 1 h. The mixture was concentrated to dryness to give the crude product lithium 4-((2S,4R)-1-acetyl-2-methyl-4-(pyridin-2-ylamino)-1,2,3,4-tetrahydroquinolin-6-yl)benzoate (160 mg) which was used directly in the next step without further purification.

LCMS: (Formate, 2 min), Rt=0.62 min, MH+402.

Intermediate 59

Ethyl 4-((2S,4R)-1-acetyl-2-methyl-4-((5-methylpyridin-2-yl)amino)-1,2,3,4-tetrahydroquinolin-6-yl)benzoate

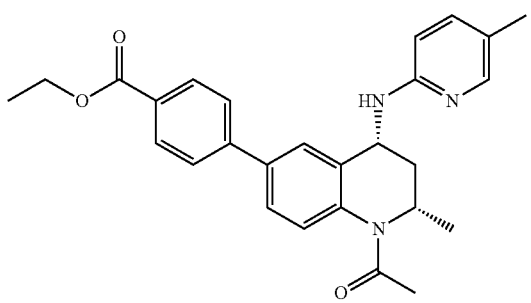 [SMILES: CCOC(=O)c1ccc(-c2ccc3c(c2)[C@H](Nc2ccc(C)cn2)C[C@H](C)N3C(C)=O)cc1]

Sodium tert-butoxide (135 mg, 1.41 mmol)) was added to a suspension of ethyl 4-((2S,4R)-1-acetyl-4-amino-2-methyl-1,2,3,4-tetrahydroquinolin-6-yl)benzoate (for a preparation see Intermediate 16) (450 mg, 1.28 mmol), 2-bromo-5-methylpyridine (439 mg, 2.55 mmol), 2'-(dicyclohexylphosphino)-N,N-dimethyl-[1,1'-biphenyl]-2-amine (40 mg, 0.102 mmol) and tris(dibenzyldieneacetone)dipalladium(0) (47 mg, 0.051 mmol) in anhydrous toluene (4.5 mL). The mixture was heated under microwave irradiation to 120° C. for 1 h in a sealed vial. The mixture was partitioned between EtOAc and water, the aqueous layer was extracted twice with EtOAc, the combined organic phases were dried by passing through a hydrophobic frit and concentrated in vacuo to give a residue. The residue was purified by chromatography (10 g column, EtOAc/cyclohexane gradient followed by MeOH/EtOAc gradient) to give a residue. This residue was dissolved in a mixture of EtOAc (0.6 mL) and cyclohexane (0.4 mL). The solution was treated with cyclohexane (3 mL) to give an emulsion, which was allowed to stand at room temperature over a weekend. The solution was decanted from the precipitated dark brown oil and concentrated to dryness under a stream of nitrogen to give an oil. This oil was triturated with cyclohexane (2×3 mL), the residual gum isolated by decanting off the cyclohexane, dissolved in EtOAc and concentrated to dryness under a stream of nitrogen to give crude ethyl 4-((2S,4R)-1-acetyl-2-methyl-4-((5-methylpyridin-2-yl)amino)-1,2,3,4-tetrahydroquinolin-6-yl)benzoate as a pale brown foam (240 mg) which was used directly in the next step without further purification.

LCMS: (Formate, 2 min), Rt=0.88 min, MH+444.

Intermediate 60

Lithium 4-((2S,4R)-1-acetyl-2-methyl-4-((5-methylpyridin-2-yl)amino)-1,2,3,4-tetrahydroquinolin-6-yl)benzoate

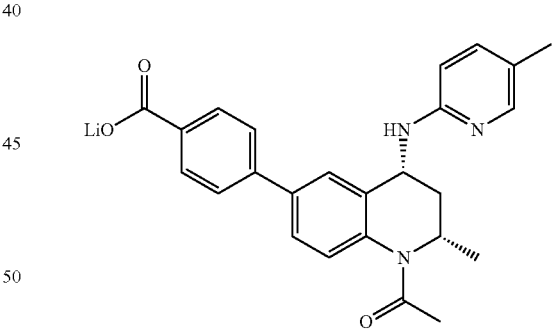

Crude ethyl 4-((2S,4R)-1-acetyl-2-methyl-4-((5-methylpyridin-2-yl)amino)-1,2,3,4-tetrahydroquinolin-6-yl)benzoate (Intermediate 59) (238 mg) in EtOH (2 mL) and water (1 mL) was treated with lithium hydroxide monohydrate (26 mg, 0.620 mmol). The solution was stirred at ambient temperature for 5 h. A further portion of lithium hydroxide monohydrate (4 mg, 0.095 mmol) was added and the mixture left at ambient temperature overnight. The mixture was concentrated to dryness to give crude lithium 4-((2S,4R)-1-acetyl-2-methyl-4-((5-methylpyridin-2-yl)amino)-1,2,3,4-tetrahydroquinolin-6-yl)benzoate as a brown foam (240 mg) which was used directly in the next step without further purification.

LCMS: (Formate, 2 min), Rt=0.65 min, MH+416.

Intermediate 61

Tert-butyl ((2S,4R)-1-acetyl-2-methyl-6-(4,4,5,5-tetramethyl-1,3,2-dioxaborolan-2-yl)-1,2,3,4-tetrahydroquinolin-4-yl)carbamate

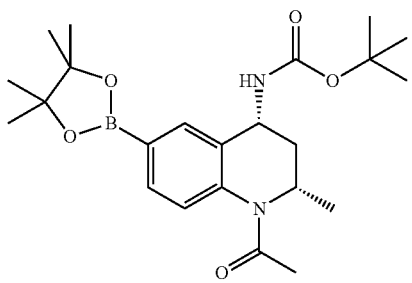 [SMILES: CC(=O)N1c2ccc(B3OC(C)(C)C(C)(C)O3)cc2[C@H](NC(=O)OC(C)(C)C)C[C@@H]1C]

Tert-butyl ((2S,4R)-1-acetyl-6-bromo-2-methyl-1,2,3,4-tetrahydroquinolin-4-yl)carbamate (for a preparation, see Intermediate 29) (2.0 g, 5.22 mmol), bis(pinacolato)diboron (2.92 g, 11.48 mmol), PdCl$_2$(dppf) (0.191 g, 0.261 mmol) and potassium acetate (1.54 g, 15.65 mmol) were combined in 1,4-dioxane (25 mL) and degassed. The mixture was then heated under a nitrogen atmosphere for 75 mins at 105° C. The mixture was concentrated in vacuo and the residue purified by chromatography (100 g column, EtOAc/cyclohexane) to give tert-butyl ((2S,4R)-1-acetyl-2-methyl-6-(4,4,5,5-tetramethyl-1,3,2-dioxaborolan-2-yl)-1,2,3,4-tetrahydroquinolin-4-yl)carbamate (2.36 g, 4.94 mmol, 95% yield).

LCMS: (Formate, 2 min), Rt=1.21 mins, MH+=431.

Intermediate 62

Methyl 6-((2S,4R)-1-acetyl-4-((tert-butoxycarbonyl)amino)-2-methyl-1,2,3,4-tetrahydroquinolin-6-yl)nicotinate

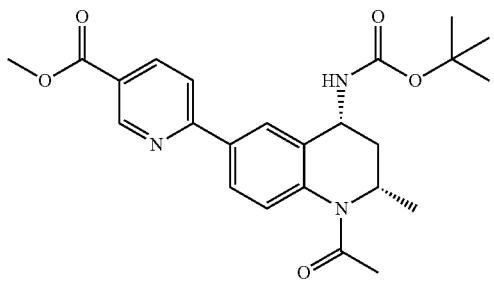 [SMILES: COC(=O)c1ccc(-c2ccc3c(c2)[C@H](NC(=O)OC(C)(C)C)C[C@H](C)N3C(C)=O)nc1]

Tert-butyl ((2S,4R)-1-acetyl-2-methyl-6-(4,4,5,5-tetramethyl-1,3,2-dioxaborolan-2-yl)-1,2,3,4-tetrahydroquinolin-4-yl)carbamate (for a preparation see Intermediate 61) (2.2 g, 5.11 mmol), methyl 6-bromonicotinate (1.325 g, 6.13 mmol), Pd(PPh$_3$)$_4$ (0.591 g, 0.511 mmol) and potassium carbonate (2.120 g, 15.34 mmol) were combined in methanol (10 mL) and DME (3 mL) and heated under microwave irradiation to 100° C. for 70 mins.

In a separate vial, Tert-butyl ((2S,4R)-1-acetyl-2-methyl-6-(4,4,5,5-tetramethyl-1,3,2-dioxaborolan-2-yl)-1,2,3,4-tetrahydroquinolin-4-yl)carbamate (for a preparation see Intermediate 61) (2.2 g, 5.11 mmol), methyl 6-bromonicotinate (1.325 g, 6.13 mmol), Pd(PPh$_3$)$_4$ (0.591 g, 0.511 mmol) and potassium carbonate (2.120 g, 15.34 mmol) were combined in methanol (10 mL) and DME (3 mL) and heated under microwave irradiation to 100° C. for 70 mins. The two reaction mixtures were combined and partitioned between water (150 mL) and DCM (3×150 mL). The aqueous layer was acidified to pH 3 via the addition of aq. HCl and extracted with DCM (3×100 mL). The combined organic layers were dried by passing through a hydrophobic frit, and concentrated in vacuo to give crude methyl 6-((2S,4R)-1-acetyl-4-((tert-butoxycarbonyl)amino)-2-methyl-1,2,3,4-tetrahydroquinolin-6-yl)nicotinate (2.2 g) which was used directly in the next step without further purification. LCMS: (Formate, 2 min), Rt=1.06 min, MH+440.

Intermediate 63

6-((2S,4R)-1-acetyl-4-((tert-butoxycarbonyl)amino)-2-methyl-1,2,3,4-tetrahydroquinolin-6-yl)nicotinic acid

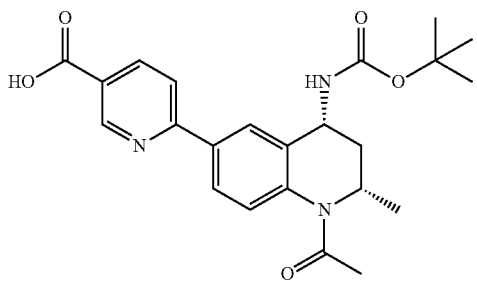

To a stirring solution of crude methyl 6-((2S,4R)-1-acetyl-4-((tert-butoxycarbonyl)amino)-2-methyl-1,2,3,4-tetrahydroquinolin-6-yl)nicotinate (Intermediate 62) (2.2 g, 5.01 mmol) in MeOH1 (12 mL), was added lithium hydroxide monohydrate (0.144 g, 6.01 mmol) in water (12 mL) and the mixture warmed to 50° C. for 70 mins. MeOH (10 mL) was added and the mixture stirred at 50° C. for a further 50 mins. The mixture was allowed to cool to room temperature before being partitioned between saturated aqueous sodium bicarbonate (150 mL) and DCM (3×150 mL). The aqueous layer was then treated with 2M HCl until acidic (~pH 3) before being extracted with DCM (3×150 ml). The organics were combined, dried by passing through a hydrophobic frit and concentrated in vacuo to give 6-((2S,4R)-1-acetyl-4-((tert-butoxycarbonyl)amino)-2-methyl-1,2,3,4-tetrahydroquinolin-6-yl)nicotinic acid (2.08 g, 4.89 mmol). LCMS: (Formate, 2 min), Rt=0.86 mins, MH+426.

Intermediate 64

Tert-butyl ((2S,4R)-1-acetyl-2-methyl-6-(5-(morpholine-4-carbonyl)pyridin-2-yl)-1,2,3,4-tetrahydroquinolin-4-yl)carbamate

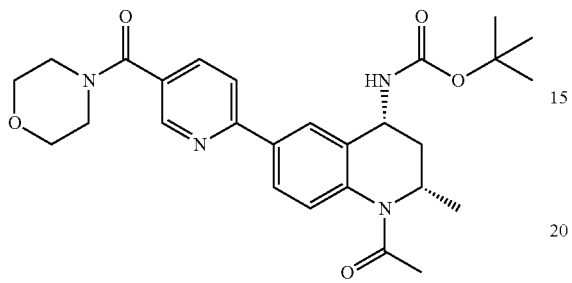

6-((2S,4R)-1-acetyl-4-((tert-butoxycarbonyl)amino)-2-methyl-1,2,3,4-tetrahydroquinolin-6-yl)nicotinic acid (for a preparation, see Intermediate 63) (2.05 g, 4.82 mmol), morpholine (2.084 mL, 24.09 mmol), HATU (2.015 g, 5.30 mmol) and DIPEA (2.52 mL, 14.45 mmol) were combined in DMF (25 mL) and the reaction stirred at room temperature for 90 mins. The mixture was concentrated in vacuo before being dissolved in DCM and loaded onto an aminopropyl SPE column (70 g). The column was eluted with 10% MeOH in DCM, and the appropriate fractions combined and concentrated to dryness in cavuo. The residue was purified by chromatography (100 g column, EtOAc/cyclohexane gradient) to give tert-butyl ((2S,4R)-1-acetyl-2-methyl-6-(5-(morpholine-4-carbonyl)pyridin-2-yl)-1,2,3,4-tetrahydroquinolin-4-yl)carbamate (2.05 g, 4.14 mmol, 86% yield).

LCMS: (Formate, 2 min), Rt=0.86 mins, MH+495.

Intermediate 65

1-((2S,4R)-4-amino-2-methyl-6-(5-(morpholine-4-carbonyl)pyridin-2-yl)-3,4-dihydroquinolin-1(2H)-yl)ethanone hydrochloride

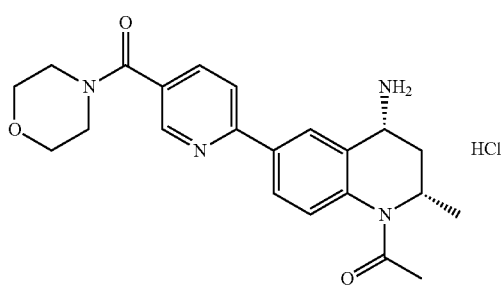 [SMILES: CC(=O)N1c2ccc(-c3ccc(C(=O)N4CCOCC4)cn3)cc2[C@H](N)C[C@@H]1C ; Cl]

4M hydrochloric acid in 1,4-dioxane (10.11 ml, 40.4 mmol) was added to tert-butyl ((2S,4R)-1-acetyl-2-methyl-6-(5-(morpholine-4-carbonyl)pyridin-2-yl)-1,2,3,4-tetrahydroquinolin-4-yl)carbamate (for a preparation, see Intermediate 64) (2 g, 4.04 mmol) at room temperature, followed by MeOH (10 mL) and DCM (10 mL) and the mixture stirred at room temperature for 2 mins. The mixture was concentrated in vacuo to give 1-((2S,4R)-4-amino-2-methyl-6-(5-(morpholine-4-carbonyl)pyridin-2-yl)-3,4-dihydroquinolin-1(2H)-yl)ethanone hydrochloride (1.60 g, 3.71 mmol, 92% yield).

LCMS: (Formate, 2 min), Rt=0.50 mins, MH+395.

Intermediate 66

Ethyl 4-((2S,4R)-1-acetyl-4-((5-cyanopyridin-2-yl)amino)-2-methyl-1,2,3,4-tetrahydroquinolin-6-yl)benzoate

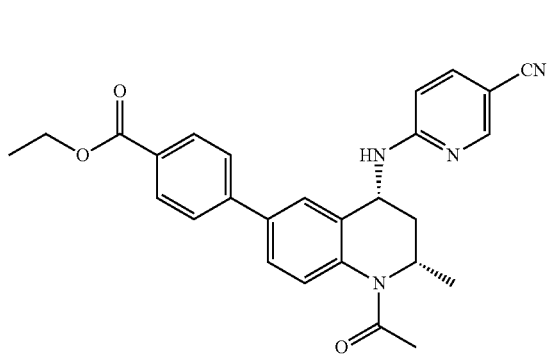 [SMILES: CCOC(=O)c1ccc(-c2ccc3c(c2)[C@H](Nc2ccc(C#N)cn2)C[C@H](C)N3C(C)=O)cc1]

Ethyl 4-((2S,4R)-1-acetyl-4-amino-2-methyl-1,2,3,4-tetrahydroquinolin-6-yl)benzoate (for a preparation, see Intermediate 16) (300 mg, 0.851 mmol) and 6-chloronicotinonitrile (236 mg, 1.702 mmol) in anhydrous NMP (5 mL) were treated with DIPEA (0.445 mL, 2.55 mmol). The reaction vial was sealed and heated under microwave irradiation to 200° C. for 2 h. The cooled solution was diluted with water to ~20 mL, stirred and the resulting sticky solid isolated by decantation. The solid was dissolved in EtOAc, the solution washed with brine and dried by passing through a hydrophobic frit. The solution was concentrated in vacuo and the residue purified by MDAP (Formate) to give crude ethyl 4-((2S,4R)-1-acetyl-4-((5-cyanopyridin-2-yl)amino)-2-methyl-1,2,3,4-tetrahydroquinolin-6-yl)benzoate (120 mg) as a beige gum which was used directly in the next step without further purification.

LCMS: (Formate, 2 min), Rt=1.12 min, MH+455.

Intermediate 67

Lithium 4-((2S,4R)-1-acetyl-4-((5-cyanopyridin-2-yl)amino)-2-methyl-1,2,3,4-tetrahydroquinolin-6-yl)benzoate

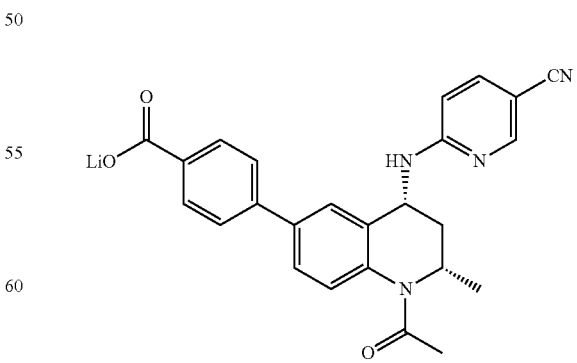

A solution of crude ethyl 4-((2S,4R)-1-acetyl-4-((5-cyanopyridin-2-yl)amino)-2-methyl-1,2,3,4-tetrahydroquinolin-6-yl)benzoate (Intermediate 66) (120 mg) in EtOH (2 mL)

was treated with lithium hydroxide monohydrate (13 mg, 0.303 mmol) and water (1 mL). The mixture was stirred at room temperature for ~24 h. The solution was concentrated to dryness to give crude lithium 4-((2S,4R)-1-acetyl-4-((5-cyanopyridin-2-yl)amino)-2-methyl-1,2,3,4-tetrahydroquinolin-6-yl)benzoatecrude as a crunchy yellow foam (110 mg) which was used directly in the next step without further purification.

LCMS: (Formate, 2 min), Rt=0.87 min, MH+427.

Example 1

3-(4-((2S,4R)-1-Acetyl-4-((5-cyanopyridin-2-yl)amino)-2-methyl-1,2,3,4-tetrahydroquinolin-6-yl)phenyl)-N-(2-(dimethylamino)ethyl)propanamide

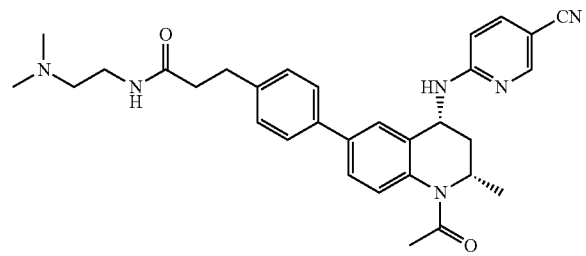 [SMILES: CC(=O)N1c2ccc(-c3ccc(CCC(=O)NCCN(C)C)cc3)cc2[C@H](Nc2ccc(C#N)cn2)C[C@@H]1C]

To a solution of 3-(4-((2S,4R)-1-acetyl-4-((5-cyanopyridin-2-yl)amino)-2-methyl-1,2,3,4-tetrahydroquinolin-6-yl)phenyl)propanoic acid (for a preparation See Intermediate 10)(58 mg, 0.128 mmol) and N1,N1-dimethylethane-1,2-diamine (22.50 mg, 0.255 mmol) in DMF (3 mL) were added HATU (72.8 mg, 0.191 mmol) and DIPEA (0.067 mL, 0.383 mmol). The resulting mixture was stirred for 30 min, then reaction mixture partitioned between water and EtOAc. The aqueous phase was extracted with EtOAc (×3), the combined organic layers were washed with brine, dried over MgSO₄, filtered and concentrated in vacuo. The crude residue was dissolved in 1:1 MeOH/DMSO and was purified by MDAP (formate). The appropriate fractions were combined and concentrated in vacuo to give 3-(4-((2S,4R)-1-acetyl-4-((5-cyanopyridin-2-yl)amino)-2-methyl-1,2,3,4-tetrahydroquinolin-6-yl)phenyl)-N-(2-(dimethylamino)ethyl)propanamide (34.6 mg, 48%) as a viscous colourless oil. LCMS (Formate, 2 min), Rt=0.71 min, MH+=525.

Example 2

3-(4-((2S,4R)-1-Acetyl-4-((5-cyanopyridin-2-yl)amino)-2-methyl-1,2,3,4-tetrahydroquinolin-6-yl)phenyl)-N-(2-hydroxyethyl)propanamide

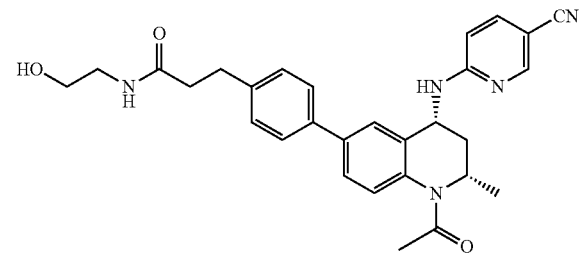 [SMILES: CC(=O)N1c2ccc(-c3ccc(CCC(=O)NCCO)cc3)cc2[C@H](Nc2ccc(C#N)cn2)C[C@@H]1C]

To a solution of 3-(4-((2S,4R)-1-acetyl-4-((5-cyanopyridin-2-yl)amino)-2-methyl-1,2,3,4-tetrahydroquinolin-6-yl)phenyl)propanoic acid (for a preparation see Intermediate 10)(44 mg, 0.097 mmol) and ethanolamine (0.012 mL, 0.194 mmol) in DMF (3 mL) were added HATU (55.2 mg, 0.145 mmol) and DIPEA (0.051 mL, 0.290 mmol). The resulting mixture was stirred for 40 min, then partitioned between water and EtOAc. The aqueous phase was extracted with EtOAc (×3), the combined organic layers were washed with brine, dried over MgSO₄, filtered and concentrated in vacuo. The crude residue was dissolved in 1:1 MeOH/DMSO and was purified by MDAP (formate). The appropriate fractions were combined and concentrated in vacuo to give 3-(4-((2S,4R)-1-acetyl-4-((5-cyanopyridin-2-yl)amino)-2-methyl-1,2,3,4-tetrahydroquinolin-6-yl)phenyl)-N-(2-hydroxyethyl)propanamide (22.8 mg, 47%) as a, viscous yellow oil. LCMS (Formate, 2 min), Rt=0.80 min, MH+=498.

Example 3

2-(4-((2S,4R)-1-Acetyl-4-((5-cyanopyridin-2-yl)amino)-2-methyl-1,2,3,4-tetrahydroquinolin-6-yl)phenyl)-N-(2-hydroxyethyl)acetamide

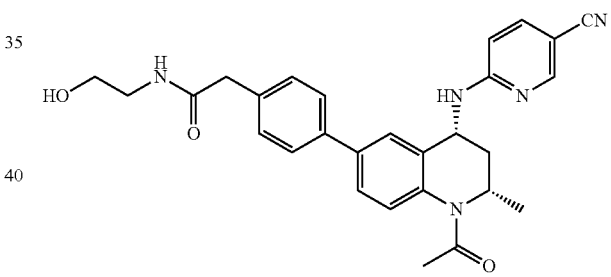

To a solution of 2-(4-((2S,4R)-1-acetyl-4-((5-cyanopyridin-2-yl)amino)-2-methyl-1,2,3,4-tetrahydroquinolin-6-yl)phenyl)acetic acid, lithium salt (Intermediate 9)(166 mg, 0.377 mmol) and ethanolamine (0.034 mL, 0.565 mmol) in DMF (3 mL) were added HATU (287 mg, 0.754 mmol) and DIPEA (0.197 mL, 1.131 mmol). The resulting mixture was stirred at room temperature for 1 h, the reaction mixture was diluted with EtOAc and water. The layers were separated and the aqueous phase was extracted with EtOAc (×3). The combined organic layers were washed with brine, dried over MgSO₄, filtered and concentrated in vacuo. The crude residue was dissolved in 1:1 MeOH/DMSO and was purified by MDAP (formate). The appropriate fractions were combined and concentrated in vacuo to give 2-(4-((2S,4R)-1-acetyl-4-((5-cyanopyridin-2-yl)amino)-2-methyl-1,2,3,4-tetrahydroquinolin-6-yl)phenyl)-N-(2-hydroxyethyl)acetamide (21 mg, 11%) as a colourless oil. LCMS (Formate, 2 min), Rt=0.76 min, MH+=484.

Example 4

2-(4-((2S,4R)-1-Acetyl-4-((5-cyanopyridin-2-yl) amino)-2-methyl-1,2,3,4-tetrahydroquinolin-6-yl) phenyl)-N-(1,3-dihydroxypropan-2-yl)acetamide

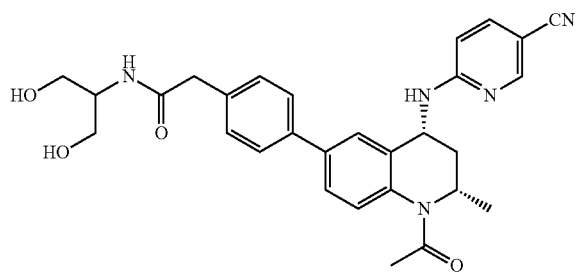 [SMILES: CC(=O)N1c2ccc(-c3ccc(CC(=O)NC(CO)CO)cc3)cc2[C@H](Nc2ccc(C#N)cn2)C[C@@H]1C]

To a solution of 2-(4-((2S,4R)-1-acetyl-4-((5-cyanopyridin-2-yl)amino)-2-methyl-1,2,3,4-tetrahydroquinolin-6-yl) phenyl)acetic acid, lithium salt (for a preparation see Intermediate 9)(169 mg, 0.384 mmol) and 2-aminopropane-1,3-diol (69.9 mg, 0.767 mmol) in DMF (2 ml) were added HATU (190 mg, 0.499 mmol) and DIPEA (0.201 mL, 1.151 mmol). The resulting mixture was stirred at room temperature for 2 h. The reaction mixture was diluted with EtOAc and water. The layers were separated and the aqueous phase was extracted with EtOAc (×3). The combined organic layers were washed with brine, dried over MgSO$_4$, filtered and concentrated in vacuo. The crude residue was dissolved in 1:1 MeOH/DMSO and was purified by MDAP (formate). The appropriate fractions were combined and concentrated in vacuo to give 2-(4-((2S,4R)-1-acetyl-4-((5-cyanopyridin-2-yl)amino)-2-methyl-1,2,3,4-tetrahydroquinolin-6-yl)phenyl)-N-(1,3-dihydroxypropan-2-yl)acetamide (83 mg, 42%) as a colourless oil. LCMS (Formate, 2 min), Rt=0.73 min, MH+=514.

Example 5

2-(4-((2S,4R)-1-Acetyl-4-((5-cyanopyridin-2-yl) amino)-2-methyl-1,2,3,4-tetrahydroquinolin-6-yl) phenyl)-N-(2-(dimethylamino)ethyl)acetamide

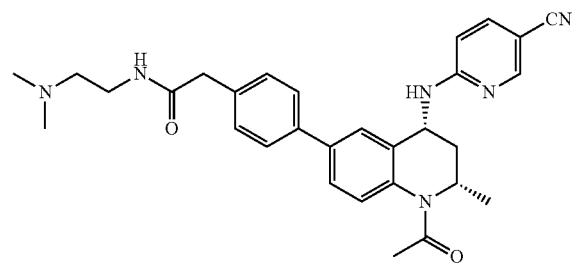 [SMILES: CC(=O)N1c2ccc(-c3ccc(CC(=O)NCCN(C)C)cc3)cc2[C@H](Nc2ccc(C#N)cn2)C[C@@H]1C]

To a solution of 2-(4-((2S,4R)-1-acetyl-4-((5-cyanopyridin-2-yl)amino)-2-methyl-1,2,3,4-tetrahydroquinolin-6-yl) phenyl)acetic acid, lithium salt (for a preparation see Intermediate 9)(125 mg, 0.284 mmol) and N1,N1-dimethylethane-1,2-diamine (32.5 mg, 0.369 mmol) in DMF (3 mL) were added HATU (162 mg, 0.426 mmol) and DIPEA (0.149 mL, 0.851 mmol). The resulting mixture was stirred at room temperature for 2 h, the reaction mixture was diluted with EtOAc and water. The layers were separated and the aqueous phase was extracted with EtOAc (×3). The combined organic layers were washed with brine, dried over MgSO$_4$, filtered and concentrated in vacuo. The crude residue was dissolved in 1:1 MeOH/DMSO and was purified by MDAP (formate). The appropriate fractions were combined and concentrated in vacuo to give 2-(4-((2S,4R)-1-acetyl-4-((5-cyanopyridin-2-yl)amino)-2-methyl-1,2,3,4-tetrahydroquinolin-6-yl)phenyl)-N-(2-(dimethylamino)ethyl)acetamide (59 mg, 41%) as a colourless oil. LCMS (Formate, 2 min), Rt=0.65 min, MH+=511.

Example 6

Isopropyl ((2S,4R)-1-acetyl-6-(4-((2-aminoethyl) carbamoyl)phenyl)-2-methyl-1,2,3,4-tetrahydroquinolin-4-yl)carbamate hydrochloride

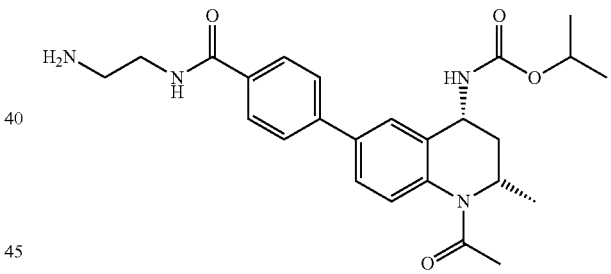

A solution of 1-methylethyl {(2S,4R)-1-acetyl-6-[4-({[2-({[(1,1-dimethylethyl)oxy]carbonyl}amino)ethyl] amino}carbonyl)phenyl]-2-methyl-1,2,3,4-tetrahydro-4-quinolinyl}carbamate (for a preparation see Intermediate 37) (90 mg, 0.163 mmol) in dioxane (2 ml) was treated with hydrogen chloride in 1,4-dioxane (4N, 2 mL, 8.00 mmol) and the resulting mixture stirred at room temperature for 5 h, then concentrated in vacuo. The resulting residue was triturated with Et$_2$O and isolated by filtration to give isopropyl ((2S, 4R)-1-acetyl-6-(4-((2-aminoethyl)carbamoyl)phenyl)-2-methyl-1,2,3,4-tetrahydroquinolin-4-yl)carbamate hydrochloride (68 mg, 0.139 mmol, 85% yield) as a pale yellow solid. LCMS (HpH, 2 min), Rt=0.78 min.

Example 7

Isopropyl ((2S,4R)-1-acetyl-6-(4-((2-(dimethylamino)ethyl)carbamoyl)phenyl)-2-methyl-1,2,3,4-tetrahydroquinolin-4-yl)carbamate

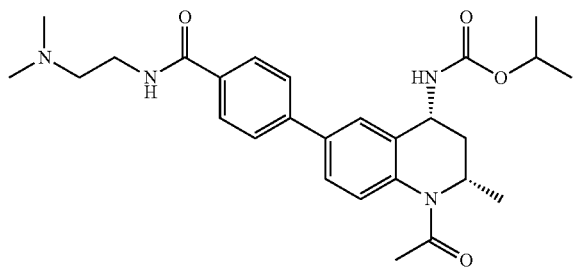 [SMILES: CC(=O)N1c2ccc(-c3ccc(C(=O)NCCN(C)C)cc3)cc2[C@H](NC(=O)OC(C)C)C[C@@H]1C]

To a solution of 4-((2S,4R)-1-acetyl-4-((isopropoxycarbonyl)amino)-2-methyl-1,2,3,4-tetrahydroquinolin-6-yl)benzoic acid (for a preparation see Intermediate 48) (67 mg, 0.163 mmol) and N1,N1-dimethylethane-1,2-diamine (28.8 mg, 0.326 mmol) in DMF (2 mL) were added HATU (93 mg, 0.245 mmol) and DIPEA (0.086 mL, 0.490 mmol). The resulting mixture was stirred at room temperature for 1 h, then hydrolyzed by adding water and EtOAc. The layers were separated and the aqueous phase was extracted with EtOAc (×3). The combined organic layers were washed with brine, dried over MgSO₄, filtered and concentrated in vacuo. The residue was dissolved in 1:1 MeOH/DMSO and was purified by MDAP (formate). The appropriate fractions were combined and concentrated under reduced pressure to give isopropyl ((2S,4R)-1-acetyl-6-(4-((2-(dimethylamino)ethyl)carbamoyl)phenyl)-2-methyl-1,2,3,4-tetrahydroquinolin-4-yl)carbamate (35 mg, 41%) as a viscous colourless oil. LCMS (Formate, 2 min), Rt=0.65 min, MH+=481.

Example 8

Isopropyl ((2S,4R)-1-acetyl-6-(4-((2-hydroxyethyl)carbamoyl)phenyl)-2-methyl-1,2,3,4-tetrahydroquinolin-4-yl)carbamate

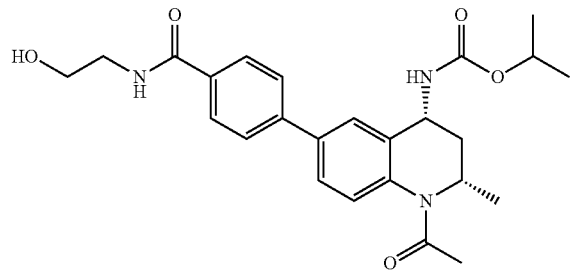 [SMILES: CC(=O)N1c2ccc(-c3ccc(C(=O)NCCO)cc3)cc2[C@H](NC(=O)OC(C)C)C[C@@H]1C]

To a solution of 4-((2S,4R)-1-acetyl-4-((isopropoxycarbonyl)amino)-2-methyl-1,2,3,4-tetrahydroquinolin-6-yl)benzoic acid (for a preparation see Intermediate 48) (116 mg, 0.283 mmol) and ethanolamine (0.034 mL, 0.565 mmol) in DMF (3 mL) were added HATU (161 mg, 0.424 mmol) and DIPEA (0.148 mL, 0.848 mmol). The resulting mixture was stirred at room temperature for 1 h, then water and EtOAc were added. The layers were separated and the aqueous phase was extracted with EtOAc (×3). The combined organic layers were washed with brine, dried over MgSO₄, filtered and concentrated in vacuo. The residue was dissolved in 1:1 MeOH/DMSO and was purified by MDAP (formate). The appropriate fractions were combined and concentrated under reduced pressure to give isopropyl ((2S,4R)-1-acetyl-6-(4-((2-hydroxyethyl)carbamoyl)phenyl)-2-methyl-1,2,3,4-tetrahydroquinolin-4-yl)carbamate (102 mg, 80%) as a white solid. LCMS (Formate, 2 min), Rt=0.76 min, MH+=454.

Example 9

Isopropyl ((2S,4R)-1-acetyl-6-(4-(2-((2-aminoethyl)amino)-2-oxoethyl)phenyl)-2-methyl-1,2,3,4-tetrahydroquinolin-4-yl)carbamate hydrochloride

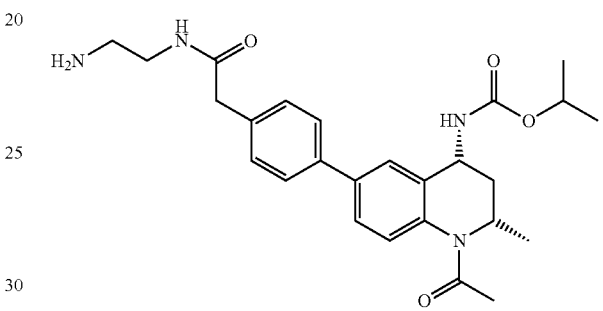

A solution of 1-methylethyl {(2S,4R)-1-acetyl-6-[4-(2-{[2-({[(1,1-dimethylethyl)oxy]carbonyl}amino)ethyl]amino}-2-oxoethyl)phenyl]-2-methyl-1,2,3,4-tetrahydro-4-quinolinyl}carbamate (for a preparation see Intermediate 38) (60 mg, 0.106 mmol) in 1,4-dioxane (2 ml) was treated with hydrogen chloride in 1,4-dioxane (4N, 2 mL, 8.00 mmol) and the resulting mixture stirred at room temperature for 5 h then concentrated in vacuo. The residue was triturated with Et₂O and the solid isolated by filtration to give 1-methylethyl [(2S,4R)-1-acetyl-6-(4-{2-[(2-aminoethyl)amino]-2-oxoethyl}phenyl)-2-methyl-1,2,3,4-tetrahydro-4-quinolinyl]carbamate hydrochloride (28 mg, 0.056 mmol, 52.6% yield) as a pale yellow solid. LCMS (HpH, 2 min), Rt=0.79 min, MH+=467.

Example 10

6-((2S,4R)-1-acetyl-4-((5-cyanopyridin-2-yl)amino)-2-methyl-1,2,3,4-tetrahydroquinolin-6-yl)-N-(2-(dimethylamino)ethyl)nicotinamide

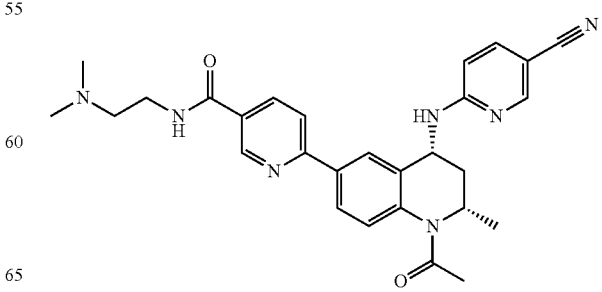

To a flask charged with 6-((2S,4R)-1-acetyl-4-((5-cyanopyridin-2-yl)amino)-2-methyl-1,2,3,4-tetrahydroquinolin-6-yl)nicotinic acid (for a preparation see Intermediate 7)(90 mg, 0.211 mmol) and HATU (96 mg, 0.253 mmol) was added DMF (3 mL) and the resulting mixture was treated with DIPEA (0.110 mL, 0.632 mmol). After stirring for 5 min, the mixture was treated with N1,N1-dimethylethane-1,2-diamine (37.1 mg, 0.421 mmol). After stirring for 3 min, the solution was partitioned between EtOAc and saturated aqueous NaHCO₃ solution and the layers were separated. The aqueous phase was extracted with EtOAc (×2) and the combined organic layers were washed with saturated aqueous NaHCO₃ (×3), then dried over MgSO₄ and concentrated in vacuo. The residue was purified by MDAP (HpH). The appropriate fractions were collected and concentrated in vacuo. The residue was subsequently dissolved in MeOH and dried (hydrophobic frit). The solvent was removed and the residue triturated in Et₂O to give 6-((2S,4R)-1-acetyl-4-((5-cyanopyridin-2-yl)amino)-2-methyl-1,2,3,4-tetrahydroquinolin-6-yl)-N-(2-(dimethylamino)ethyl)nicotinamide (36 mg, 0.072 mmol, 34.4% yield) as a white solid.

LCMS (HpH, 2 min), Rt=0.73 min, MH+=471.

Example 11

6-((2S,4R)-1-acetyl-4-((5-cyanopyridin-2-yl)amino)-2-methyl-1,2,3,4-tetrahydroquinolin-6-yl)-N-(1,3-dihydroxypropan-2-yl)nicotinamide

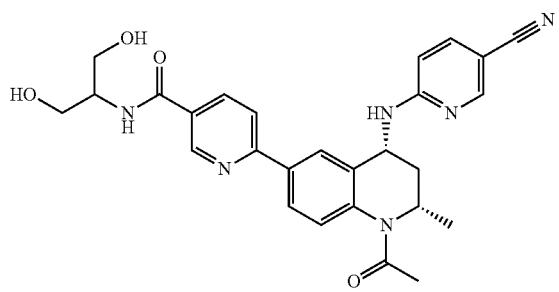 [SMILES: CC(=O)N1c2ccc(-c3ccc(C(=O)NC(CO)CO)cn3)cc2[C@H](Nc2ccc(C#N)cn2)C[C@@H]1C]

To a flask charged with 6-((2S,4R)-1-acetyl-4-((5-cyanopyridin-2-yl)amino)-2-methyl-1,2,3,4-tetrahydroquinolin-6-yl)nicotinic acid (for a preparation see Intermediate 7) (90 mg, 0.211 mmol) and HATU (96 mg, 0.253 mmol) was added DMF (3 mL) and the resulting mixture was treated with DIPEA (0.110 mL, 0.632 mmol). After stirring for 5 min, the mixture was treated with 2-aminopropane-1,3-diol (38.4 mg, 0.421 mmol). After stirring for 3 min, the solution was partitioned between EtOAc and saturated aqueous NaHCO₃ solution and the layers were separated. The aqueous phase was extracted with EtOAc (×2) and the combined organic layers were washed with saturated aqueous NaHCO₃ solution (×3), then dried over MgSO₄ and concentrated in vacuo. The residue was purified by MDAP (HpH). The appropriate fractions were collected and concentrated in vacuo. The residue was subsequently dissolved in MeOH and dried (hydrophobic frit). The solvent was removed and the residue triturated in Et₂O to give 6-((2S,4R)-1-acetyl-4-((5-cyanopyridin-2-yl)amino)-2-methyl-1,2,3,4-tetrahydroquinolin-6-yl)-N-(1,3-dihydroxypropan-2-yl)nicotinamide (26 mg, 0.052 mmol, 24.67% yield) as a white solid.

LCMS (HpH, 2 min), Rt=0.81 min, MH+=498.

Example 12

6-((2S,4R)-1-acetyl-4-((5-cyanopyridin-2-yl)amino)-2-methyl-1,2,3,4-tetrahydroquinolin-6-yl)-N-(2-hydroxyethyl)nicotinamide

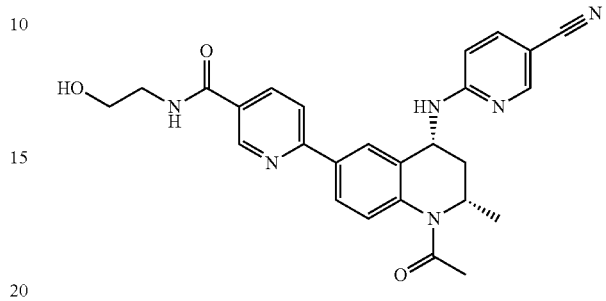

To a flask charged with 6-((2S,4R)-1-acetyl-4-((5-cyanopyridin-2-yl)amino)-2-methyl-1,2,3,4-tetrahydroquinolin-6-yl)nicotinic acid (for a preparation see Intermediate 7)(90 mg, 0.211 mmol) and HATU (96 mg, 0.253 mmol) was added DMF (3 mL) and the resulting mixture was treated with DIPEA (0.110 mL, 0.632 mmol). After stirring for 5 min, the mixture was treated with 2-aminoethanol (0.013 mL, 0.211 mmol). After stirring for 3 min, the solution was partitioned between EtOAc and saturated aqueous NaHCO₃ solution and the layers were separated. The aqueous phase was extracted with EtOAc (×2) and the combined organic layers were washed with saturated aqueous NaHCO₃ solution (×3), then dried over MgSO₄ and concentrated in vacuo. The residue was purified by MDAP (HpH). The appropriate fractions were collected and concentrated in vacuo. The residue was subsequently dissolved in MeOH and dried (hydrophobic frit). The solvent was removed and the residue triturated in Et₂O to give 6-((2S,4R)-1-acetyl-4-((5-cyanopyridin-2-yl)amino)-2-methyl-1,2,3,4-tetrahydroquinolin-6-yl)-N-(2-hydroxyethyl)nicotinamide (37 mg, 0.079 mmol, 37.3% yield) as a white solid. LC/MS (HpH, 2 min), Rt=0.70 min, MH+=501.

Example 13

4-((2S,4R)-1-acetyl-4-((5-cyanopyridin-2-yl)amino)-2-methyl-1,2,3,4-tetrahydroquinolin-6-yl)-N—((S)-2,3-dihydroxypropyl)benzamide

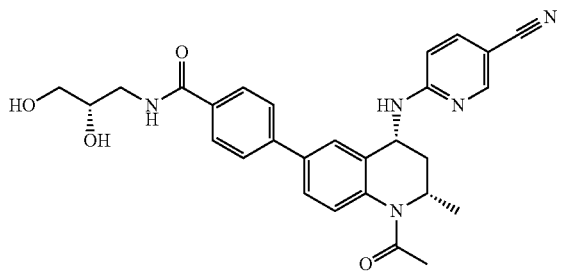 [SMILES: CC(=O)N1c2ccc(-c3ccc(C(=O)NC[C@H](O)CO)cc3)cc2[C@H](Nc2ccc(C#N)cn2)C[C@@H]1C]

A solution of 4-((2S,4R)-1-acetyl-4-((5-cyanopyridin-2-yl)amino)-2-methyl-1,2,3,4-tetrahydroquinolin-6-yl)benzoic acid (for a preparation see Intermediate 4) (90 mg, 0.211 mmol) in DMF (2 mL) was treated with EDC (48.5 mg, 0.253 mmol), HOBT hydrochloride (38.8 mg, 0.253 mmol) and N-ethylmorpholine (0.080 mL, 0.633 mmol) and after 3 min with (S)-3-aminopropane-1,2-diol (38.5 mg, 0.422 mmol). The resulting mixture was stirred at room temperature for 5 h then EDC (48.5 mg, 0.253 mmol), N-ethyl morpholine (0.080 mL, 0.633 mmol), HOBT (38.8 mg, 0.253 mmol) and further (S)-3-aminopropane-1,2-diol (38.5 mg, 0.422 mmol) were added and the corresponding mixture was stirred for 16 h then concentrated in vacuo. The residue was partitioned between water and EtOAc and the layers were separated. The aqueous phase was extracted with EtOAc (×2) and the combined organic layers were washed with saturated aqueous NaHCO₃ (×3), then brine, dried over MgSO₄ and concentrated in vacuo. The residue was purified by MDAP to give 4-((2S,4R)-1-acetyl-4-((5-cyanopyridin-2-yl)amino)-2-methyl-1,2,3,4-tetrahydroquinolin-6-yl)-N—((S)-2,3-dihydroxypropyl) benzamide (30 mg, 29%) as a white solid. LCMS (HpH, 2 min), Rt=0.75 min, MH+=500.

Example 14

4-((2S,4R)-1-acetyl-4-((5-cyanopyridin-2-yl)amino)-2-methyl-1,2,3,4-tetrahydroquinolin-6-yl)-N-(2-hydroxyethyl)benzamide

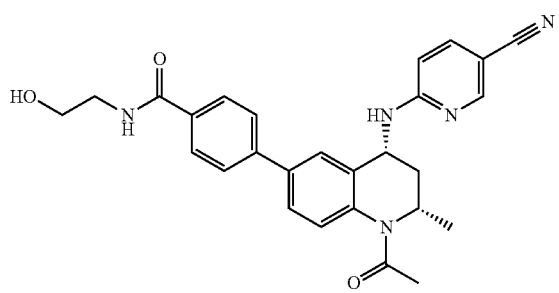

A solution of 4-((2S,4R)-1-acetyl-4-((5-cyanopyridin-2-yl)amino)-2-methyl-1,2,3,4-tetrahydroquinolin-6-yl)benzoic acid (for a preparation see Intermediate 4) (90 mg, 0.211 mmol) in DMF (2 mL) was treated with EDC (48.5 mg, 0.253 mmol), HOBT hydrochloride (38.8 mg, 0.253 mmol) and N-ethylmorpholine (0.080 mL, 0.633 mmol) and after 3 min with 2-aminoethanol (0.025 mL, 0.422 mmol)). The resulting mixture was stirred at room temperature for 5 h then EDC (48.5 mg, 0.253 mmol), N-ethyl morpholine (0.080 mL, 0.633 mmol), HOBT (38.8 mg, 0.253 mmol) and further 2-aminoethanol (0.025 mL, 0.422 mmol) were added and the corresponding mixture was stirred for 16 h then concentrated in vacuo. The residue was partitioned between water and EtOAc and the layers were separated. The aqueous phase was extracted with EtOAc (×2) and the combined organic layers were washed with saturated aqueous NaHCO₃ (×3), then brine, dried over MgSO₄ and concentrated in vacuo. The residue was purified by MDAP to give 4-((2S,4R)-1-acetyl-4-((5-cyanopyridin-2-yl)amino)-2-methyl-1,2,3,4-tetrahydroquinolin-6-yl)-N-(2-hydroxyethyl)benzamide (8 mg, 8%) as a white solid. LCMS (HpH, 2 min), Rt=0.78 min, MH+=470.

Example 15

4-((2S,4R)-1-acetyl-4-((5-cyanopyridin-2-yl)amino)-2-methyl-1,2,3,4-tetrahydroquinolin-6-yl)-N-(1,3-dihydroxypropan-2-yl)benzamide

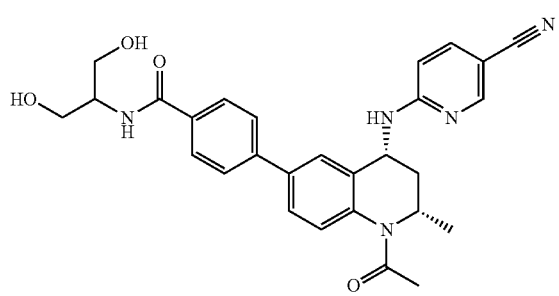 [SMILES: CC(=O)N1c2ccc(-c3ccc(C(=O)NC(CO)CO)cc3)cc2[C@H](Nc2ccc(C#N)cn2)C[C@@H]1C]

To a flask charged with 4-((2S,4R)-1-acetyl-4-((5-cyanopyridin-2-yl)amino)-2-methyl-1,2,3,4-tetrahydroquinolin-6-yl)benzoic acid (for a preparation see Intermediate 4) (90 mg, 0.211 mmol) and HATU (96 mg, 0.253 mmol) was added DMF (3 mL) and the resulting mixture was treated with DIPEA (0.111 mL, 0.633 mmol). After 5 min, the mixture was treated with 2-aminopropane-1,3-diol (38.5 mg, 0.422 mmol). The reaction mixture was stirred for 1 h, whereupon the bulk of solvent was removed and the residue was partitioned between EtOAc and saturated aqueous NaHCO₃. The phases were separated and the aqueous phase was extracted with EtOAc (×2). The combined organic layers were washed with saturated aqueous NaHCO₃ (×3), then brine, dried over MgSO₄ and concentrated in vacuo. The residue was purified by MDAP (HpH). The appropriate fractions were collected and concentrated in vacuo. The residue was dissolved in MeOH and dried (hydrophobic frit). The solvent was then removed in vacuo and the residue triturated with Et₂O to give 4-((2S,4R)-1-acetyl-4-((5-cyanopyridin-2-yl)amino)-2-methyl-1,2,3,4-tetrahydroquinolin-6-yl)-N-(1,3-dihydroxypropan-2-yl)benzamide (32 mg, 0.064 mmol, 30% yield) as a white solid. LCMS (HpH, 2 min), Rt=0.75 min, MH+=500.

Example 16

4-((2S,4R)-1-acetyl-4-((5-cyanopyridin-2-yl)amino)-2-methyl-1,2,3,4-tetrahydroquinolin-6-yl)-N-(2-(dimethylamino)ethyl)benzamide dihydrochloride

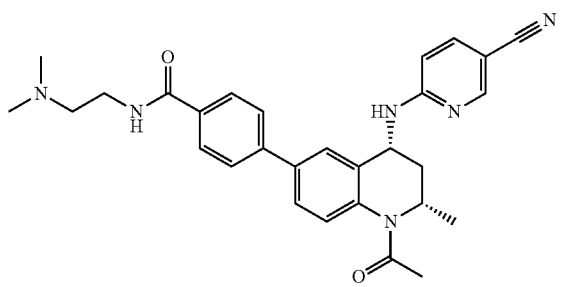

To a flask charged with 4-((2S,4R)-1-acetyl-4-((5-cyanopyridin-2-yl)amino)-2-methyl-1,2,3,4-tetrahydroquinolin-6-yl)benzoic acid (for a preparation see Intermediate 4)(100 mg, 0.234 mmol) and HATU (107 mg, 0.281 mmol) was added DMF (2 mL) and the resulting mixture was treated with DIPEA (0.123 mL, 0.703 mmol). After 5 min, N1,N1-dimethylethane-1,2-diamine (41.3 mg, 0.469 mmol) was added and the mixture was stirred for 30 min. The bulk of DMF was removed and the residue was partitioned between EtOAc and saturated aqueous NaHCO₃. The phases were separated and the organic layer was washed with saturated aqueous NaHCO₃, dried over MgSO₄ and concentrated in vacuo. The residue was purified by MDAP (HpH). The appropriate fractions were collected and concentrated in vacuo. The residue was co-evaporated with toluene, dissolved in 1,4-dioxane (4 mL) and subsequently treated with hydrogen chloride in 1,4-dioxane (4N, 1 ml). The resulting mixture was stirred for 5 min at room temperature and concentrated in vacuo. The obtained residue was triturated with Et₂O then dried under vacuum to give 4-((2S,4R)-1-acetyl-4-((5-cyanopyridin-2-yl)amino)-2-methyl-1,2,3,4-tetrahydroquinolin-6-yl)-N-(2-(dimethylamino)ethyl)benzamide, di hydrochloride (38 mg, 0.067 mmol, 28.5% yield) as a very pale yellow solid. LCMS (High pH, 2 min), Rt=0.87 min, MH+=497.

Example 17

4-((2S,4R)-1-Acetyl-4-((5-cyanopyridin-2-yl)amino)-2-methyl-1,2,3,4-tetrahydroquinolin-6-yl)-N-(2-aminoethyl)benzamide hydrochloride

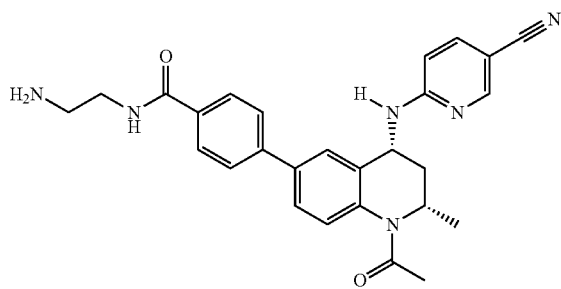 [SMILES: CC(=O)N1c2ccc(-c3ccc(C(=O)NCCN)cc3)cc2[C@H](Nc2ccc(C#N)cn2)C[C@@H]1C]

A suspension of tert-butyl (2-(4-((2S,4R)-1-acetyl-4-((5-cyanopyridin-2-yl)amino)-2-methyl-1,2,3,4-tetrahydroquinolin-6-yl)benzamido)ethyl)carbamate (for a preparation see Intermediate 39)(65 mg, 0.114 mmol) in 1,4-dioxane (1 mL) at room temperature was treated with hydrogen chloride in 1,4-dioxane (4N, 2 mL, 8.00 mmol) and the resulting suspension was stirred at this temperature for 1 h then concentrated in vacuo. The precipitate formed was triturated with Et₂O isolated by filtration and dried under vacuum to give 4-((2S,4R)-1-acetyl-4-((5-cyanopyridin-2-yl)amino)-2-methyl-1,2,3,4-tetrahydroquinolin-6-yl)-N-(2-aminoethyl)benzamide, hydrochloride (60 mg, 0.119 mmol, 104% yield) as a white solid. LCMS (HpH, 2 min), Rt=0.75 min, MH+=469.

Example 18

4-((2S,4R)-1-acetyl-2-methyl-4-(pyridin-2-ylamino)-1,2,3,4-tetrahydroquinolin-6-yl)-N-((S)-2,3-dihydroxypropyl)benzamide

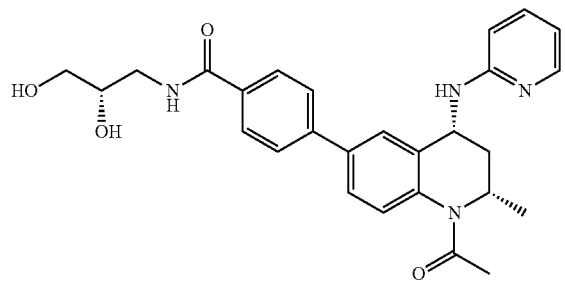 [SMILES: CC(=O)N1c2ccc(-c3ccc(C(=O)NC[C@H](O)CO)cc3)cc2[C@H](Nc2ccccn2)C[C@@H]1C]

A solution of 4-((2S,4R)-1-acetyl-2-methyl-4-(pyridin-2-ylamino)-1,2,3,4-tetrahydroquinolin-6-yl)benzoic acid (for a preparation see Intermediate 23) (70 mg, 0.174 mmol) in DMF (2 mL) was treated with EDC (40.1 mg, 0.209 mmol), HOBT (32.0 mg, 0.209 mmol) and N-ethylmorpholine (0.066 mL, 0.523 mmol) and after 3 min with (S)-3-aminopropane-1,2-diol (15.89 mg, 0.174 mmol). The resulting mixture was stirred at room temperature for 5 h then further EDC (40.1 mg, 0.209 mmol), N-ethylmorpholine (0.066 mL, 0.523 mmol), HOBT (32.0 mg, 0.209 mmol) and (S)-3-aminopropane-1,2-diol (15.89 mg, 0.174 mmol) were added and the mixture stirred for 16 h before concentrating in vacuo. The residue was partitioned between water and EtOAc and the layers were separated. The aqueous phase was extracted with EtOAc and the combined organic layers were washed with saturated aqueous NaHCO₃ (×3) then brine, dried over MgSO₄ and concentrated in vacuo. Trituration of the residue with Et₂O gave 4-((2S,4R)-1-acetyl-2-methyl-4-(pyridin-2-ylamino)-1,2,3,4-tetrahydroquinolin-6-yl)-N—((S)-2,3-dihydroxypropyl)benzamide (36 mg, 0.076 mmol, 43.5% yield) as a pale yellow solid.

LCMS (HpH, 2 min), Rt=0.76 min, MH+=475

The following analogues were prepared by using the above method with the appropriate amine:—

Example 19

4-((2S,4R)-1-acetyl-2-methyl-4-(pyridin-2-ylamino)-1,2,3,4-tetrahydroquinolin-6-yl)-N-(2-hydroxyethyl)benzamide

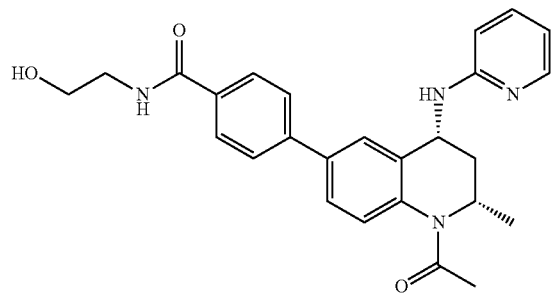 [SMILES: CC(=O)N1c2ccc(-c3ccc(C(=O)NCCO)cc3)cc2[C@H](Nc2ccccn2)C[C@@H]1C]

LC/MS (HpH, 2 min), Rt=0.78 min, MH+=445

Example 20

4-((2S,4R)-1-acetyl-2-methyl-4-(pyridin-2-ylamino)-1,2,3,4-tetrahydroquinolin-6-yl)-N-(2-(dimethylamino)ethyl)benzamide

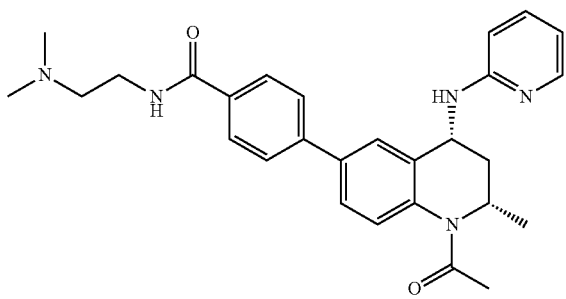 [SMILES: CC(=O)N1c2ccc(-c3ccc(C(=O)NCCN(C)C)cc3)cc2[C@H](Nc2ccccn2)C[C@@H]1C]

LC/MS (HpH, 2 min), Rt=0.89 min, MH+=472

Example 21

4-((2S,4R)-1-acetyl-2-methyl-4-(pyridin-2-ylamino)-1,2,3,4-tetrahydroquinolin-6-yl)-N-(1,3-dihydroxypropan-2-yl)benzamide

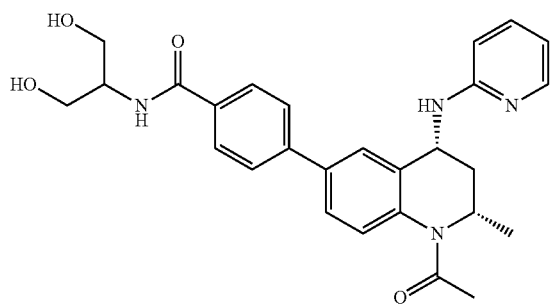 [SMILES: CC(=O)N1c2ccc(-c3ccc(C(=O)NC(CO)CO)cc3)cc2[C@H](Nc2ccccn2)C[C@@H]1C]

To a flask charged with 4-((2S,4R)-1-acetyl-2-methyl-4-(pyridin-2-ylamino)-1,2,3,4-tetrahydroquinolin-6-yl)benzoic acid (for a preparation see Intermediate 23) (70 mg, 0.174 mmol) and HATU (80 mg, 0.209 mmol) was added DMF (3 mL) and the resulting solution was treated with DIPEA (0.091 mL, 0.523 mmol) and after 5 min by 2-aminopropane-1,3-diol (31.8 mg, 0.349 mmol). The reaction was concentrated in vacuo, residue partitioned between water and EtOAc. the phases were separated and the aqueous extracted with EtOAc (×2). The combined organic layers were washed with saturated NaHCO₃ (3×) then brine, dried over MgSO₄ and concentrated in vacuo. The residue was purified by MDAP (HpH) and the residue triturated with Et₂O to give 4-((2S,4R)-1-acetyl-2-methyl-4-(pyridin-2-ylamino)-1,2,3,4-tetrahydroquinolin-6-yl)-N-(1,3-dihydroxypropan-2-yl)benzamide (17 mg, 0.036 mmol, 20.55% yield) as a very pale yellow solid. LCMS (HpH, 2 min), Rt=0.74 min, MH+=475.

The following analogue was prepared by using the above method with the appropriate amine:—

Example 22

4-((2S,4R)-1-acetyl-2-methyl-4-(pyridin-2-ylamino)-1,2,3,4-tetrahydroquinolin-6-yl)-N-(2-aminoethyl)benzamide

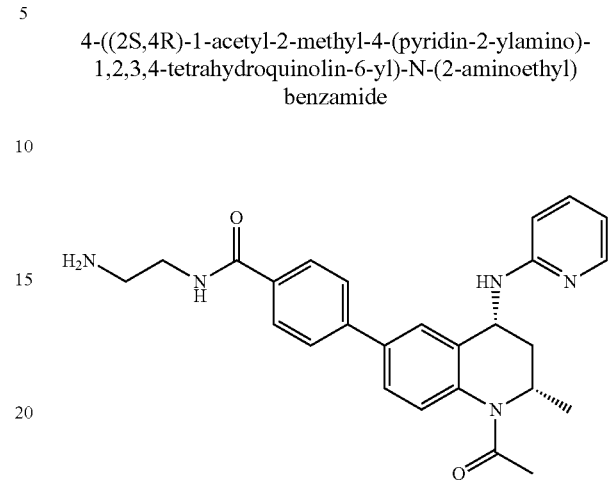

A suspension of tert-butyl (2-(4-((2S,4R)-1-acetyl-2-methyl-4-(pyridin-2-ylamino)-1,2,3,4-tetrahydroquinolin-6-yl)benzamido)ethyl)carbamate (for a preparation see Intermediate 40)(35 mg, 0.064 mmol) in 1,4-dioxane (1 mL) at room temperature was treated with hydrogen chloride in 1,4-dioxane (4N, 2 mL, 8.00 mmol) and the resulting suspension was stirred for 1 h at this temperature then concentrated in vacuo. The residue was triturated with Et₂O the solid isolated by filtration and dried under house vacuum to give 4-((2S,4R)-1-acetyl-2-methyl-4-(pyridin-2-ylamino)-1,2,3,4-tetrahydroquinolin-6-yl)-N-(2-aminoethyl)benzamide, hydrochloride (30 mg, 0.062 mmol, 97% yield) as a very pale yellow solid. LCMS (HpH, 2 min), Rt=0.74 min, MH+=444.

Example 23

6-((2S,4R)-1-acetyl-2-methyl-4-(pyridin-2-ylamino)-1,2,3,4-tetrahydroquinolin-6-yl)-N-(2-(dimethylamino)ethyl)nicotinamide

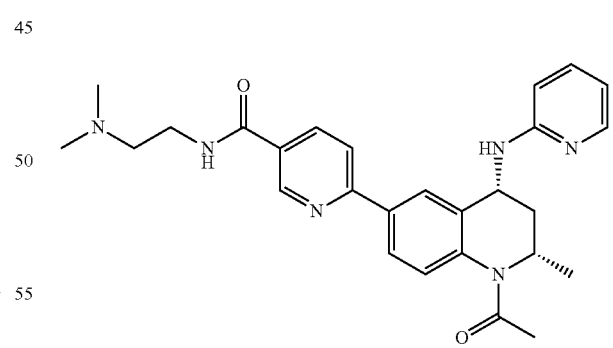

To a flask charged with 6-((2S,4R)-1-acetyl-2-methyl-4-(pyridin-2-ylamino)-1,2,3,4-tetrahydroquinolin-6-yl)nicotinic acid (for a preparation see Intermediate 28)(50 mg, 0.124 mmol) and HATU (56.7 mg, 0.149 mmol) was added DMF (2 mL) and the resulting mixture was treated with DIPEA (0.065 mL, 0.373 mmol) then after 5 min with N1,N1-dimethylethane-1,2-diamine (21.90 mg, 0.248 mmol). The resulting solution was stirred at room temperature for 30 min then partitioned between EtOAc and saturated NaHCO₃. The organic phase was separated and aqueous layer extracted with EtOAc (×2). The combined organic layers were washed with saturated NaHCO₃, dried over MgSO₄ and concentrated in vacuo. The residue divided into 2 portions and each was purified by MDAP (HpH). The appropriate fractions were collected and concentrated in vacuo. The residue was dissolved in MeOH and concentrated again, then co-evaporated with toluene. The residue were then dissolved in 1,4-dioxane (2 mL) and treated with hydrogen chloride in 1,4-dioxane (4N, 0.5 mL). After 2 min the solvent was evaporated in vacuo and the precipitate formed triturated with Et₂O then dried under house vacuum to give 6-((2S,4R)-1-acetyl-2-methyl-4-(pyridin-2-ylamino)-1,2,3,4-tetrahydroquinolin-6-yl)-N-(2-(dimethylamino)ethyl)nicotinamide, as the d-hydrochloride salt (37 mg, 0.068 mmol, 54.6% yield) as a yellow solid. LCMS (HpH, 2 min), Rt=0.81 min, MH+=473.

The following analogues were prepared by using the above method with the appropriate amine:—

Example 24

6-((2S,4R)-1-acetyl-2-methyl-4-(pyridin-2-ylamino)-1,2,3,4-tetrahydroquinolin-6-yl)-N-(2-hydroxyethyl)nicotinamide

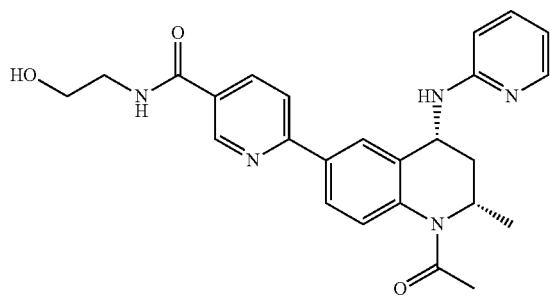 [SMILES: CC(=O)N1c2ccc(-c3ccc(C(=O)NCCO)cn3)cc2[C@H](Nc2ccccn2)C[C@@H]1C]

LCMS (HpH, 2 min), Rt=0.73 min, MH+=446.

Example 25

6-((2S,4R)-1-acetyl-2-methyl-4-(pyridin-2-ylamino)-1,2,3,4-tetrahydroquinolin-6-yl)-N-(1,3-dihydroxypropan-2-yl)nicotinamide

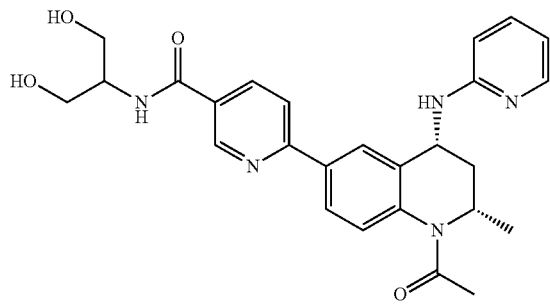 [SMILES: CC(=O)N1c2ccc(-c3ccc(C(=O)NC(CO)CO)cn3)cc2[C@H](Nc2ccccn2)C[C@@H]1C]

LCMS (HpH, 2 min), Rt=0.69 min, MH+=476.

Example 26

4-((2S,4R)-1-acetyl-2-methyl-4-(pyrimidin-2-ylamino)-1,2,3,4-tetrahydroquinolin-6-yl)-N-(2-(dimethylamino)ethyl)benzamide

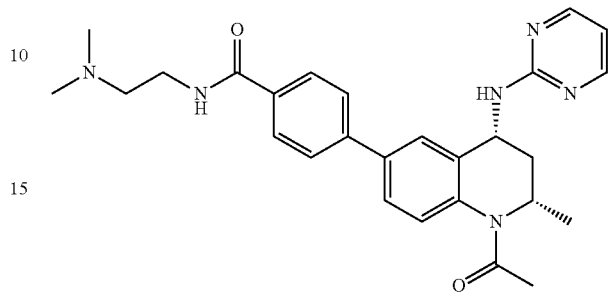

To a flask charged with 4-((2S,4R)-1-acetyl-4-amino-2-methyl-1,2,3,4-tetrahydroquinolin-6-yl)-N-(2-(dimethylamino)ethyl)benzamide (for a preparation see Intermediate 32) (197 mg, 0.5 mmol), 2-bromopyrimidine (238 mg, 1.500 mmol), sodium tert-butoxide (240 mg, 2.500 mmol), 2-(dimethylamino)-2'-(dicyclohexylphosphino)biphenyl (197 mg, 0.500 mmol) and tris(dibenzylideneacetone)dipalladium(0) (229 mg, 0.250 mmol) was added degassed toluene (4 mL) and the resulting mixture was stirred under nitrogen at 100° C. After 2 h the mixture was cooled to room temperature and most of the solvent was evaporated in vacuo. The residue was partitioned between EtOAc and saturated NaHCO₃ solution and the layers were separated. The aqueous phase was extracted with EtOAc and the combined organic phases were washed with saturated aqueous NaHCO₃ (×3), dried over MgSO₄ and concentrated in vacuo. The residue was dissolved in DCM and loaded on a SCX column (20 g). The cartridge was eluted with DCM then ammonia in MeOH (2N). The methanolic ammonia fractions were concentrated in vacuo and further purified on by chromatography (25 g column, elution with 2N ammonia in MeOH/DCM gradient) to give a residue which was dissolved in 1,4-dioxane (4 ml) and the solution treated with hydrogen chloride in 1,4-dioxane (4N, 0.5 mL). The precipitate which formed was isolated by filtration and dried at 60° C. under vacuum for 2 h to give 4-((2S,4R)-1-acetyl-2-methyl-4-(pyrimidin-2-ylamino)-1,2,3,4-tetrahydroquinolin-6-yl)-N-(2-(dimethylamino)ethyl) benzamide, hydrochloride (93 mg, 0.183 mmol, 36.5% yield) as a pale yellow solid. LCMS (HpH, 2 min), Rt=0.79 min, MH+=473.

Example 27

4-((2S,4R)-1-acetyl-2-methyl-4-(pyrazin-2-ylamino)-1,2,3,4-tetrahydroquinolin-6-yl)-N-(2-(dimethylamino)ethyl)benzamide

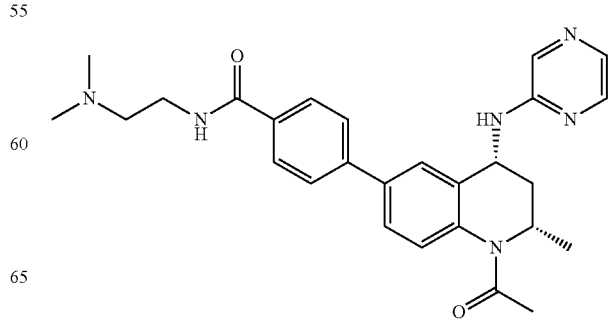

To a flask charged with 4-((2S,4R)-1-acetyl-4-amino-2-methyl-1,2,3,4-tetrahydroquinolin-6-yl)-N-(2-(dimethylamino)ethyl)benzamide (for a preparation see Intermediate 32) (197 mg, 0.5 mmol), sodium tert-butoxide (240 mg, 2.500 mmol), tris(dibenzylideneacetone)dipalladium(0) (229 mg, 0.250 mmol) and 2-(dimethylamino)-2'-(dicyclohexylphosphino)biphenyl (197 mg, 0.500 mmol) was added degassed toluene (4 mL). The resulting mixture was treated with 2-chloropyrazine (0.134 mL, 1.500 mmol) then stirred under nitrogen at 100° C. for ~45 min. The mixture was cooled to room temperature and most of the solvent was evaporated in vacuo. The residue was partitioned between EtOAc and a saturated NaHCO₃ solution and the layers were separated. The aqueous phase was extracted with EtOAc and the combined organic phases were washed with saturated aqueous NaHCO₃ (×3), dried over MgSO₄ and concentrated in vacuo. The residue was dissolved in DCM and loaded on a SCX column (20 g). The cartridge was eluted with DCM then with ammonia in MeOH (2N). The methanolic ammonia fractions were concentrated in vacuo and further purified by chromatography (25 g column, elution with 2N ammonia in MeOH/DCM gradient) to give a residue which was dissolved in 1,4-dioxane (4 ml). The solution was treated with hydrogen chloride in 1,4-dioxane (4N, 0.5 mL). The precipitate formed was isolated by filtration and dried at 60° C. under vacuum for 2 h to give 4-((2S,4R)-1-acetyl-2-methyl-4-(pyrimidin-2-ylamino)-1,2,3,4-tetrahydroquinolin-6-yl)-N-(2-(dimethylamino)ethyl)benzamide, Hydrochloride (93 mg, 0.183 mmol, 36.5% yield) as a white solid. LCMS (HpH, 2 min), Rt=0.79 min, MH+=473.

Example 28

5-((2S,4R)-1-acetyl-4-((5-cyanopyridin-2-yl)amino)-2-methyl-1,2,3,4 tetrahydroquinolin-6-yl)-N-(2-(dimethylamino)ethyl)picolinamide

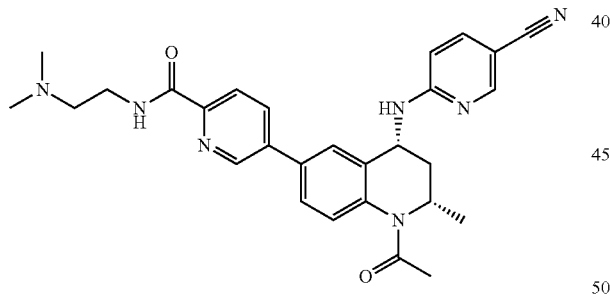

5-((2S,4R)-1-Acetyl-4-((5-cyanopyridin-2-yl)amino)-2-methyl-1,2,3,4-tetrahydroquinolin-6-yl)picolinic acid (for a preparation see Intermediate 34) (60 mg, 0.140 mmol) was dissolved in anhydrous DMF (3 ml) and HATU (64.0 mg, 0.168 mmol) was added. DIPEA (0.074 ml, 0.421 mmol) was added and after a further 5 min of stirring at r.t. N1,N1-dimethylethane-1,2-diamine (0.019 ml, 0.281 mmol) was added and reaction mixture stirred overnight at r.t. The reaction mixture was concentrated in vacuo and partitioned between EtOAc and water. The organic phase was separated, dried (Na₂SO₄) and concentrated to give a yellow residue which was purified by chromatography on a silica cartridge (10 g), eluting with a MeOH/DCM gradient (2-12%, over 120 mls) to give pale yellow solid (28 mg). This solid was treated with 1.1 equivalents of 1M hydrogen chloride in diethyl ether and the mixture triturated with diethyl ether to give yellow solid 5-((2S,4R)-1-acetyl-4-((5-cyanopyridin-2-yl)amino)-2-methyl-1,2,3,4-tetrahydroquinolin-6-yl)-N-(2-(dimethylamino)ethyl)picolinamide, hydrochloride (32 mg, 0.054 mmol, 38.4% yield).

LC/MS (Formic, 2 min), Rt=0.65 min, MH+=498.

The following analogues were prepared by using the above method with the appropriate amine:—

Example 29

5-((2S,4R)-1-acetyl-4-((5-cyanopyridin-2-yl)amino)-2-methyl-1,2,3,4-tetrahydroquinolin-6-yl)-N-(2-hydroxyethyl)picolinamide

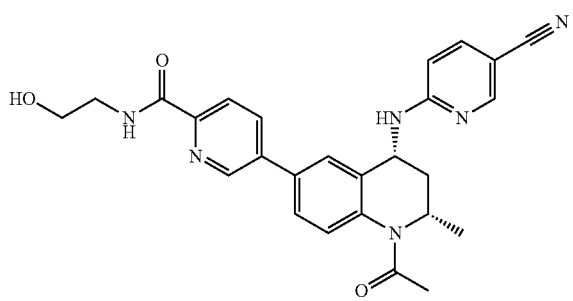 [SMILES: CC(=O)N1c2ccc(-c3ccc(C(=O)NCCO)nc3)cc2[C@H](Nc2ccc(C#N)cn2)C[C@@H]1C]

LCMS (Formate, 2 min), Rt=0.74 min, MH+=471

Example 30

5-((2S,4R)-1-acetyl-4-((5-cyanopyridin-2-yl)amino)-2-methyl-1,2,3,4tetrahydroquinolin-6-yl)-N-(1,3-dihydroxypropan-2-yl)picolinamide

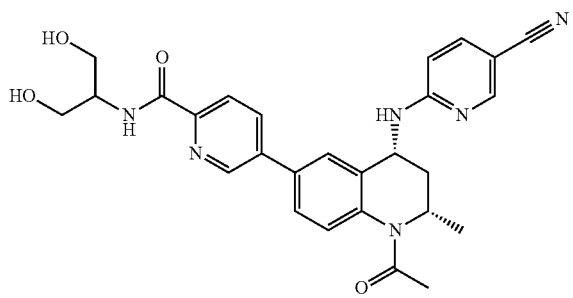 [SMILES: CC(=O)N1c2ccc(-c3ccc(C(=O)NC(CO)CO)nc3)cc2[C@H](Nc2ccc(C#N)cn2)C[C@@H]1C]

LCMS (Formate, 2 min), Rt=0.70 min, MH+=501

Example 31

5-((2S,4R)-1-acetyl-4-((5-cyanopyridin-2-yl)amino)-2-methyl-1,2,3,4-tetrahydroquinolin-6-yl)-N-(3-hydroxypropyl)picolinamide

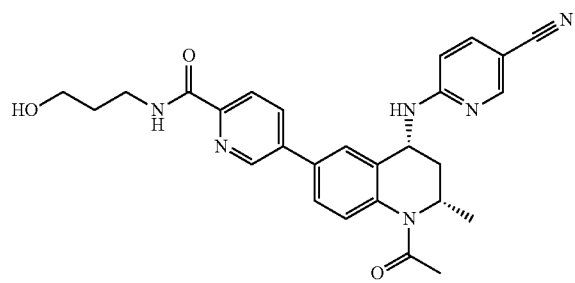 [SMILES: CC(=O)N1c2ccc(-c3ccc(C(=O)NCCCO)nc3)cc2[C@H](Nc2ccc(C#N)cn2)C[C@@H]1C]

LCMS (Formic, 2 min), Rt=0.77 min, MH+=485

Example 32

5-((2S,4R)-1-acetyl-4-((5-cyanopyridin-2-yl)amino)-2-methyl-1,2,3,4-tetrahydroquinolin-6-yl)-N—((R)-1-hydroxypropan-2-yl)picolinamide

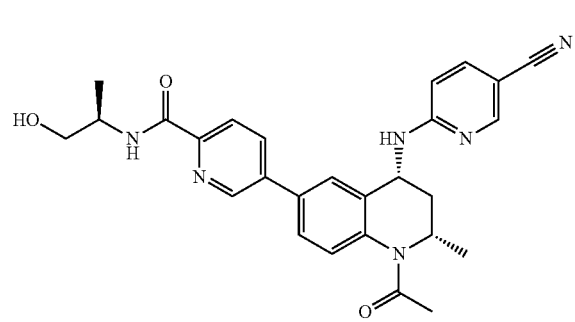 [SMILES: CC(=O)N1c2ccc(-c3ccc(C(=O)N[C@H](C)CO)nc3)cc2[C@H](Nc2ccc(C#N)cn2)C[C@@H]1C]

LCMS (Formate, 2 min), Rt=0.79 min, MH+=485

Example 33

6-(((2S,4R)-1-acetyl-6-(6-(3-hydroxypyrrolidine-1-carbonyl)pyridin-3-yl)-2-methyl-1,2,3,4-tetrahydroquinolin-4-yl)amino)nicotinonitrile

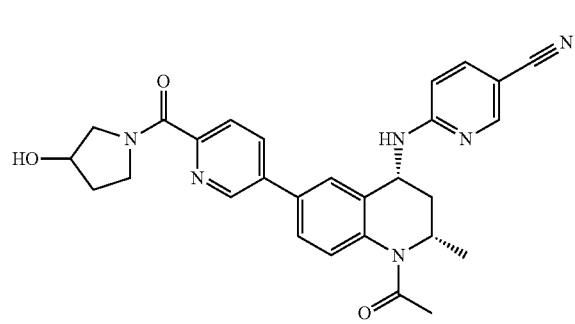 [SMILES: CC(=O)N1c2ccc(-c3ccc(C(=O)N4CCC(O)C4)nc3)cc2[C@H](Nc2ccc(C#N)cn2)C[C@@H]1C]

LCMS (Formate, 2 min), Rt=0.72 min, MH+=497

Example 34

6-(((2S,4R)-1-acetyl-2-methyl-6-(6-(4-methyl piperazine-1-carbonyl)pyridin-3-yl)-1,2,3,4-tetrahydroquinolin-4-yl)amino)nicotinonitrile

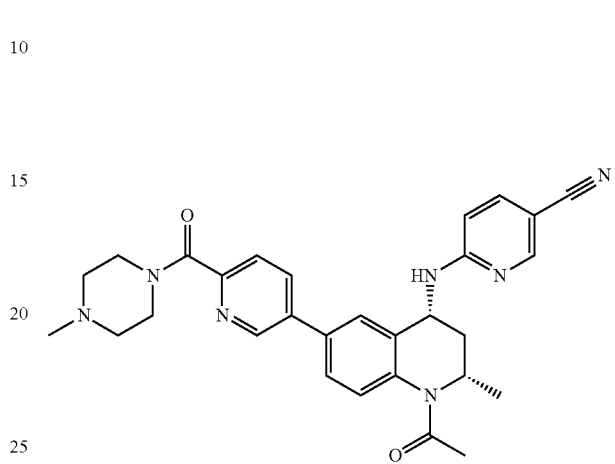

LCMS (Formate, 2 min), Rt=0.64 min, MH+=510

Example 35

6-(((2S,4R)-1-acetyl-6-(6-(4-hydroxypiperidine-1-carbonyl)pyridin-3-yl)-2-methyl-1,2,3,4-tetrahydroquinolin-4-yl)amino)nicotinonitrile

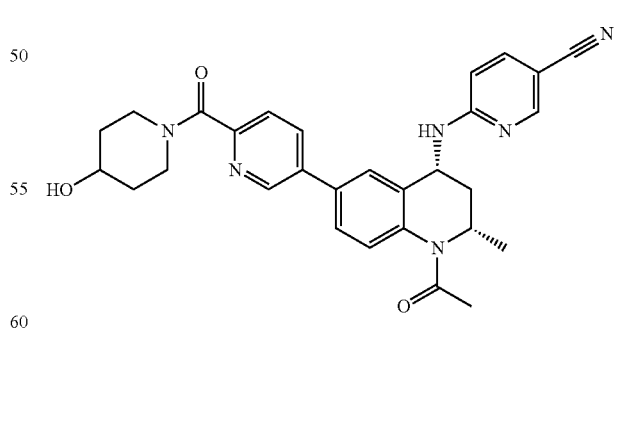

LCMS (Formate, 2 min), Rt=0.72 min, MH+=511

Example 36

6-(((2S,4R)-1-acetyl-6-(6-(4-aminopiperidine-1-carbonyl)pyridin-3-yl)-2-methyl-1,2,3,4-tetrahydroquinolin-4-yl)amino)nicotinonitrile

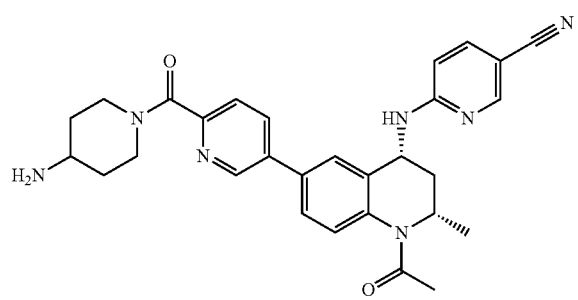 [SMILES: CC(=O)N1c2ccc(-c3ccc(C(=O)N4CCC(N)CC4)nc3)cc2[C@H](Nc2ccc(C#N)cn2)C[C@@H]1C]

tert-Butyl (1-(5-((2S,4R)-1-acetyl-4-((5-cyanopyridin-2-yl)amino)-2-methyl-1,2,3,4-tetrahydroquinolin-6-yl)picolinoyl)piperidin-4-yl)carbamate (for a preparation see Intermediate 43) (0.258 ml, 0.313 mmol) was dissolved in anhydrous DCM (4 ml). TFA (1 ml, 12.98 mmol) was added and the reaction mixture which was stirred under nitrogen at r.t. for 8 h. The reaction mixture was concentrated in vacuo and loaded onto a SCX cartridge (5 g, pre-conditioned with MeOH). The cartridge was washed with MeOH (40 ml) and eluted with ammonia in MeOH (2M). The methanolic ammonia fractions were concentrated to give an orange oil. The oil was further purified by chromatography on a silica cartridge (10 g), eluting with a MeOH/DCM gradient (2-12%, over 120 mls) followed by 10% of 2M NH3 in MeOH/DCM for 120 mls to give a pale orange solid. The solid was re-dissolved in MeOH (1 ml) and 1.1 equivalents of 1M hydrogen chloride in diethyl ether were added. The mixture was triturated with diethyl ether to give 6-(((2S,4R)-1-acetyl-6-(6-(4-aminopiperidine-1-carbonyl)pyridin-3-yl)-2-methyl-1,2,3,4-tetrahydroquinolin-4-yl)amino)nicotinonitrile, hydrochloride (19 mg, 0.030 mmol, 8.59% yield) as an orange solid. LCMS (Formate, 2 min), Rt=0.60 min, MH+=510.

The following analogues were prepared by using the above method:—

Example 37

6-(((2S,4R)-1-acetyl-6-(6-(3-aminoazetidine-1-carbonyl)pyridin-3-yl)-2-methyl-1,2,3,4-tetrahydroquinolin-4-yl)amino)nicotinonitrile

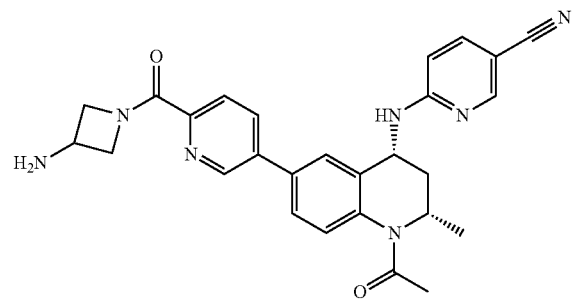 [SMILES: CC(=O)N1c2ccc(-c3ccc(C(=O)N4CC(N)C4)nc3)cc2[C@H](Nc2ccc(C#N)cn2)C[C@@H]1C]

LCMS (Formate, 2 min), Rt=0.60 min, MH+=482

Example 38

4-((2S,4R)-1-acetyl-4-((4-chlorophenyl)amino)-2-methyl-1,2,3,4-tetrahydroquinolin-6-yl)-N-(2-(dimethylamino)ethyl)benzamide

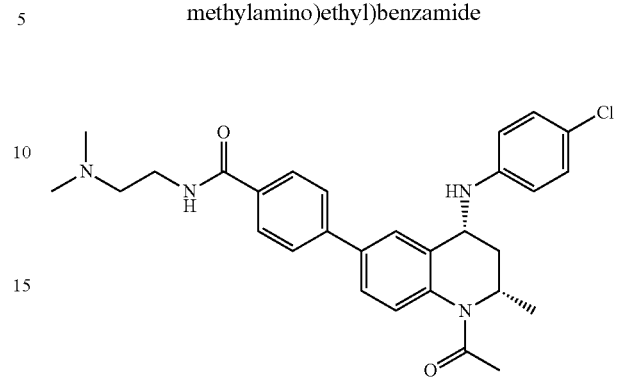

4-{(2S,4R)-1-acetyl-4-[(4-chlorophenyl)amino]-2-methyl-1,2,3,4-tetrahydro-6-quinolinyl}benzoic acid (for a preparation see Intermediate 18) (150 mg, 0.345 mmol) was suspended in DCM (3 mL) and DMAP (51.5 mg, 0.422 mmol) then DCC (78.8 mg, 0.382 mmol) added. The reaction was stirred for 5 min before N,N-dimethyl-ethylenediamine (33.4 mg, 0.379 mmol) in DCM (0.5 mL) was added. The reaction was stirred at room temperature overnight. The reaction was concentrated in vacuo. The residue was taken up in the minimum volume of 5% MeOH in DCM and applied to a 25 g cartridge and allowed to dry in the vac oven at 40° C. for 30 min. The cartridge was eluted with 1% 2M ammonia in Methanol in DCM for 2CV then 1-10% 2M ammonia in Methanol over 10CV then held at 10% for 5CV. The product was isolated as a yellow solid which was further purified by MDAP (HpH). The product containing fractions were concentrated in vacuo. The residue was taken up in the minimum volume of MeOH and applied to a SCX cartridge (5 g) which was eluted with MeOH (20 mL) then ammonia in MeOH (2M, 20 mL). The ammonia fraction was concentrated in vacuo to yield a clear oil. (85.8 mg, 0.17 mmol). This was taken up in the minimum volume of DCM and 1.1 eq 1M HCl in Et$_2$O (0.19 ml) was added. The solvent was removed under a stream of nitrogen and Et$_2$O(~2 ml) added to the residue then removed under a stream of nitrogen to yield 4-{(2S,4R)-1-acetyl-4-[(4-chlorophenyl)amino]-2-methyl-1,2,3,4-tetrahydro-6-quinolinyl}-N42-(dimethylamino)ethypenzamide hydrochloride (77.2 mg, 0.140 mmol, 40.7% yield) as a white solid. LCMS (Formate, 2 min), Rt=0.85 min, MH+=505.

Example 39

4-((2S,4R)-1-acetyl-4-((4-chlorophenyl)amino)-2-methyl-1,2,3,4-tetrahydroquinolin-6-yl)-N-(1,3-dihydroxypropan-2-yl)benzamide

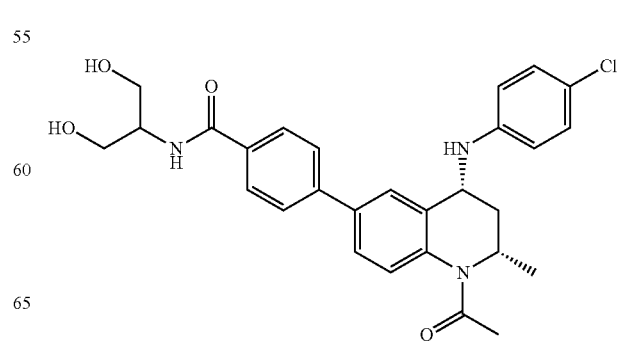

A flask was charged with 4-{(2S,4R)-1-acetyl-4-[(4-chlorophenyl)amino]-2-methyl-1,2,3,4-tetrahydro-6-quinolinyl}benzoic acid (for a preparation see Intermediate 18) (109 mg, 0.25 mmol), HOBT (45.9 mg, 0.300 mmol) and EDC (57.5 mg, 0.300 mmol) DCM (5 mL) added and the resulting mixture treated with N-ethylmorpholine (0.095 mL, 0.750 mmol). After 5 min, the pale yellow solution was treated with 2-amino-1,3-propanediol (29.6 mg, 0.325 mmol) and the mixture stirred at room temperature. After 4 h further portions of HOBT (22.95 mg, 0.150 mmol), EDC (28.75 mg, 0.150 mmol) and N-ethylmorpholine (0.0475 mL, 0.375 mmol) were added and reaction mixture stirred overnight at r.t. The volatiles were evaporated in vacuo and the residue dissolved in EtOAc and water. The layers were separated and the aqueous phase extracted with EtOAc. The combined organic phases were washed with saturated aqueous $NaHCO_3$ (×2), then brine, dried over $MgSO_4$ and concentrated in vacuo. The residue was purified by chromatography eluting with a MeOH/DCM gradient to give 4-{(2S,4R)-1-acetyl-4-[(4-chlorophenyl)amino]-2-methyl-1,2,3,4-tetrahydro-6-quinolinyl}-N-[2-hydroxy-1-(hydroxymethyl)ethy]penzamide (66 mg, 0.130 mmol, 52% yield) as a pale yellow foam. LCMS (HpH, 2 min), Rt=0.95 min, MH+=508.

The following analogues were prepared by using the above method using the appropriate amine:—

Example 40

4-((2S,4R)-1-acetyl-4-((4-chlorophenyl)amino)-2-methyl-1,2,3,4-tetrahydroquinolin-6-yl)-N-(2-hydroxyethyl)benzamide

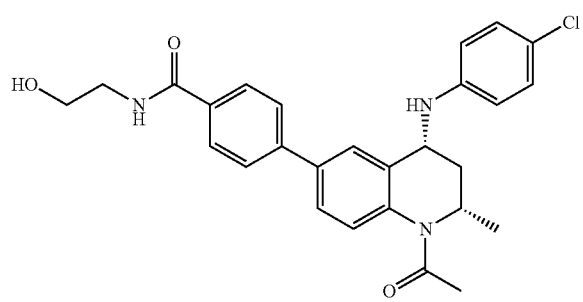 [SMILES: CC(=O)N1c2ccc(-c3ccc(C(=O)NCCO)cc3)cc2[C@H](Nc2ccc(Cl)cc2)C[C@@H]1C]

LCMS (H pH, 2 min), Rt=1.00 min, MH+=478

Example 41

4-((2S,4R)-1-acetyl-4-((4-chlorophenyl)amino)-2-methyl-1,2,3,4-tetrahydroquinolin-6-yl)-N—((R)-2-hydroxypropyl)benzamide

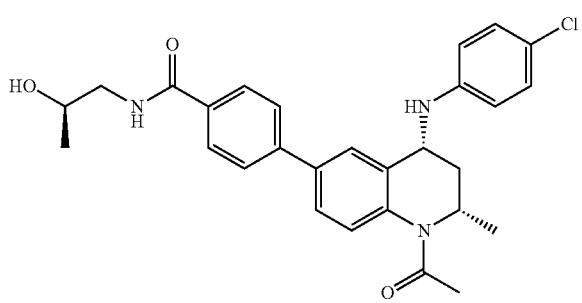 [SMILES: CC(=O)N1c2ccc(-c3ccc(C(=O)NC[C@@H](C)O)cc3)cc2[C@H](Nc2ccc(Cl)cc2)C[C@@H]1C]

LCMS (High pH, 2 min), Rt=1.03 min, MH+=492

Example 42

4-((2S,4R)-1-acetyl-4-((4-chlorophenyl)amino)-2-methyl-1,2,3,4-tetrahydroquinolin-6-yl)-N—((S)-2-hydroxypropyl)benzamide LCMS (HpH, 2 min), Rt=1.03 min, MH−=490

Example 43

4-((2S,4R)-1-acetyl-4-((4-chlorophenyl)amino)-2-methyl-1,2,3,4-tetrahydroquinolin-6-yl)-N—((S)-2,3-dihydroxypropyl)benzamide

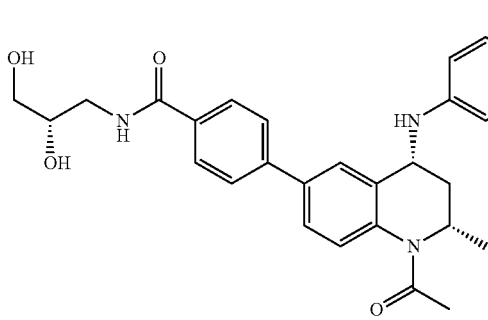

LCMS (HpH, 2 min), Rt=0.95 min, MH+=508

Example 44

4-((2S,4R)-1-acetyl-4-((4-chlorophenyl)amino)-2-methyl-1,2,3,4-tetrahydroquinolin-6-yl)-N-(2-aminoethyl)benzamide

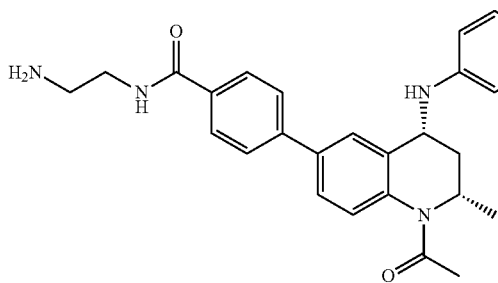

A solution of 1,1-dimethylethyl (2-{[(4-{(2S,4R)-1-acetyl-4-[(4-chlorophenyl)amino]-2-methyl-1,2,3,4-tetrahydro-6-quinolinyl}phenyl)carbonyl]amino}ethyl)carbamate (for a preparation see Intermediate 45) (57 mg, 0.099 mmol) in 1,4-dioxane (0.5 mL) at room temperature was treated with hydrogen chloride in 1,4-dioxane (2 mL, 8.0 mmol) and the resulting mixture was stirred at room temperature for 1.5 h then concentrated in vacuo. The residue was co-evaporated with Et$_2$O to give 4-{(2S,4R)-1-acetyl-4-[(4-chlorophenyl)amino]-2-methyl-1,2,3,4-tetrahydro-6-quinolinyl}-N-(2-aminoethyl)benzamide (32.5 mg, 0.063 mmol, 64.1% yield) hydrochloride as a pale yellow solid. LCMS (HpH, 2 min), Rt=1.01 min, MH+=477.

Example 45

4-((2S,4R)-1-acetyl-2-methyl-4-(phenylamino)-1,2,3,4-tetrahydroquinolin-6-yl)-N-(2-(dimethylamino)ethyl)benzamide

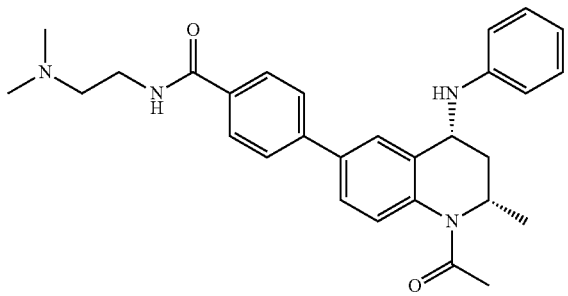 [SMILES: CC(=O)N1c2ccc(-c3ccc(C(=O)NCCN(C)C)cc3)cc2[C@H](Nc2ccccc2)C[C@@H]1C]

4-((2S,4R)-1-Acetyl-2-methyl-4-(phenylamino)-1,2,3,4-tetrahydroquinolin-6-yl)benzoic acid (for a preparation see Intermediate 35) (90 mg, 0.225 mmol) was dissolved in anhydrous DMF (3 ml and HATU (103 mg, 0.270 mmol) added. DIPEA (0.118 ml, 0.674 mmol) was added to the mixture and after a further 5 min of stirring at r.t. N1,N1-dimethylethane-1,2-diamine (0.030 ml, 0.449 mmol). The reaction mixture was stirred at r.t. overnight, concentrated and partitioned between EtOAc and water. The Organic phase was separated, dried (Na$_2$SO$_4$) and concentrated. The yellow residue was purified by chromatography a silica cartridge (10 g), eluting with MeOH/DCM (1-6% over 120 mls, followed by 6-20% over 120 mls) to give 4-((2S,4R)-1-acetyl-2-methyl-4-(phenylamino)-1,2,3,4-tetrahydroquinolin-6-yl)-N-(2(dimethylamino)ethyl)benzamide (24 mg, 0.05 mmol, 20% yield) as a light brown solid. LCMS (Formic, 2 min), Rt=0.79 min, MH+=471.

Analogues prepared by the above method using the appropriate amine:—

Examples 46

4-((2S,4R)-1-acetyl-2-methyl-4-(phenylamino)-1,2,3,4-tetrahydroquinolin-6-yl)-N-(2-hydroxyethyl)benzamide

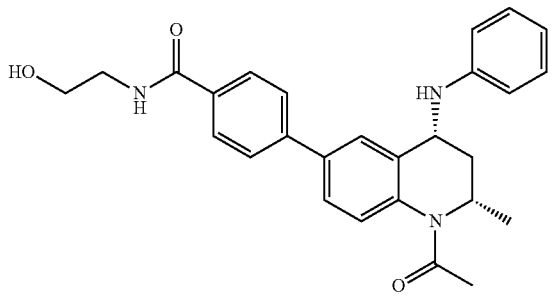 [SMILES: CC(=O)N1c2ccc(-c3ccc(C(=O)NCCO)cc3)cc2[C@H](Nc2ccccc2)C[C@@H]1C]

LCMS (Formate, 2 min), Rt=0.88 min, MH+=444

Example 47

4-((2S,4R)-1-acetyl-2-methyl-4-(phenylamino)-1,2,3,4-tetrahydroquinolin-6-yl)-N-(1,3-dihydroxypropan-2-yl)benzamide

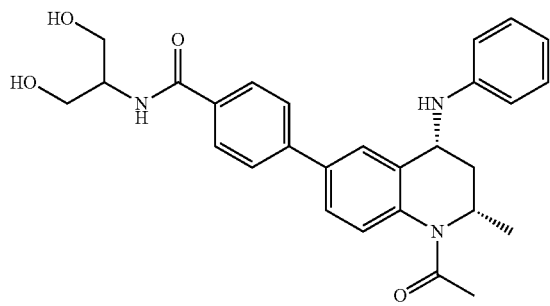 [SMILES: CC(=O)N1c2ccc(-c3ccc(C(=O)NC(CO)CO)cc3)cc2[C@H](Nc2ccccc2)C[C@@H]1C]

LCMS (Formate, 2 min), Rt=0.82 min, MH+=474.

Example 48

6-(((2S,4R)-1-acetyl-2-methyl-6-(6-(piperazine-1-carbonyl)pyridin-3-yl)-1,2,3,4-tetrahydroquinolin-4-yl)amino)nicotinonitrile

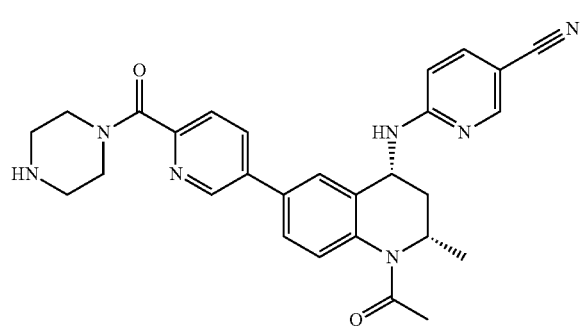 [SMILES: CC(=O)N1c2ccc(-c3ccc(C(=O)N4CCNCC4)nc3)cc2[C@H](Nc2ccc(C#N)cn2)C[C@@H]1C]

tert-Butyl 4-(5-((2S,4R)-1-acetyl-4-((5-cyanopyridin-2-yl)amino)-2-methyl-1,2,3,4-tetrahydroquinolin-6-yl)picolinoyl)piperazine-1-carboxylate (for a preparation see Intermediate 44) (205 mg, 0.344 mmol), was dissolved in anhydrous DCM (4 ml). TFA (1 ml, 12.98 mmol) was added to each reaction mixture, which was stirred under nitrogen at r.t. for 7.5 h. The reaction mixture was concentrated and loaded onto an SCX cartridge (5 g, pre-conditioned with MeOH). The cartridge was washed with MeOH (40 ml) followed by ammonia in MeOH (2M). and the methanolic ammonia fraction concentrated. The residue was loaded onto a silica cartridge (10 g) and the cartridge washed with 10% MeOH/DCM followed by 10% 2M ammonia in MeOH/DCM. The appropriate fractions were concentrated, the residue re-dissolved in MeOH (1 ml) treated with 1.1 equivalents of hydrogen chloride in diethyl ether (1M). Trituration with ether gave 4-((2S,4R)-1-acetyl-2-methyl-4-(phenylamino)-1,2,3,4-tetrahydroquinolin-6-yl)-N-(1,3-dihydroxypropan-2-yl)benzamide. hydrochloride as an orange solid (57 mg, 26.5%). LCMS (formate, 2 min) Rt=0.60 mins, 83%, MH+ at 496

Example 49

5-((2S,4R)-1-acetyl-4-((5-cyanopyrazin-2-yl)amino)-2-methyl-1,2,3,4-tetrahydroquinolin-6-yl)-N-(2-hydroxyethyl)picolinamide

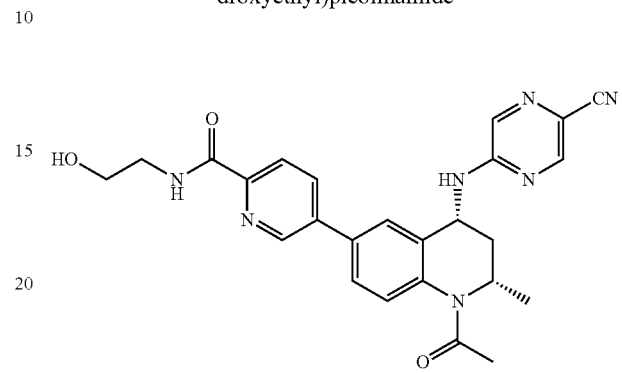

5-((2S,4R)-1-acetyl-4-((5-cyanopyrazin-2-yl)amino)-2-methyl-1,2,3,4-tetrahydroquinolin-6-yl)picolinic acid (for a preparation see Intermediate 53) (100 mg, 0.233 mmol), HATU (177 mg, 0.467 mmol) and DIPEA (0.122 ml, 0.700 mmol) were combined in DMF (3 mL) and stirred at room temperature for 10 mins. 2-aminoethanol (0.029 ml, 0.350 mmol) was added and the reaction mixture stirred for 1.5 h. The mixture was concentrated in vacuo and purified by MDAP (formate) to give 5-((2S,4R)-1-acetyl-4-((5-cyanopyrazin-2-yl)amino)-2-methyl-1,2,3,4-tetrahydroquinolin-6-yl)-N-(2-hydroxyethyl)picolinamide (42 mg, 0.089 mmol, 38% yield). LCMS: (Formate, 2 min), Rt=0.73 mins, MH+=472

Example 50

1-((2S,4R)-2-methyl-6-(6-(morpholine-4-carbonyl)pyridin-3-yl)-4-(pyridin-2-ylamino)-3,4-dihydroquinolin-1(2H)-yl)ethanone

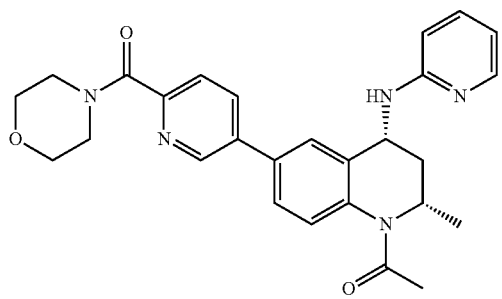 [SMILES: CC(=O)N1c2ccc(-c3ccc(C(=O)N4CCOCC4)nc3)cc2[C@H](Nc2ccccn2)C[C@@H]1C]

1-((2S,4R)-4-amino-2-methyl-6-(6-(morpholine-4-carbonyl)pyridin-3-yl)-3,4-dihydroquinolin-1(2H)-yl)ethanone (for a preparation see Intermediate 56) (40 mg, 0.101 mmol), 2-bromopyridine (0.019 mL, 0.203 mmol), 2'-(dicyclohexylphosphino)-N,N-dimethyl-[1,1'-biphenyl]-2-amine (8.0 mg, 0.020 mmol), tris(dibenzylideneacetone)dipalladium(0) (9.3 mg, 10.1 μmol) and sodium tert-butoxide (19.5 mg, 0.203 mmol) were combined in 1,4-dioxane (1 mL), degassed over a period of 15 mins and heated under microwave irradiation to 120° C. for 25 mins. A further portion of tris(dibenzylideneacetone)dipalladium(0) (9.3 mg, 10.1 μmol) was added, the reaction degassed, and the mixture heated under microwave irradiation to 120° C. for 20 mins.

In a separate vial, 1-((2S,4R)-4-amino-2-methyl-6-(6-(morpholine-4-carbonyl)pyridin-3-yl)-3,4-dihydroquinolin-1(2H)-yl)ethanone (for a preparation see Intermediate 56) (25 mg, 0.063 mmol), 2-bromopyridine (0.012 mL, 0.127 mmol), 2'-(dicyclohexylphosphino)-N,N-dimethyl-[1,1'-biphenyl]-2-amine (5.0 mg, 0.013 mmol), tris(dibenzylideneacetone)dipalladium(0) (5.8 mg, 6.34 μmol) and sodium tert-butoxide (12.2 mg, 0.127 mmol) were combined in 1,4-dioxane (1 mL), degassed over a period of 15 mins and heated under microwave irradiation to 120° C. for 25 mins.

The two crude reaction mixtures were combined and partitioned between saturated aq. sodium bicarbonate (50 mL) and DCM (3×50 mL). The organics were combined, dried by passing through a hydrophobic frit and concentrated in vacuo. The residue was purified by MDAP (HpH) to give 1-((2S,4R)-2-methyl-6-(6-(morpholine-4-carbonyl)pyridin-3-yl)-4-(pyridin-2-ylamino)-3,4-dihydroquinolin-1(2H)-yl)ethanone (36 mg, 0.076 mmol, 75% yield). LCMS: (Formate, 2 min), Rt=0.56 mins, MH+=472.

Example 51

1-((2S,4R)-2-methyl-4-((5-methylpyridin-2-yl)amino)-6-(6-(morpholine-4-carbonyl)pyridin-3-yl)-3,4-dihydroquinolin-1(2H)-yl)ethanone

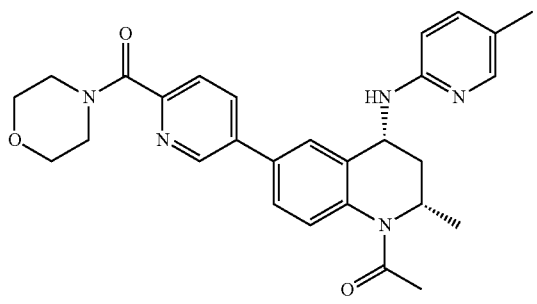

1-((2S,4R)-4-amino-2-methyl-6-(6-(morpholine-4-carbonyl)pyridin-3-yl)-3,4-dihydroquinolin-1(2H)-yl)ethanone (for a preparation, see Intermediate 56) (80 mg, 0.203 mmol), 2-bromo-5-methylpyridine (69.8 mg, 0.406 mmol), 2'-(dicyclohexylphosphino)-N,N-dimethyl-[1,1'-biphenyl]-2-amine (16.0 mg, 0.041 mmol), tris(dibenzylideneacetone)dipalladium(0) (18.6 mg, 0.020 mmol) and sodium tert-butoxide (39.0 mg, 0.406 mmol) were combined in 1,4-dioxane (2 mL). The mixture was degassed over a period of 15 mins before being heated under microwave irradiation to 120° C. for 30 mins. The mixture was partitioned between saturated aq. sodium bicarbonate (50 mL) and DCM (3×50 mL). The organic layers were combined, dried by passing through a hydrophobic frit and concentrated in vacuo. The resulting residue was purified by MDAP (HpH) to give 1-((2S,4R)-2-methyl-4-((5-methylpyridin-2-yl)amino)-6-(6-(morpholine-4-carbonyl)pyridin-3-yl)-3,4-dihydroquinolin-1(2H)-yl) ethanone (13 mg, 0.027 mmol, 13% yield) as an off-white solid. LCMS: (Formate, 2 min), Rt=0.58 mins, MH+=486.

Example 52

1-((2S,4R)-4-((5-chloropyridin-2-yl)amino)-2-methyl-6-(6-(morpholine-4-carbonyl)pyridin-3-yl)-3,4-dihydroquinolin-1(2H)-yl)ethanone

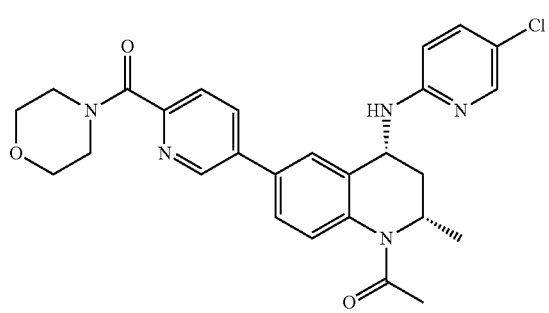 [SMILES: CC(=O)N1c2ccc(-c3ccc(C(=O)N4CCOCC4)nc3)cc2[C@H](Nc2ccc(Cl)cn2)C[C@@H]1C]

1-((2S,4R)-4-amino-2-methyl-6-(6-(morpholine-4-carbonyl)pyridin-3-yl)-3,4-dihydroquinolin-1(2H)-yl)ethanone (for a preparation, see Intermediate 56) (80 mg, 0.203 mmol), 2-bromo-5-chloropyridine (78 mg, 0.406 mmol), 2'-(dicyclohexylphosphino)-N,N-dimethyl-[1,1'-biphenyl]-2-amine (16.0 mg, 0.041 mmol), tris(dibenzylideneacetone)dipalladium(0) (18.6 mg, 0.020 mmol) and sodium tert-butoxide (27.3 mg, 0.284 mmol) were combined in 1,4-dioxane (1 mL). The mixture was degassed over a period of 15 mins before being heated under microwave irradiation to 120° C. for 15 mins. The mixture was partitioned between saturated aq. sodium bicarbonate (50 mL) and DCM (3×50 mL). The organic layers were combined, dried by passing through a hydrophobic frit and concentrated in vacuo. The resulting residue was purified by MDAP (HpH) to give 1-((2S,4R)-4-((5-chloropyridin-2-yl)amino)-2-methyl-6-(6-(morpholine-4-carbonyl)pyridin-3-yl)-3,4-dihydroquinolin-1(2H)-yl)ethanone (54 mg, 0.107 mmol, 53% yield). LCMS: (Formate, 2 min), Rt=0.86 mins, MH+=506.

Example 53

1-((2S,4R)-2-methyl-6-(6-(morpholine-4-carbonyl)pyridin-3-yl)-4-(pyrazin-2-ylamino)-3,4-dihydroquinolin-1(2H)yl)ethanone

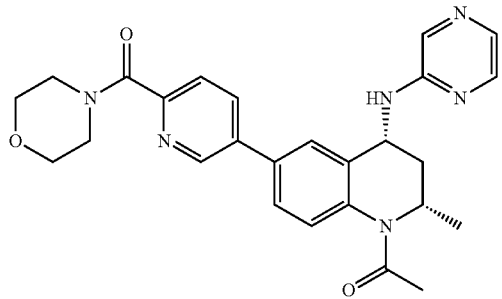 [SMILES: CC(=O)N1c2ccc(-c3ccc(C(=O)N4CCOCC4)nc3)cc2[C@H](Nc2cnccn2)C[C@@H]1C]

1-((2S,4R)-4-amino-2-methyl-6-(6-(morpholine-4-carbonyl)pyridin-3-yl)-3,4-dihydroquinolin-1(2H)-yl)ethanone (for a preparation, see Intermediate 56) (80 mg, 0.203 mmol), 2-chloropyrazine (0.036 mL, 0.406 mmol), 2'-(dicyclohexylphosphino)-N,N-dimethyl-[1,1'-biphenyl]-2-amine (16.0 mg, 0.041 mmol), tris(dibenzylideneacetone)dipalladium(0) (18.6 mg, 0.020 mmol) and sodium tert-butoxide (27.3 mg, 0.284 mmol) were dissolved in 1,4-dioxane (2 mL). The mixture was degassed over a period of 15 mins before being heated under microwave irradiation to 120° C. for 25 mins. The mixture was partitioned between saturated aq. sodium bicarbonate (50 mL) and DCM (3×50 mL). The organic layers were combined, dried by passing through a hydrophobic frit and concentrated in vacuo. The resulting residue was purified by MDAP (HpH) to give 1-((2S,4R)-2-methyl-6-(6-(morpholine-4-carbonyl)pyridin-3-yl)-4-(pyrazin-2-ylamino)-3,4-dihydroquinolin-1(2H)-yl)ethanone (50 mg, 0.106 mmol, 52% yield).

LCMS: (Formate, 2 min), Rt=0.68 mins, MH+=473.

Example 54

1-((2S,4R)-2-methyl-4-((5-methylpyrazin-2-yl)amino)-6-(6-(morpholine-4-carbonyl)pyridin-3-yl)-3,4-dihydroquinolin-1(2H)-yl)ethanone

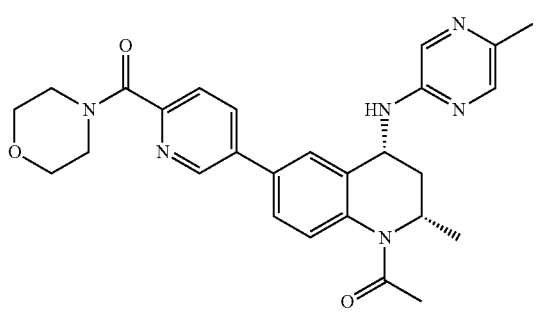 [SMILES: CC(=O)N1c2ccc(-c3ccc(C(=O)N4CCOCC4)nc3)cc2[C@H](Nc2cnc(C)cn2)C[C@@H]1C]

1-((2S,4R)-4-amino-2-methyl-6-(6-(morpholine-4-carbonyl)pyridin-3-yl)-3,4-dihydroquinolin-1(2H)-yl)ethanone (for a preparation, see Intermediate 56) (80 mg, 0.203 mmol), 2-bromo-5-methylpyrazine (70.2 mg, 0.406 mmol), 2'-(dicyclohexylphosphino)-N,N-dimethyl-[1,1-biphenyl]-2-amine (16.0 mg, 0.041 mmol), tris(dibenzylideneacetone)dipalladium(0) (18.6 mg, 0.020 mmol) and sodium tert-butoxide (27.3 mg, 0.284 mmol) were combined in 1,4-dioxane (2 mL). The mixture was degassed over a period of 15 mins before being heated under microwave irradiation to 120° C. for 25 mins. The mixture was partitioned between saturated aq. sodium bicarbonate (50 mL) and DCM (3×50 mL). The organic layers were combined, dried by passing through a hydrophobic frit and concentrated in vacuo. The resulting residue was purified by MDAP (HpH) followed by further purification by MDAP (Formate) to give 1-((2S,4R)-2-methyl-4-((5-methylpyrazin-2-yl)amino)-6-(6-(morpholine-4-carbonyl)pyridin-3-yl)-3,4-dihydroquinolin-1(2H)-yl)ethanone (26 mg, 0.053 mmol, 26% yield).

LCMS: (Formate, 2 min), Rt=0.71 mins, MH+=487.

Example 55

1-((2S,4R)-2-methyl-6-(4-(morpholine-4-carbonyl)phenyl)-4-(pyridin-2-ylamino)-3,4-dihydroquinolin-1(2H)-yl)ethanone formate

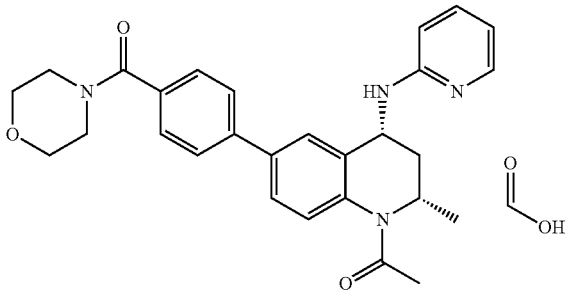

Crude lithium 4-((2S,4R)-1-acetyl-2-methyl-4-(pyridin-2-ylamino)-1,2,3,4-tetrahydroquinolin-6-yl)benzoate (for a preparation see Intermediate 58) (40 mg) and HATU (41 mg, 0.108 mmol) in DMF (0.5 mL) were treated with DIPEA (51.2 µL, 0.294 mmol) and the mixture shaken and sonicated until a solution was formed (<2 min). This solution was added to morpholine (17 µL, 0.194 mmol), the mixture briefly shaken then left to stand at room temperature for 2 h. A further portion of morpholine (34 µL, 0.388 mmol) was added and the mixture left to stand overnight. The mixture was diluted with water and extracted three times with DCM. The combined organic layers were dried by passing through a hydrophobic frit and concentrated in vacuo to give a residue. The residue was purified by MDAP (formate) to give 1-((2S,4R)-2-methyl-6-(4-(morpholine-4-carbonyl)phenyl)-4-(pyridin-2-ylamino)-3,4-dihydroquinolin-1(2H)-yl)ethanone formate (20 mg, 0.039 mmol, 10% yield) as a pale pink glass.

LCMS: (Formate, 2 min), Rt 0.63 min, MH+471.

Example 56

1-((2S,4R)-2-methyl-4-((5-methylpyridin-2-yl)amino)-6-(4-(morpholine-4-carbonyl)phenyl)-3,4-dihydroquinolin-1(2H)-yl)ethanone formate

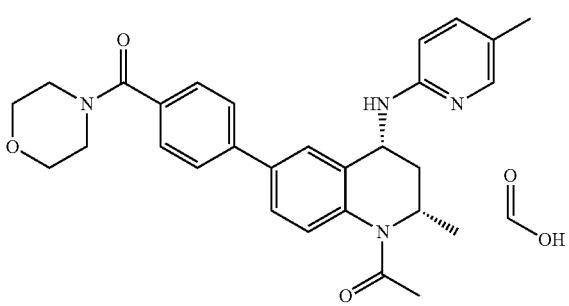

A mixture of crude lithium 4-((2S,4R)-1-acetyl-2-methyl-4-((5-methylpyridin-2-yl)amino)-1,2,3,4-tetrahydroquinolin-6-yl)benzoate (for a preparation see Intermediate 60) (48 mg) and HATU (48 mg, 0.316 mmol) in DMF (0.5 mL) was treated with DIPEA (0.06 mL, 0.344 mmol) and the mixture stirred at room temperature for 5 min to give a solution which was added to morpholine (51 µL, 0.583 mmol). The mixture was shaken briefly and then left at room temperature overnight. The resulting solution was diluted with water to and left to stand for ~10 min. The resultant precipitate was isolated by filtration and washed with water. The isolated precipitate was dissolved in MeOH concentrated to dryness to give a residue which was purified by MDAP (Formate) to give 1-((2S,4R)-2-methyl-4-((5-methylpyridin-2-yl)amino)-6-(4-(morpholine-4-carbonyl)phenyl)-3,4-dihydroquinolin-1(2H)-yl) ethanone formate as a pale yellow glass (24 mg, 0.045 mmol, 8% yield).

LCMS: (Formate, 2 min), Rt=0.66 min, MH+485.

Example 57

1-((2S,4R)-4-((5-chloropyridin-2-yl)amino)-2-methyl-6-(5-(morpholine-4-carbonyl) pyridin-2-yl)-3,4-dihydroquinolin-1(2H)-yl)ethanone

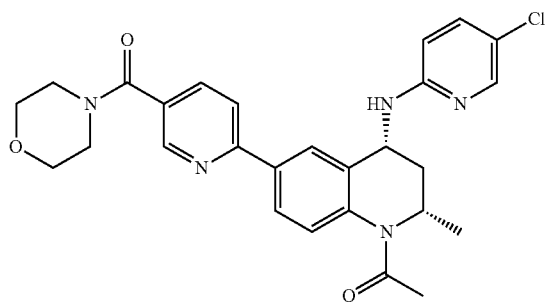

1-((2S,4R)-4-amino-2-methyl-6-(5-(morpholine-4-carbonyl)pyridin-2-yl)-3,4-dihydroquinolin-1(2H)-yl)ethanone hydrochloride (for a preparation see Intermediate 65) (100 mg, 0.232 mmol), 2-bromo-5-chloropyridine (89 mg, 0.464 mmol), 2'-(dicyclohexylphosphino)-N,N-dimethyl-[1,1'-biphenyl]-2-amine (18.3 mg, 0.046 mmol), tris(dibenzylideneacetone)dipalladium(0) (21.3 mg, 0.023 mmol) and sodium tert-butoxide (44.6 mg, 0.464 mmol) were combined in 1,4-dioxane (2 mL) and the mixture degassed over a period of 15 mins, before being heated under microwave irradiation to 120° C. for 25 mins. A further portion of 2-bromo-5-chloropyridine (89 mg, 0.464 mmol), 2'-(dicyclohexylphosphino)-N,N-dimethyl-[1,1'-biphenyl]-2-amine (18.3 mg, 0.046 mmol), tris(dibenzylideneacetone)dipalladium(0) (21.3 mg, 0.023 mmol), sodium tert-butoxide (44.6 mg, 0.464 mmol) and 1,4-dioxane (1 mL) were added and the mixture degassed over a period of 15 mins, before being heated under microwave irradiation to 120° C. for 25 mins. The reaction mixture was partitioned between saturated aqueous sodium bicarbonate (50 mL) and DCM (3×50 mL). The organics were combined, dried by passing through a hydrophobic frit and concentrated in vacuo to give a residue which was purified by MDAP (HpH) to give 1-((2S,4R)-4-((5-chloropyridin-2-yl)amino)-2-methyl-6-(5-(morpholine-4-carbonyl)pyridin-2-yl)-3,4-dihydroquinolin-1(2H)-yl)ethanone (34 mg, 0.067 mmol, 29% yield) LCMS: (Formate, 2 min), Rt=0.83 mins, MH+506.

Example 58

1-((2S,4R)-2-methyl-6-(5-(morpholine-4-carbonyl)pyridin-2-yl)-4-(pyrazin-2-ylamino)-3,4-dihydroquinolin-1(2H)-yl)ethanone

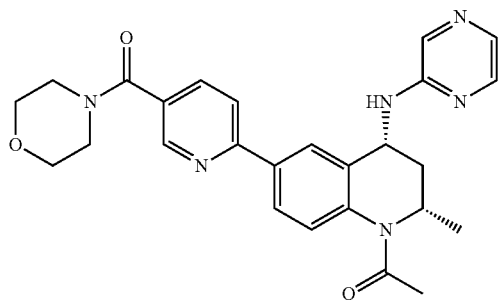 [SMILES: CC(=O)N1c2ccc(-c3ccc(C(=O)N4CCOCC4)cn3)cc2[C@H](Nc2cnccn2)C[C@@H]1C]

1-((2S,4R)-4-amino-2-methyl-6-(5-(morpholine-4-carbonyl)pyridin-2-yl)-3,4-dihydroquinolin-1(2H)-yl)ethanone hydrochloride (for a preparation see Intermediate 65) (100 mg, 0.232 mmol), 2-chloropyrazine (0.041 mL, 0.464 mmol), 2'-(dicyclohexylphosphino)-N,N-dimethyl-[1,1'-biphenyl]-2-amine (18.3 mg, 0.046 mmol), tris(dibenzylideneacetone)dipalladium(0) (21.3 mg, 0.023 mmol) and sodium tert-butoxide (44.6 mg, 0.464 mmol) were combined in 1,4-dioxane (2 mL) and the mixture degassed over a period of 15 mins, before being heated under microwave irradiation to 120° C. for 25 mins. A further portion of 2-chloropyrazine (0.041 mL, 0.464 mmol), 2'-(dicyclohexylphosphino)-N,N-dimethyl-[1,1'-biphenyl]-2-amine (18.3 mg, 0.046 mmol), tris(dibenzylideneacetone)dipalladium(0) (21.3 mg, 0.023 mmol), sodium tert-butoxide (44.6 mg, 0.464 mmol) and 1,4-dioxane (1 mL) were added and the mixture degassed over a period of 15 mins, before being heated under microwave irradiation to 120° C. for 25 mins. The reaction mixture was partitioned between saturated aqueous sodium bicarbonate (50 mL) and DCM (3×50 mL). The organics were combined, dried by passing through a hydrophobic frit and concentrated in vacuo to give a residue which was purified by MDAP (HpH) to give 1-((2S,4R)-2-methyl-6-(5-(morpholine-4-carbonyl)pyridin-2-yl)-4-(pyrazin-2-ylamino)-3,4-dihydroquinolin-1(2H)-yl)ethanone (40 mg, 0.085 mmol, 37% yield). LCMS: (Formate, 2 min), Rt=0.68 mins, MH+473

Example 59

1-((2S,4R)-2-methyl-4-((5-methylpyridin-2-yl)amino)-6-(5-(morpholine-4-carbonyl) pyridin-2-yl)-3,4-dihydroquinolin-1(2H)-yl)ethanone

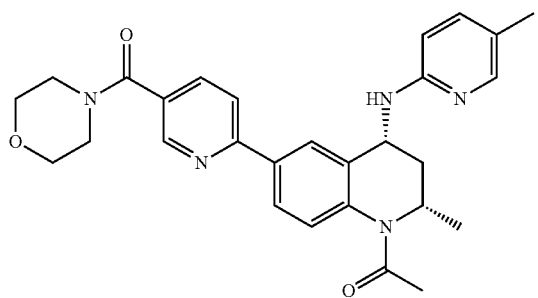 [SMILES: CC(=O)N1c2ccc(-c3ccc(C(=O)N4CCOCC4)cn3)cc2[C@H](Nc2ccc(C)cn2)C[C@@H]1C]

1-((2S,4R)-4-amino-2-methyl-6-(5-(morpholine-4-carbonyl)pyridin-2-yl)-3,4-dihydroquinolin-1(2H)-yl)ethanone hydrochloride (for a preparation see Intermediate 65) (80 mg, 0.186 mmol), 2-bromo-5-methylpyridine (63.9 mg, 0.371 mmol), 2'-(dicyclohexylphosphino)-N,N-dimethyl-[1,1'-biphenyl]-2-amine (14.6 mg, 0.037 mmol), tris(dibenzylideneacetone)dipalladium(0) (17 mg, 0.019 mmol) and sodium tert-butoxide (53.5 mg, 0.557 mmol) were combined in 1,4-dioxane (2 mL) and the mixture degassed over a period of 15 mins, before being heated under microwave irradiation to 130° C. for 50 mins. A further portion of 2-bromo-5-methylpyridine (63.9 mg, 0.371 mmol), 2'-(dicyclohexylphosphino)-N,N-dimethyl-[1,1'-biphenyl]-2-amine (14.6 mg, 0.037 mmol), tris(dibenzylideneacetone)dipalladium(0) (17 mg, 0.019 mmol), sodium tert-butoxide (53.5 mg, 0.557 mmol) and 1,4-dioxane (1 mL) were added and the mixture degassed over a period of 15 mins, before being heated under microwave irradiation to 130° C. for 25 mins. The reaction mixture was partitioned between saturated aqueous sodium bicarbonate (50 mL) and DCM (3×50 mL). The organics were combined, dried by passing through a hydrophobic frit and concentrated in vacuo to give a residue which was purified by MDAP (HpH) to give 1-((2S,4R)-2-methyl-4-((5-methylpyridin-2-yl)amino)-6-(5-(morpholine-4-carbonyl)pyridin-2-yl)-3,4-dihydroquinolin-1(2H)-yl)ethanone (38 mg, 0.078 mmol, 42% yield). LCMS: (Formate, 2 min), Rt=0.58 mins, MH+486.

Example 60

1-((2S,4R)-2-methyl-4-((5-methylpyrazin-2-yl)amino)-6-(5-(morpholine-4-carbonyl) pyridin-2-yl)-3,4-dihydroquinolin-1(2H)-yl)ethanone

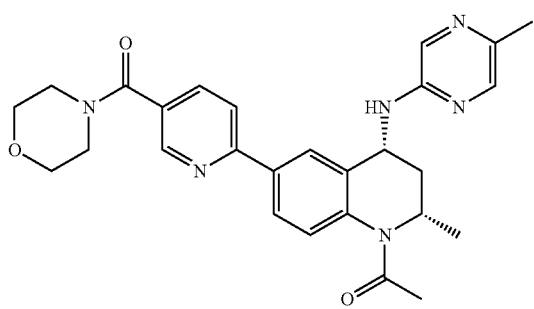 [SMILES: CC(=O)N1c2ccc(-c3ccc(C(=O)N4CCOCC4)cn3)cc2[C@H](Nc2cnc(C)cn2)C[C@@H]1C]

1-((2S,4R)-4-amino-2-methyl-6-(5-(morpholine-4-carbonyl)pyridin-2-yl)-3,4-dihydroquinolin-1(2H)-yl)ethanone hydrochloride (for a preparation see Intermediate 65) (100 mg, 0.232 mmol), 2-bromo-5-methylpyrazine (80 mg, 0.464 mmol), 2'-(dicyclohexylphosphino)-N,N-dimethyl-[1,1'-biphenyl]-2-amine (27.4 mg, 0.070 mmol), tris(dibenzylideneacetone)dipalladium(0) (42.5 mg, 0.046 mmol) and sodium tert-butoxide (66.9 mg, 0.696 mmol) were combined in 1,4-dioxane (2 mL) and the mixture degassed over a period of 15 mins, before being heated under microwave irradiation to 130° C. for 40 mins. The reaction mixture was partitioned between saturated aqueous sodium bicarbonate (50 mL) and DCM (3×50 mL). The organics were combined, dried by passing through a hydrophobic frit and concentrated in vacuo to give a residue which was purified by MDAP (HpH) to give 1-((2S,4R)-2-methyl-4-((5-methylpyrazin-2-yl)amino)-6-(5-(morpholine-4-carbonyl)pyridin-2-yl)-3,4-dihydroquinolin-1(2H)-yl)ethanone (38 mg, 0.078 mmol, 34% yield). LCMS: (Formate, 2 min), Rt=0.71 mins, MH+487

Example 61

1-((2S,4R)-2-methyl-6-(5-(morpholine-4-carbonyl)pyridin-2-yl)-4-(pyridin-2-ylamino)-3,4-dihydroquinolin-1(2H)-yl)ethanone

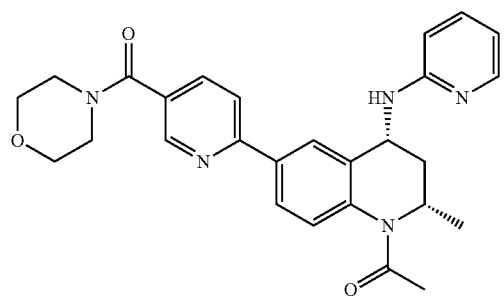 [SMILES: CC(=O)N1c2ccc(-c3ccc(C(=O)N4CCOCC4)cn3)cc2[C@H](Nc2ccccn2)C[C@@H]1C]

1-((2S,4R)-4-amino-2-methyl-6-(5-(morpholine-4-carbonyl)pyridin-2-yl)-3,4-dihydroquinolin-1(2H)-yl)ethanone hydrochloride (for a preparation see Intermediate 65) (100 mg, 0.232 mmol), 2-bromopyridine (0.044 mL, 0.464 mmol), 2'-(dicyclohexylphosphino)-N,N-dimethyl-[1,1'-biphenyl]-2-amine (18.3 mg, 0.046 mmol), tris(dibenzylideneacetone) dipalladium(0) (21.3 mg, 0.023 mmol) and sodium tert-butoxide (66.9 mg, 0.696 mmol) were combined in 1,4-dioxane (2 mL) and the mixture degassed over a period of 15 mins, before being heated under microwave irradiation to 130° C. for 25 mins. The reaction mixture was partitioned between saturated aqueous sodium bicarbonate (50 mL) and DCM (3×50 mL). The organics were combined, dried by passing through a hydrophobic frit and concentrated in vacuo to give a residue which was dissolved in acetonitrile (20 mL) and 0.1M aq. ammonium bicarbonate (20 mL). The mixture was filtered, and the filtrate concentrated in vacuo to give a residue which was purified by MDAP (HpH) to give 1-((2S,4R)-2-methyl-6-(5-(morpholine-4-carbonyl)pyridin-2-yl)-4-(pyridin-2-ylamino)-3,4-dihydroquinolin-1(2H)-yl)ethanone (41 mg, 0.087 mmol, 38% yield). LCMS: (Formate, 2 min), Rt=0.55 mins, MH+472

Example 62

1-((2S,4R)-4-(3-chlorophenyl)amino)-2-methyl-6-(6-(morpholine-4-carbonyl)pyridin-3-yl)-3,4-dihydroquinolin-1(2H)-yl)ethanone

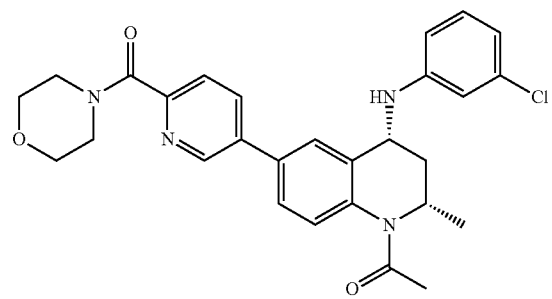 [SMILES: CC(=O)N1c2ccc(-c3ccc(C(=O)N4CCOCC4)nc3)cc2[C@H](Nc2cccc(Cl)c2)C[C@@H]1C]

1-((2S,4R)-4-amino-2-methyl-6-(6-(morpholine-4-carbonyl)pyridin-3-yl)-3,4-dihydroquinolin-1(2H)-yl)ethanone (for a preparation, see Intermediate 56) (100 mg, 0.254 mmol), 1-bromo-3-chlorobenzene (0.060 mL, 0.507 mmol), 2'-(dicyclohexylphosphino)-N,N-dimethyl-[1,1'-biphenyl]-2-amine (20.0 mg, 0.051 mmol), tris(dibenzylideneacetone)dipalladium(0) (23.3 mg, 0.025 mmol) and sodium tert-butoxide (34.1 mg, 0.355 mmol) were combined in 1,4-dioxane (2.5 mL). The mixture was degassed over a period of 15 mins before being heated under microwave irradiation to 120° C. for 25 mins. The mixture was partitioned between water (50 mL) and DCM (3×50 mL). The organic layers were combined, dried by passing through a hydrophobic frit and concentrated in vacuo. The resulting residue was purified by MDAP (HpH) to give 1-((2S,4R)-4-((3-chlorophenyl)amino)-2-methyl-6-(6-(morpholine-4-carbonyl)pyridin-3-yl)-3,4-dihydroquinolin-1(2H)-yl)ethanone (58 mg, 0.115 mmol, 45% yield).

LCMS: (Formate, 2 min), Rt=1.00 mins, MH+=505

Example 63

1-((2S,4R)-4-(3-chlorophenyl)amino)-2-methyl-6-(5-(morpholine-4-carbonyl)pyridin-2-yl)-3,4-dihydroquinolin-1(2H)-yl)ethanone

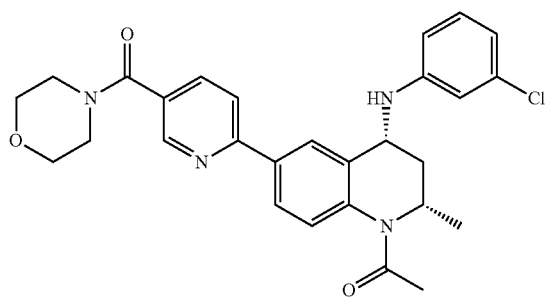 [SMILES: CC(=O)N1c2ccc(-c3ccc(C(=O)N4CCOCC4)cn3)cc2[C@H](Nc2cccc(Cl)c2)C[C@@H]1C]

1-((2S,4R)-4-amino-2-methyl-6-(5-(morpholine-4-carbonyl)pyridin-2-yl)-3,4-dihydroquinolin-1(2H)-yl)ethanone hydrochloride (for a preparation see Intermediate 65) (120 mg, 0.278 mmol), 1-bromo-3-chlorobenzene (0.065 mL, 0.557 mmol), 2'-(dicyclohexylphosphino)-N,N-dimethyl-[1,1'-biphenyl]-2-amine (21.9 mg, 0.056 mmol), tris(dibenzylideneacetone)dipalladium(0) (25.5 mg, 0.028 mmol) and sodium tert-butoxide (37.5 mg, 0.390 mmol) were combined in 1,4-dioxane (2 mL) and the mixture degassed over a period of 15 mins, before being heated under microwave irradiation to 120° C. for 25 mins. The reaction mixture was partitioned between water (50 mL) and DCM (3×50 mL). The organics were combined, dried by passing through a hydrophobic frit and concentrated in vacuo to give a residue which was purified by MDAP (HpH) to give 1-((2S,4R)-4-((3-chlorophenyl)amino)-2-methyl-6-(5-(morpholine-4-carbonyl)pyridin-2-yl)-3,4-dihydroquinolin-1(2H)-yl)ethanone (13 mg, 0.026 mmol, 9.2% yield).

LCMS: (Formate, 2 min), Rt=1.00 mins, MH+505.

Example 64

1-((2S,4R)-4-((4-chlorophenyl)amino)-2-methyl-6-(5-(morpholine-4-carbonyl)pyridin-2-yl)-3,4-dihydroquinolin-1(2H)-yl)ethanone

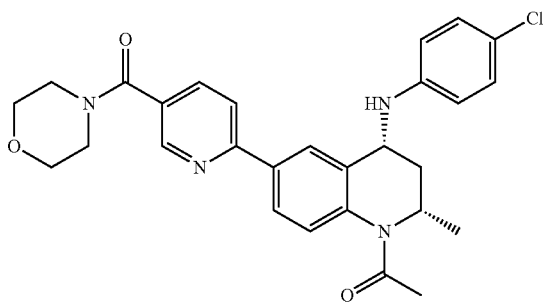 [SMILES: CC(=O)N1c2ccc(-c3ccc(C(=O)N4CCOCC4)cn3)cc2[C@H](Nc2ccc(Cl)cc2)C[C@@H]1C]

1-((2S,4R)-4-amino-2-methyl-6-(5-(morpholine-4-carbonyl)pyridin-2-yl)-3,4-dihydroquinolin-1(2H)-yl)ethanone hydrochloride (for a preparation see Intermediate 65) (120 mg, 0.278 mmol), 1-bromo-4-chlorobenzene (107 mg, 0.557 mmol), 2'-(dicyclohexylphosphino)-N,N-dimethyl-[1,1'-biphenyl]-2-amine (21.9 mg, 0.056 mmol), tris(dibenzylideneacetone)dipalladium(0) (25.5 mg, 0.028 mmol) and sodium tert-butoxide (37.5 mg, 0.390 mmol) were combined in 1,4-dioxane (2 mL) and the mixture degassed over a period of 15 mins, before being heated under microwave irradiation to 120° C. for 25 mins. The reaction mixture was partitioned between water (50 mL) and DCM (3×50 mL). The organics were combined, dried by passing through a hydrophobic frit and concentrated in vacuo to give a residue which was purified by MDAP (HpH) to give 1-((2S,4R)-4-((4-chlorophenyl)amino)-2-methyl-6-(5-(morpholine-4-carbonyl)pyridin-2-yl)-3,4-dihydroquinolin-1(2H)-yl)ethanone (15 mg, 0.030 mmol, 10.7% yield).

LCMS: (Formate, 2 min), Rt=1.00 mins, MH+=505.

Example 65

6-(((2S,4R)-1-acetyl-2-methyl-6-(4-(morpholine-4-carbonyl)phenyl)-1,2,3,4-tetrahydroquinolin-4-yl)amino)nicotinonitrile

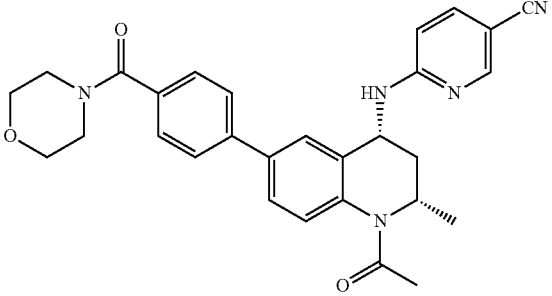 [SMILES: CC(=O)N1c2ccc(-c3ccc(C(=O)N4CCOCC4)cc3)cc2[C@H](Nc2ccc(C#N)cn2)C[C@@H]1C]

Crude lithium 4-((2S,4R)-1-acetyl-4-((5-cyanopyridin-2-yl)amino)-2-methyl-1,2,3,4-tetrahydroquinolin-6-yl)benzoic acid. (Intermediate 67) (55 mg) and HATU (53 mg, 0.140 mmol) in anhydrous DMF (1 mL) was treated with DIPEA (67.5 µL, 0.388 mmol). The mixture was sonicated briefly to give a solution, to which was added morpholine (110 µL, 1.26 mmol). The solution was left at room temperature overnight and then diluted with water to ~10 mL. The mixture was further diluted with brine and extracted with DCM/EtOAc and then EtOAc. The combined organic fractions were dried by passing through a hydrophobic frit and concentrated to dryness under a stream of nitrogen. The resulting residue was purified by MDAP (Formate) to give 6-(((2S,4R)-1-acetyl-2-methyl-6-(4-(morpholine-4-carbonyl)phenyl)-1,2,3,4-tetrahydroquinolin-4-yl)amino)nicotinonitrile (26 mg, 0.052 mmol) as a colourless glass. LCMS; (Formate, 2 min) Rt=0.85 min, MH+496.

Example 66

1-((2S,4R)-4-(5-fluoropyridin-2-yl)amino)-2-methyl-6-(6-(morpholine-4-carbonyl) pyridin-3-yl)-3,4-dihydroquinolin-1(2H)-yl)ethanone

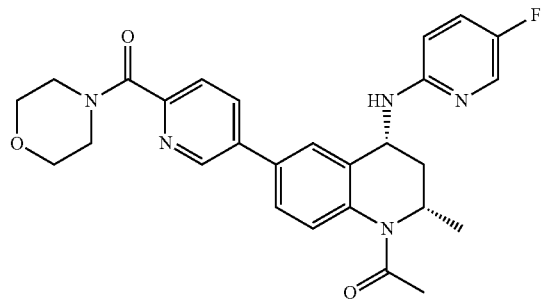 [SMILES: CC(=O)N1c2ccc(-c3ccc(C(=O)N4CCOCC4)nc3)cc2[C@H](Nc2ccc(F)cn2)C[C@@H]1C]

1-((2S,4R)-4-amino-2-methyl-6-(6-(morpholine-4-carbonyl)pyridin-3-yl)-3,4-dihydroquinolin-1(2H)-yl)ethanone (for a preparation, see Intermediate 56) (145 mg, 0.368 mmol), 2-bromo-5-fluoropyridine (129 mg, 0.735 mmol), 2'-(dicyclohexylphosphino)-N,N-dimethyl-[1,1'-biphenyl]-2-amine (29 mg, 0.074 mmol), tris(dibenzylideneacetone)dipalladium(0) (34 mg, 0.037 mmol) and sodium tert-butoxide (71 mg, 0.739 mmol) were combined in 1,4-dioxane (4 mL). The mixture was degassed over a period of 15 mins before being heated under microwave irradiation to 120° C. for 30 mins. A further portion of 2-bromo-5-fluoropyridine (129 mg, 0.735 mmol), 2'-(dicyclohexylphosphino)-N,N-dimethyl-[1,1'-biphenyl]-2-amine (29 mg, 0.074 mmol), tris(dibenzylideneacetone)dipalladium(0) (34 mg, 0.037 mmol) were added, The mixture was degassed over a period of 15 mins before being heated under microwave irradiation to 120° C. for 30 mins. The mixture was partitioned between water (20 mL) and DCM (3×15 mL). The organic layers were combined, dried by passing through a hydrophobic frit and concentrated in vacuo. The resulting residue was purified by chromatography (25 g column, (MeOH/DCM gradient) to give 1-((2S,4R)-4-((5-fluoropyridin-2-yl)amino)-2-methyl-6-(6-(morpholine-4-carbonyl)pyridin-3-yl)-3,4-dihydro-quinolin-1(2H)-yl)ethanone (91 mg, 0.186 mmol, 51% yield). LCMS: (Formate, 2 min), Rt=0.73 mins, MH+490.

Example 67

1-((2S,4R)-2-methyl-4-(pyridin-2-ylamino)-6-(4-(pyrrolidine-1-carbonyl)phenyl)-3,4-dihydroquinolin-1(2H)-yl)ethanone formate

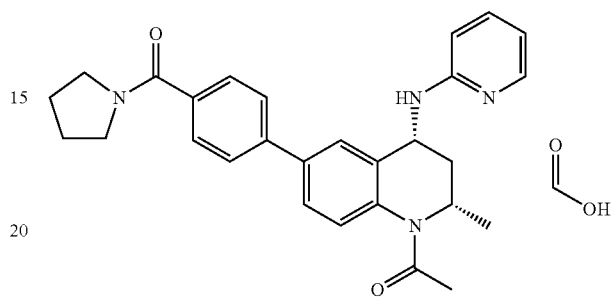

Crude lithium 4-((2S,4R)-1-acetyl-2-methyl-4-(pyridin-2-ylamino)-1,2,3,4-tetrahydroquinolin-6-yl)benzoate for a preparation see Intermediate 58) (40 mg) and HATU (41 mg, 0.108 mmol) in DMF (0.5 mL) were treated with DIPEA (51.2 µL, 0.294 mmol) and the mixture shaken and sonicated until a solution was formed (<2 min). This solution was added to pyrrolidine (16 µL, 0.192 mmol), the mixture briefly shaken then left to stand at room temperature for 2 h. A further portion of morpholine (32 µL, 0.384 mmol) was added and the mixture left to stand overnight. The mixture was diluted with water and extracted three times with DCM. The combined organic layers were dried by passing through a hydrophobic frit and concentrated in vacuo to give a residue. The residue was purified by MDAP (formate) to give 1-((2S,4R)-2-methyl-4-(pyridin-2-ylamino)-6-(4-(pyrrolidine-1-carbonyl)phenyl)-3,4-dihydroquinolin-1(2H)-yl)ethanone formate (23 mg, 0.046 mmol, 12%) as a pale pink glass. LCMS: (Formate, 2 min), Rt=0.70 min, MH+455

Example 68

1-((2S,4R)-2-methyl-4-((5-methylpyridin-2-yl)amino)-6-(4-(pyrrolidine-1-carbonyl)phenyl)-3,4-dihydroquinolin-1(2H)-yl)ethanone formate

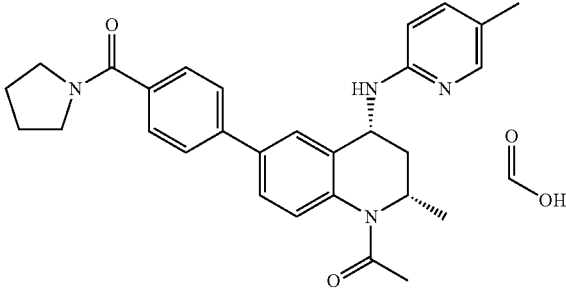 [SMILES: CC(=O)N1c2ccc(-c3ccc(C(=O)N4CCCC4)cc3)cc2[C@H](Nc2ccc(C)cn2)C[C@@H]1C ; O=CO]

A mixture of crude lithium 4-((2S,4R)-1-acetyl-2-methyl-4-((5-methylpyridin-2-yl)amino)-1,2,3,4-tetrahydroquinolin-6-yl)benzoate (for a preparation see Intermediate 60) (48 mg) and HATU (48 mg, 0.316 mmol) in DMF (0.5 mL) was treated with DIPEA (0.06 mL, 0.344 mmol) and the mixture stirred at room temperature for 5 min to give a solution which was added to pyrollidine (48 μL, 0.575 mmol). The mixture was shaken briefly and then left at room temperature overnight. The resulting solution was diluted with water to and left to stand for ~10 min. The resultant precipitate was isolated by filtration and washed with water. The isolated precipitate was dissolved in MeOH concentrated to dryness to give a residue which was purified by MDAP (Formate) to give 1-((2S,4R)-2-methyl-4-((5-methylpyridin-2-yl)amino)-6-(4-(pyrrolidine-1-carbonyl)phenyl)-3,4-dihydroquinolin-1(2H)-yl)ethanone formate (22 mg, 0.047 mmol, 7.5%) as a pale yellow glass.

LCMS: (Formate, 2 min), Rt=0.73 min, MH+469.

REFERENCE COMPOUNDS

Experimental details of LC-MS methods A-F as referred to herein are as follows:

LC/MS (Method A) was conducted on an Acquity UPLC BEH C18 column (50 mm×2.1 mm i.d. 1.7 μm packing diameter) at 40 degrees centigrade, eluting with 10 mM Ammonium Bicarbonate in water adjusted to pH 10 with Ammonia solution (Solvent A) and Acetonitrile (Solvent B) using the following elution gradient 0-1.5 min 1-97% B, 1.5-1.9 min 97% B, 1.9-2.0 min 100% B at a flow rate of 1 ml/min. The UV detection was a summed signal from wavelength of 210 nm to 350 nm. The mass spectra were recorded on a Waters ZQ Mass Spectrometer using Alternate-scan Positive and Negative Electrospray. Ionisation data was rounded to the nearest integer.

LC/MS (Method B) was conducted on an Acquity UPLC BEH C18 column (50 mm×2.1 mm i.d. 1.7 μm packing diameter) at 40 degrees centigrade, eluting with 0.1% v/v solution of Formic Acid in Water (Solvent A) and 0.1% v/v solution of Formic Acid in Acetonitrile (Solvent B) using the following elution gradient 0-1.5 min 3-100% B, 1.5-1.9 min 100% B, 1.9-2.0 min 3% B at a flow rate of 1 ml/min. The UV detection was a summed signal from wavelength of 210 nm to 350 nm. The mass spectra were recorded on a Waters ZQ Mass Spectrometer using Alternate-scan Positive and Negative Electrospray. Ionisation data was rounded to the nearest integer.

LC/MS (Method C) was conducted on an Acquity UPLC BEH C18 column (50 mm×2.1 mm i.d. 1.7 μm packing diameter) at 40 degrees centigrade, eluting with 0.1% v/v solution of Trifluoroacetic Acid in Water (Solvent A) and 0.1% v/v solution of Trifluoroacetic Acid in Acetonitrile (Solvent B) using the following elution gradient 0-1.5 min 3-100% B, 1.5-1.9 min 100% B, 1.9-2.0 min 3% B at a flow rate of 1 ml/min. The UV detection was a summed signal from wavelength of 210 nm to 350 nm. The mass spectra were recorded on a Waters ZQ Mass Spectrometer using Positive Electrospray. Ionisation data was rounded to the nearest integer.

LC/MS (Method D) was conducted on a Supelcosil LCABZ+PLUS column (3 μm, 3.3 cm×4.6 mm ID) eluting with 0.1% HCO$_2$H and 0.01 M ammonium acetate in water (solvent A), and 95% acetonitrile and 0.05% HCO$_2$H in water (solvent B), using the following elution gradient 0-0.7 minutes 0% B, 0.7-4.2 minutes 0→100% B, 4.2-5.3 minutes 100% B, 5.3-5.5 minutes 100→0% B at a flow rate of 3 mL/minute. The mass spectra (MS) were recorded on a Fisons VG Platform mass spectrometer using electrospray positive ionisation [(ES+ve to give [M+H]$^+$ and [M+NH$_4$]$^+$ molecular ions] or electrospray negative ionisation [(ES-ve to give [M-H]- molecular ion] modes. Analytical data from this apparatus are given with the following format: [M+H]$^+$ or [M-H]$^-$.

LC/MS (Method E) was conducted on a Chromolith Performance RP 18 column (100×4.6 mm id) eluting with 0.01M ammonium acetate in water (solvent A) and 100% acetonitrile (solvent B), using the following elution gradient 0-4 minutes 0-100% B, 4-5 minutes 100% B at a flow rate of 5 ml/minute. The mass spectra (MS) were recorded on a micromass Platform-LC mass spectrometer using atmospheric pressure chemical positive ionisation [AP+ve to give MH+ molecular ions] or atmospheric pressure chemical negative ionisation [AP-ve to give (M-H)- molecular ions] modes. Analytical data from this apparatus are given with the following format: [M+H]+ or [M-H]-.

LC/MS (Method F) was conducted on an Sunfire C18 column (30 mm×4.6 mm i.d. 3.5 μm packing diameter) at 30 degrees centigrade, eluting with 0.1% v/v solution of Trifluoroacetic Acid in Water (Solvent A) and 0.1% v/v solution of Trifluoroacetic Acid in Acetonitrile (Solvent B) using the following elution gradient 0-0.1 min 3% B, 0.1-4.2 min 3-100% B, 4.2-4.8 min 100% B, 4.8-4.9 min 100-3% B, 4.9-5.0 min 3% B at a flow rate of 3 ml/min. The UV detection was an averaged signal from wavelength of 210 nm to 350 nm and mass spectra were recorded on a mass spectrometer using positive electrospray ionization. Ionisation data was rounded to the nearest integer.

LC/MS (Method G) was conducted on an Acquity UPLC BEH C18 column (50 mm×2.1 mm i.d. 1.7 μm packing diameter) at 40 degrees centigrade, eluting with 0.1% v/v solution of Formic Acid in Water (Solvent A) and 0.1% v/v solution of Formic Acid in Acetonitrile (Solvent B) using the following elution gradient 0-1.5 min 1-97% B, 1.5-1.9 min 97% B, 1.9-2.0 min 97 to 100% B at a flow rate of 1 ml/min. The UV detection was a summed signal from wavelength of 210 nm to 350 nm. The mass spectra were recorded on a Waters ZQ Mass Spectrometer using Alternate-scan Positive and Negative Electrospray. Ionisation data was rounded to the nearest integer.

LC/HRMS: Analytical HPLC was conducted on a Uptisphere-hsc column (3 μm 33×3 mm id) eluting with 0.01M ammonium acetate in water (solvent A) and 100% acetonitrile (solvent B), using the following elution gradient 0-0.5 minutes 5% B, 0.5-3.75 minutes 5→100% B, 3.75-4.5 100% B, 4.5-5 100→5% B, 5-5.5 5% B at a flow rate of 1.3 mL/minute. The mass spectra (MS) were recorded on a micromass LCT mass spectrometer using electrospray positive ionisation [ES+ve to give MH$^+$ molecular ions] or electrospray negative ionisation [ES-ve to give (M-H)- molecular ions] modes.

TLC (thin layer chromatography) refers to the use of TLC plates sold by Merck coated with silica gel 60 F254.

Reference Compound A 2-methyl-6-(methyloxy)-4H-3,1-benzoxazin-4-one

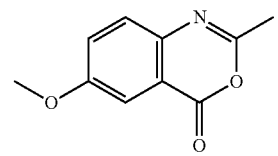

A solution of 5-methoxyanthranilic acid (Lancaster) (41.8 g, 0.25 mol) was refluxed in acetic anhydride (230 mL) for 3.5 h before being concentrated under reduced pressure. The crude compound was then concentrated twice in the presence of toluene before being filtered and washed twice with ether to yield to the title compound (33.7 g, 71% yield) as a brown solid. LC/MS (Method D): m/z 192 [M+H]+, Rt 1.69 min.

Reference Compound B

[2-amino-5-(methyloxy)phenyl](4-chlorophenyl) methanone

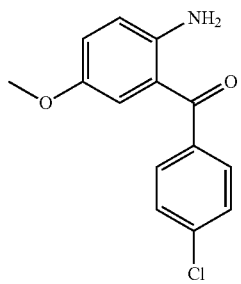 [SMILES: COc1ccc(N)c(C(=O)c2ccc(Cl)cc2)c1]

To a solution of 2-methyl-6-(methyloxy)-4H-3,1-benzoxazin-4-one (for a preparation see Reference compound A) (40.0 g, 0.21 mol) in a toluene/ether (2/1) mixture (760 mL) at 0° C. was added dropwise a solution of 4-chlorophenylmagnesium bromide (170 mL, 1M in Et$_2$O, 0.17 mol). The reaction mixture was allowed to warm to room temperature and stirred for 1 h before being quenched with 1N HCl (200 mL). The aqueous layer was extracted with EtOAc (3×150 mL) and the combined organics were washed with brine (100 mL), dried over Na$_2$SO$_4$, filtered and concentrated under reduced pressure. The crude compound was then dissolved in EtOH (400 mL) and 6N HCl (160 mL) was added. The reaction mixture was refluxed for 2 h before being concentrated to one-third in volume. The resulting solid was filtered and washed twice with ether before being suspended in EtOAc and neutralised with 1N NaOH. The aqueous layer was extracted with EtOAc (3×150 mL) and the combined organics were washed with brine (150 mL), dried over Na$_2$SO$_4$, filtered and concentrated under reduced pressure. The title compound was obtained as a yellow solid (39 g, 88% yield);
LC/MS (Method D): m/z 262 [M+H]+, Rt 2.57 min.

Reference Compound C

Methyl N$^1$-[2-[(4-chlorophenyl)carbonyl]-4-(methyloxy)phenyl]-N$^2$-{[(9H-fluoren-9-ylmethyl)oxy]carbonyl}-L-α-asparaginate

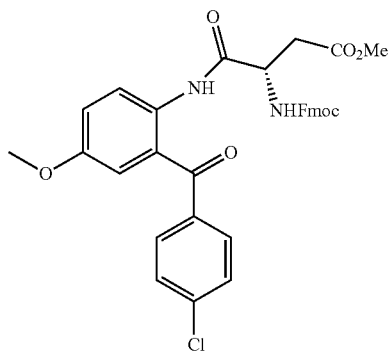

Methyl N-{[(9H-fluoren-9-ylmethyl)oxy]carbonyl}-L-α-aspartyl chloride (*Int. J. Peptide Protein Res.* 1992, 40, 13-18) (93 g, 0.24 mol) was dissolved in CHCl$_3$ (270 mL) and [2-amino-5-(methyloxy)phenyl](4-chlorophenyl)methanone (for a preparation see Reference compound B) (53 g, 0.2 mol) was added. The resulting mixture was stirred at 60° C. for 1 h before being cooled and concentrated to 60% in volume. Ether was added at 0° C. and the resulting precipitate was filtered and discarded. The filtrate was concentrated under reduced pressure and used without further purification.

Reference Compound D

Methyl [(3S)-5-(4-chlorophenyl)-7-(methyloxy)-2-oxo-2,3-dihydro-1H-1,4-benzodiazepin-3-yl]acetate

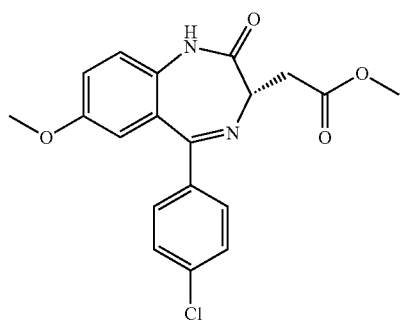

To a solution of methyl N1-[2-[(4-chlorophenyl)carbonyl]-4-(methyloxy)phenyl]-N2-{[(9H-fluoren-9-ylmethyl)oxy]carbonyl}-L-α-asparaginate (for a preparation see Reference compound C) (assumed 0.2 mol) in DCM (500 mL) was added Et$_3$N (500 mL, 3.65 mol) and the resulting mixture was refluxed for 24 h before being concentrated. The resulting crude amine was dissolved in 1,2-DCE (1.5 L) and AcOH (104 mL, 1.8 mol) was added carefully. The reaction mixture was then stirred at 60° C. for 2 h before being concentrated in vacuo and dissolved in DCM. The organic layer was washed with 1N HCl and the aqueous layer was extracted with DCM (×3). The combined organic layers were washed twice with water, and brine, dried over Na$_2$SO$_4$, filtered and concentrated under reduced pressure. The crude solid was recrystallised in MeCN leading to the title compound (51 g) as a pale yellow solid. The filtrate could be concentrated and recrystallised in MeCN to give to another 10 g of the desired product R$_f$=0.34 (DCM/MeOH: 95/5).

HRMS (M+H)⁺ calculated for $C_{19}H_{18}{}^{35}ClN_2O_4$ 373.0955. found 373.0957.

Reference Compound E

Methyl [(3S)-5-(4-chlorophenyl)-7-(methyloxy)-2-thioxo-2,3-dihydro-1H-1,4-benzodiazepin-3-yl]acetate

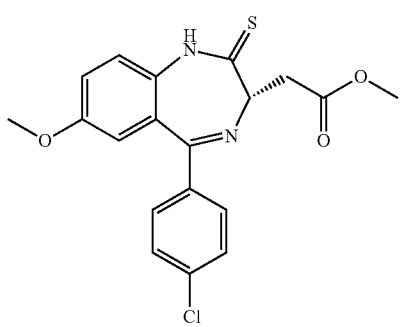

A suspension of $P_4S_{10}$ (36.1 g, 81.1 mmol) and $Na_2CO_3$ (8.6 g, 81.1 mmol) in 1,2-DCE (700 mL) at room temperature was stirred for 2 h before Methyl [(3S)-5-(4-chlorophenyl)-7-(methyloxy)-2-oxo-2,3-dihydro-1H-1,4-benzodiazepin-3-yl]acetate (for a preparation see Reference compound D) (16.8 g, 45.1 mmol) was added. The resulting mixture was stirred at 70° C. for 2 h before being cooled and filtered. The solid was washed twice with DCM and the filtrate washed with sat. $NaHCO_3$ and brine. The organic layer was dried over $Na_2SO_4$, filtered and concentrated under reduced pressure. The crude product was purified by flash-chromatography on silica gel (DOM/MeOH: 99/1) to afford the title compound (17.2 g, 98% yield) as a yellowish solid. LC/MS (Method D): m/z 389 [M($^{35}$Cl)+H]⁺, Rt 2.64 min HRMS (M+H)⁺ calculated for $C_{19}H_{18}{}^{35}ClN_2O_3S$ 389.0727. found 389.0714.

Reference Compound F

Methyl [(3S)-2-[(1Z)-2-acetylhydrazino]-5-(4-chlorophenyl)-7-(methyloxy)-3H-1,4-benzodiazepin-3-yl]acetate

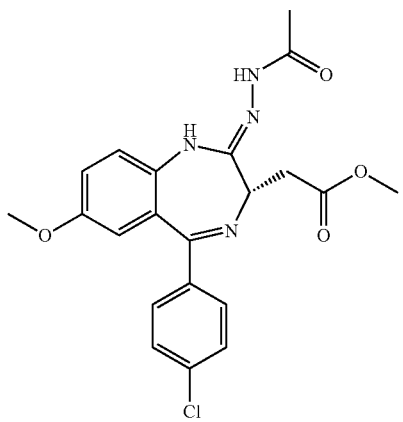

To a suspension of methyl [(3S)-5-(4-chlorophenyl)-7-(methyloxy)-2-thioxo-2,3-dihydro-1H-1,4-benzodiazepin-3-yl]acetate (for a preparation see Reference compound E) (9.0 g, 23.2 mmol) in THF (300 mL) at 0° C. was added hydrazine monohydrate (3.4 mL, 69.6 mmol) dropwise. The reaction mixture was stirred for 5 h between 5° C. and 15° C. before being cooled at 0° C. $Et_3N$ (9.7 mL, 69.6 mmol) was then added slowly and acetyl chloride (7.95 mL, 69.6 mmol) was added dropwise. The mixture was then allowed to warm to room temperature for 16 h before being concentrated under reduced pressure. The crude product was dissolved in DCM and washed with water. The organic layer was dried over $Na_2SO_4$, filtered and concentrated in vacuo to give the crude title compound (9.7 g, 98% yield) which was used without further purification. $R_f$=0.49 (DCM/MeOH:90/10).

Reference Compound G

Methyl [(4S)-6-(4-chlorophenyl)-1-methyl-8-(methyloxy)-4H-[1,2,4]triazolo[4,3-a][1,4]benzodiazepin-4-yl]acetate

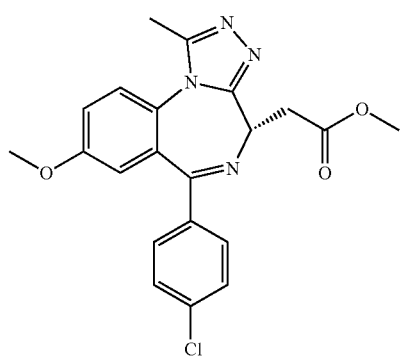

The crude methyl [(3S)-2-[(1Z)-2-acetylhydrazino]-5-(4-chlorophenyl)-7-(methyloxy)-3H-1,4-benzodiazepin-3-yl]acetate (for a preparation see Reference compound F) (assumed 9.7 g) was suspended in THF (100 ml) and AcOH (60 mL) was added at room temperature. The reaction mixture was stirred at this temperature for 2 days before being concentrated under reduced pressure. The crude solid was triturated in i-$Pr_2O$ and filtered to give the title compound (8.7 g, 91% over 3 steps) as an off-white solid.

HRMS (M+H)⁺ calculated for $C_{21}H_{20}ClN_4O_3$ 411.1229. found 411.1245.

Reference Compound H

[(4S)-6-(4-Chlorophenyl)-1-methyl-8-(methyloxy)-4H-[1,2,4]triazolo[4,3-a][1,4]benzodiazepin-4-yl]acetic acid

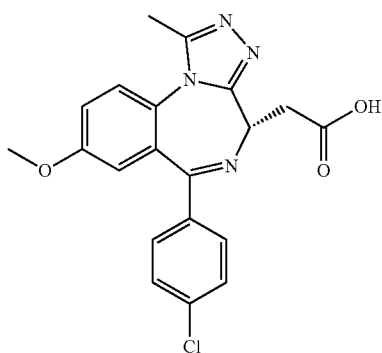 [SMILES: COc1ccc2c(c1)C(c1ccc(Cl)cc1)=N[C@@H](CC(=O)O)c1nnc(C)n1-2]

To a solution of methyl [(4S)-6-(4-chlorophenyl)-1-methyl-8-(methyloxy)-4H-[1,2,4]triazolo[4,3-a][1,4]benzodiazepin-4-yl]acetate (for a preparation see Reference compound G)(7.4 g, 18.1 mmol) in THF (130 mL) at room temperature was added 1N NaOH (36.2 mL, 36.2 mmol). The reaction mixture was stirred at this temperature for 5 h before being quenched with 1N HCl (36.2 mL) and concentrated in vacuo. Water is then added and the aqueous layer was extracted with DCM (×3) and the combined organic layers were dried over Na₂SO₄, filtered and concentrated under reduced pressure to give the title compound (7 g, 98% yield) as a pale yellow solid.

LC/MS (Method D): m/z 397 [M+H]⁺

Reference Compound I 1,1-dimethylethyl [5-({[(4S)-6-(4-chlorophenyl)-1-methyl-8-(methyloxy)-4H-[1,2,4]triazolo[4,3-a][1,4]benzodiazepin-4-yl]acetyl}amino)pentyl]carbamate

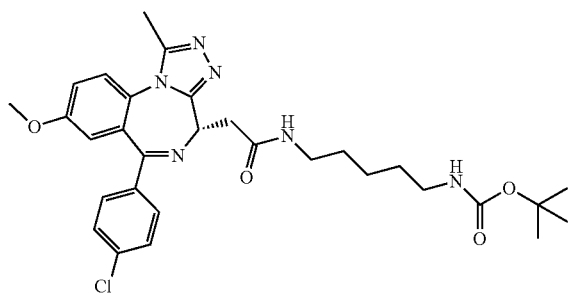 [SMILES: COc1ccc2c(c1)C(c1ccc(Cl)cc1)=N[C@@H](CC(=O)NCCCCCNC(=O)OC(C)(C)C)c1nnc(C)n1-2]

A mixture of [(4S)-6-(4-chlorophenyl)-1-methyl-8-(methyloxy)-4H-[1,2,4]triazolo[4,3-a][1,4]benzodiazepin-4-yl]acetic acid (for a preparation see Reference compound H) (1.0 g, 2.5 mmol), HATU (1.9 g, 5 mmol) and DIPEA (0.88 ml, 5 mmol) was stirred for 80 minutes at room temperature, to this was added 1,1-dimethylethyl (4-aminobutyl)carbamate (1.05 ml, 5.0 mmol, available from Aldrich). The reaction mixture was stirred at room temperature for 2 h before it was concentrated. The residue was taken up in dichloromethane and washed with 1N HCl. The aqueous layer was extracted with dichloromethane twice. Organic layer was washed with 1N sodium hydroxide, followed by a saturated solution of sodium chloride, dried over sodium sulphate and concentrated. The residue was purified by flash-chromatography on silica using dichloromethane/methanol 95/5 to give the title compound as a yellow solid (1.2 g). LC/MS (Method D): rt=3.04 min.

Reference Compound J

N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide trifluoroacetate

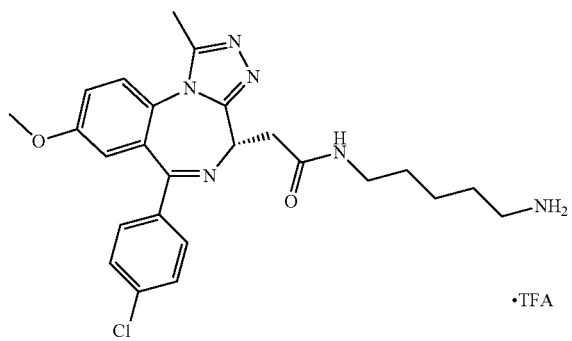 [SMILES: COc1ccc2c(c1)C(c1ccc(Cl)cc1)=N[C@@H](CC(=O)NCCCCCN)c1nnc(C)n1-2]

To a solution of 1,1-dimethylethyl [5-({[(4S)-6-(4-chlorophenyl)-1-methyl-8-(methyloxy)-4H-[1,2,4]triazolo[4,3-a][1,4]benzodiazepin-4-yl]acetyl}amino)pentyl]carbamate (for a preparation see Reference compound I) (0.2 g, 0.34 mmol) in dichloromethane (3 ml) was added trifluoroacetic acid (0.053 ml, 0.68 mmol) dropwise at 0° C. The reaction mixture was stirred for 3 h from 0° C. to room temperature. The reaction mixture was concentrated to dryness to afford the title compound as a hygroscopic yellow oil (200 mg)

LC/MS (Method D): rt=2.33 min.

HRMS (M+H)⁺ calculated for $C_{25}H_{29}ClN_6O_2$ 481.2119. found 481.2162.

Reference Compound K

Mixture of 5- and 6-isomers of Alexa Fluor 488-N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide

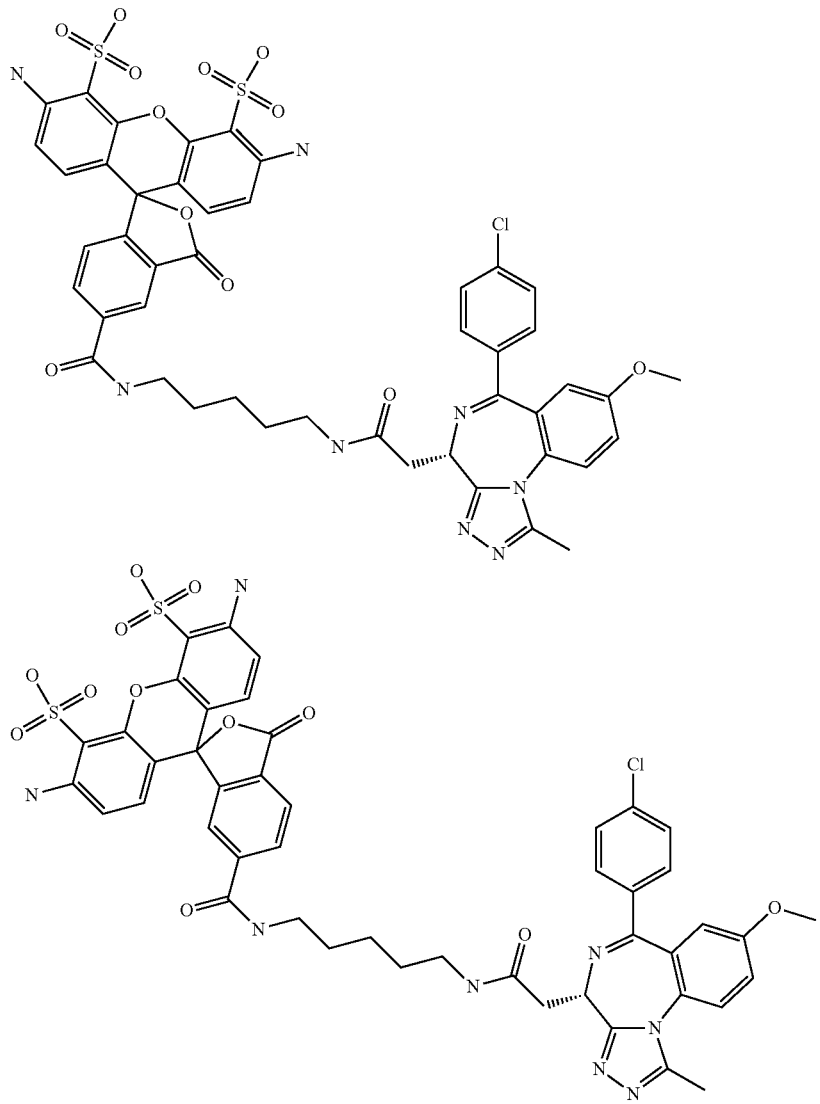

N-(5-Aminopentyl)-2-[(4S)-6-(4-chlorophenyl)-1-methyl-8-(methyloxy)-4H-[1,2,4]triazolo[4,3-a][1,4]benzodiazepin-4-yl]acetamide trifluoroacetate (for a preparation see Reference compound J) (7.65 mg, 0.013 mmol) was dissolved in N,N-Dimethylformamide (DMF) (300 µl) and added to Alexa Fluor 488 carboxylic acid succinimidyl ester (5 mg, 7.77 µmol, mixture of 5 and 6 isomers, available from Invitrogen, product number A-20100) in an Eppendorf centrifuge tube. Hunig's base (7.0 µl, 0.040 mmol) was added and the mixture vortex mixed overnight. After 18 h the reaction mixture was evaporated to dryness and the residue redissolved in DMSO/water (50%, <1 ml total), applied to a preparative Phenomenex Jupiter C18 column and eluted with a gradient of 95% A: 5% B to 100% B (A=0.1% trifluoroacetic acid in water, B=0.1% TFA/90% acetonitrile/10% water) at a flow rate of 10 ml/min over 150 minutes. Impure fractions were combined and re-purified using the same system. Fractions were combined and evaporated to yield the title product (2.8 mg) as a mixture of the 2 regioisomers shown. LC/MS (Method F):, MH+=999, rt=1.88 min.

Biological Test Methods

Fluorescence Anisotropy Binding Assay

The binding of the compounds of formula (I) to Bromodomains BRD2, BRD3 and BRD4 may be assessed using a Fluorescence Anisotropy Binding Assay.

The Bromodomain protein, fluorescent ligand (Reference compound K see above) and a variable concentration of test compound are incubated together to reach thermodynamic equilibrium under conditions such that in the absence of test compound the fluorescent ligand is significantly (>50%) bound and in the presence of a sufficient concentration of a potent inhibitor the anisotropy of the unbound fluorescent ligand is measurably different from the bound value.

All data was normalized to the mean of 16 high and 16 low control wells on each plate. A four parameter curve fit of the following form was then applied:

$$y=a+((b-a)/(1+(10^{\wedge}x/10^{\wedge}c)^{\wedge}d)$$

Where 'a' is the minimum, 'b' is the Hill slope, 'c' is the pIC50 and 'd' is the maximum.

Recombinant Human Bromodomains (BRD2 (1-473), BRD3 (1-435) and BRD4 (1-477)) were expressed in *E. coli* cells (in pET15b vector) with a six-His tag at the N-terminal. The His-tagged Bromodomain was extracted from *E. coli* cells using 0.1 mg/ml lysozyme and sonication. The Bromodomain was then purified by affinity chromatography on a HisTRAP HP column, eluting with a linear 10-500 mM Imidazole gradient, over 20 Cv. Further purification was completed by Superdex 200 prep grade size exclusion column. Purified protein was stored at −80 C in 20 mM HEPES pH 7.5 and 100 mM NaCl.

Protocol for Bromodomain BRD2:

All components were dissolved in buffer composition of 50 mM HEPES pH7.4, 150 mm NaCl and 0.5 mM CHAPS with final concentrations of BRD2, 75 nM, fluorescent ligand 5 nM. 10 µl of this reaction mixture was added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy was read in Envision (λex=485 nm, λEM=530 nm; Dichroic −505 nM).

Protocol for Bromodomain BRD3:

All components were dissolved in buffer of composition 50 mM HEPES pH7.4, 150 mm NaCl and 0.5 mM CHAPS with final concentrations of BRD3 75 nM, fluorescent ligand 5 nM. 10 µl of this reaction mixture was added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy was read in Envision (λex=485 nm, λEM=530 nm; Dichroic −505 nM).

Protocol for Bromodomain BRD4:

All components were dissolved in buffer of composition 50 mM HEPES pH7.4, 150 mm NaCl and 0.5 mM CHAPS with final concentrations of BRD4 75 nM, fluorescent ligand 5 nM. 10 ml of this reaction mixture was added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy was read in Envision (λex=485 nm, λEM=530 nm; Dichroic −505 nM).

Time Resolved Fluorescence Resonance Energy Transfer (TR-FRET) Assay

The binding of the compounds of formula (I) to Bromodomains BRD2, BRD3 and BRD4 was assessed using a time resolved fluorescent resonance energy transfer binding assay, that measures the binding of an acetylated histone peptide to the bromodomain protein.

The bromodomain protein, histone peptide and a variable concentration of test compound are incubated together to reach thermodynamic equilibrium. The assay is configured such that in the absence of test compound the bromodomain and peptide are significantly bound (~30%) and in the presence of a sufficient concentration of a potent inhibitor this interaction is disrupted leading to a measurable drop in fluorescent resonance energy transfer.

Histone Peptide:

H-Ser-Gly-Arg-Gly-Lys(Ac)-Gly-Gly-Lys(Ac)-Gly-Leu-Gly-Lys(Ac)-Gly-Gly-Ala-Lys(Ac)-Arg-His-Gly-Ser-Gly-Ser-Lys(Biotin)-OH. 3TFA The protected peptide was assembled on a solid-phase synthesiser using preloaded Wang resin and utilising standard Fmoc synthesis protocols. The C-terminal lysine was protected by a hyper acid-labile group allowing for its selective removal at the end of the assembly and attachment of the biotin. The crude peptide was obtained after cleavage from the resin with a mixture of trifluoroacetic acid (TFA), triisopropylsilane and water (95:2.5:2.5) for 3 h at room temperature and was then purified using a C18 reverse-phase column utilising a 0.1% TFA-buffered water/acetonitrile gradient. The resulting fractions were analysed and fractions which were >95% pure by analytical HPLC and giving the correct mw (by MALDiTOF mass spectroscopy) were pooled and freeze dried. The final material was analysed by HPLC to confirm purity.

Protein Production:

Recombinant Human Bromodomains (BRD2 (1-473), BRD3 (1-435) and BRD4 (1-477)) were expressed in *E. coli* cells (in pET15b vector) with a six-His tag at the N-terminal. The His-tagged Bromodomain was extracted from *E. coli* cells using sonication and purified using a nickel sepharose 6FF column, the proteins were washed and then eluted with 50 mM Tris-Hcl pH8.0. 300 mM NaCl, 1 mM 3-mercaptoethanol and 20 mM Imidazole. Further purification was performed by affinity chromatography on a HisTRAP HP column, eluting with a linear 0-500 mM sodium chloride gradient, over 20 column volumes. Final purification was completed by Superdex 200 prep grade size exclusion column. Purified protein was stored at −80 C in 20 mM HEPES pH 7.5 and 100 mM NaCl. Protein identity was confirmed by peptide mass fingerprinting and predicted molecular weight confirmed by mass spectrometry.

Protocol for Bromodomain BRD2, 3 and 4 Assays:

All assay components were dissolved in buffer composition of 50 mM HEPES pH7.4, 50 mM NaCl and 0.5 mM CHAPS. The final concentration of bromodomain proteins were 100 nM and the histone peptide was 300 nM, these components are premixed and allowed to equilibrate for 1 hour in the dark. 8 µl of this reaction mixture was added to all wells containing 50 nl of various concentrations of test compound or DMSO vehicle (0.5% final) in Greiner 384 well black low volume microtitre plates and incubated in dark for 60 mins at room temperature. 2 µl of detection mixture containing anti-6his XL665 labeled antibody and streptavidin labeled with europium cryptate was added to all wells and a further dark incubation of at least 30 mins was performed. Plates were then read on the Envision platereader, (λex=317 nm, donor λEM=615 nm; acceptor λEM=665 nm; Dichroic LANCE dual). Time resolved fluorescent intensity measurements were made at both emission wavelengths and the ratio of acceptor/donor was calculated and used for data analysis. All data was normalized to the mean of 16 high and 16 low control wells on each plate. A four parameter curve fit of the following form was then applied:

$$y=a+((b-a)/(1+(10^{\wedge}x/10^{\wedge}c)^{\wedge}d)$$

Where 'a' is the minimum, 'b' is the Hill slope, 'c' is the pIC50 and 'd' is the maximum.

Examples 1-68 were tested in one or more of the above assays and were found to have a pIC50 in the range 6.0 to 7.5. Examples 1-5, 7, 10-19, 26, 28-31, 39-47, 49, 52 and 65 were found to have a pIC50 in the range 7.0-7.5 in at least one of the above assays.

Measurement of LPS Induced IL-6 Secretion from Whole Blood

Activation of monocytic cells by agonists of toll-like receptors such as bacterial lipopolysaccharide (LPS) results in production of key inflammatory mediators including IL-6. Such pathways are widely considered to be central to the pathophysiology of a range of auto-immune and inflammatory disorders.

Compounds to be tested are diluted to give a range of appropriate concentrations of which 1 µl of the diluted stocks is added to a 96 well plate. Following addition of whole blood (130 µl) the plates are incubated at 37 degrees (5% CO2) for 30 min before the addition of 10 µl of 2.8 ug/ml LPS, diluted in complete RPMI 1640 (final concentration=200 ng/ml), to give a total volume of 140 µl per well. After further incubation for 24 hours at 37 degrees, 140 µl of PBS are added to each well. The plates are sealed, shaken for 10 minutes and then centrifuged (2500 rpm×10 min). 100 µl of the supernatant are removed and IL-6 levels assayed by immunoassay (typically by MesoScale Discovery technology) either immediately or following storage at −20 degrees. Concentration response curves for each compound was generated from the data and an $IC_{50}$ value was calculated.

Examples 2, 3, 5-7, 9-12, 14-16, 19-25, 28-32, 34, 37, 38, 40, 42, 44-46, 48-49, 51-52, 54, 56-65, and 68 were tested in the above assay and were found to have a pIC50 in the range 5.5 to 7.3.

These data demonstrate that bromodomain inhibitors tested in the above whole blood assay inhibited the production of key inflammatory mediator IL-6.

In Vivo Mouse Endotoxemia Model

High doses of Endotoxin (bacterial lipopolysaccharide) administered to animals produce a profound shock syndrome including a strong inflammatory response, dysregulation of cardiovascular function, organ failure and ultimately mortality. This pattern of response is very similar to human sepsis and septic shock, where the body's response to a significant bacterial infection can be similarly life threatening.

To test the compounds for use in the invention groups of eight Balb/c male mice are given a lethal dose of 15 mg/kg LPS by intraperitoneal injection. Ninety minutes later, animals were dosed intravenously with vehicle (20% cyclodextrin 1% ethanol in apyrogen water) or compound (10 mg/kg). The survival of animals is monitored at 4 days.

Oncology Cell Growth Assay

Human cell lines (n=33 comprising 15 heme cell lines, 14 breast cell lines and 4 other cell lines) were cultured in RPMI-1640 containing 10% fetal bovine serum, 1000 viable cells per well were plated in 384-well black flat bottom polystyrene plates (Greiner #781086) in 48 µl of culture media. All plates were placed at 5% $CO_2$, 37° C. overnight. The following day one plate was harvested with CellTiter-Glo (CTG, Promega #G7573) for a time equal to 0 (T0) measurement and compound (20 point titration from 14.7 uM to 7 µM) was added to the remaining plates. The final concentration of DMSO in all wells was 0.15%. Cells were incubated for 72 hours or the indicated time and each plate was developed with CellTiter-Glo reagent using a volume equivalent to the cell culture volume in the wells. Plates were shaken for approximately 2 minutes and chemiluminescent signal was read on the Analyst GT (Molecular Devices) or EnVision Plate Reader (Perkin Elmer).

Results are expressed as a percent of the T0 and plotted against the compound concentration. The T0 value was normalized to 100% and represents the number of cells at time of compound addition and the concentration response data were fit with a 4 parameter curve fit using XLfit software (model 205). The concentration that inhibited cell growth by 50% ($gIC_{50}$) is the midpoint of the 'growth window' (between the T0 and DMSO control). The Ymin−T0 value is determined by subtracting the T0 value (100%) from the Ymin value (%) determined from the fit of the concentration response curve. Values from the wells with no cells were subtracted from all samples for background correction.

All publications, including but not limited to patents and patent applications, cited in this specification are herein incorporated by reference as if each individual publication were specifically and individually indicated to be incorporated by reference herein as though fully set forth.

What is claimed is:

1. A compound of formula (I) or a salt thereof (I)

in which

X and Y are independently CH or N provided that at least one of X and Y must be CH;

$R^1$ is a group $C(O)OR^4$ in which $R^4$ is $C_{1-3}$alkyl or $C_{3-7}$cycloalkyl; or $R^1$ is a group selected from phenyl, pyridyl, pyrazinyl and pyrimidinyl said groups being optionally substituted by one or two substituents selected from halogen, $C_{1-4}$alkyl and CN;

$R^2$ is $C_{1-4}$alkyl;

$R^3$ is $C_{1-4}$alkyl;

$R^5$ is hydrogen and $R^6$ is $C_{1-4}$alkyl substituted by one or more hydroxy or a —$NR^7R^8$ group in which $R^7$ and $R^8$ are independently hydrogen or a $C_{1-4}$alkyl group; or $R^5$ and $R^6$ together with the N to which they are attached form a saturated 4, 5 or 6 membered heterocyclyl ring optionally containing a further heteroatom selected from N, O and S, said heterocyclyl ring being optionally substituted by one or more Cl_4 alkyl, hydroxyl or amino groups; and m is 0, 1 or 2.

2. A compound or a salt thereof according to claim 1 in which X and Y are both CH.

3. A compound or a salt thereof according to claim 1 in which X is CH and Y is N.

4. A compound or a salt thereof according to claim 1 in which $R^1$ is a group $C(O)OR^4$ wherein $R^4$ is isopropyl.

5. A compound of salt thereof according to claim 1 in which $R^1$ is selected from

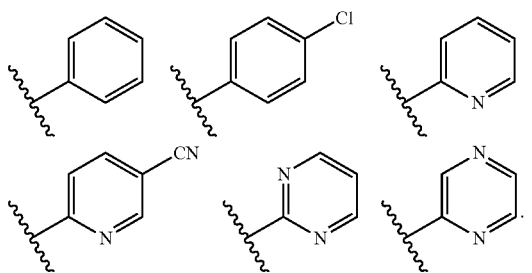

6. A compound or a salt thereof according to claim 1 in which $R^2$ is methyl.

7. A compound or a salt thereof according to claim 1 in which $R^3$ is methyl.

8. A compound or salt thereof according to claim 1 in which m is 0.

9. A compound or salt thereof according to claim 1 in which m is 1.

10. A compound or salt thereof according to claim 1 in which $R^5$ is hydrogen and $R^6$ is selected from

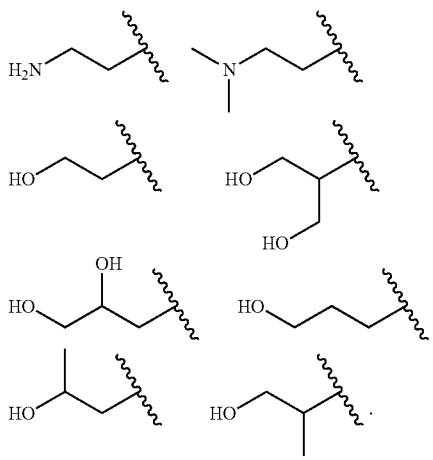

11. A compound or a salt thereof according to claim 1 in which $R^5$ and $R^6$ combine together with the N to which they are attached to form a group selected from

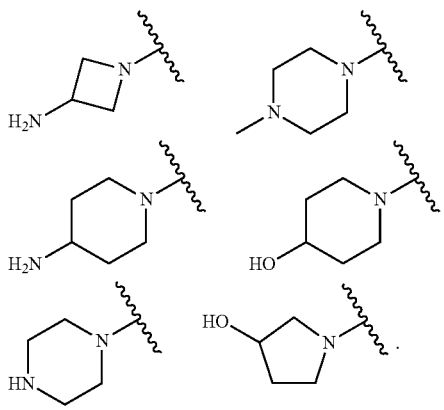

12. A compound or a salt thereof according to claim 1 wherein the compound of formula (I) is the (2S,4R) enantiomer.

13. A compound which is selected from 2-(4-((2S,4R)-1-Acetyl-4-((5-cyanopyridin-2-yl)amino)-2-methyl-1,2,3,4-tetrahydroquinolin-6-yl)phenyl)-N-(2-(dimethylamino)ethyl)acetamide;

6-((2S,4R)-1-acetyl-4-((5-cyanopyridin-2-yl)amino)-2-methyl-1,2,3,4-tetrahydroquinolin-6-yl)-N-(2-(dimethylamino)ethyl)nicotinamide; and 6-((2S,4R)-1-acetyl-4-((5-cyanopyridin-2-yl)amino)-2-methyl-1,2,3,4-tetrahydroquinolin-6-yl)-N-(2-hydroxyethyl)nicotinamide or a salt thereof.

14. A compound according to claim 1 or a pharmaceutically acceptable salt thereof.

15. A pharmaceutical composition which comprises a compound or a pharmaceutically acceptable salt thereof as defined in claim 14 and one or more pharmaceutically acceptable carriers, diluents or excipients.

16. A method of treating diseases or conditions for which a bromodomain inhibitor is indicated in a subject in need thereof which comprises administering a therapeutically effective amount of a compound or a pharmaceutically acceptable salt thereof as defined in claim 14, wherein the disease or condition is cancer.

* * * * *